US010294486B2

(12) United States Patent
Brower-Toland et al.

(10) Patent No.: US 10,294,486 B2
(45) Date of Patent: May 21, 2019

(54) COMPOSITIONS AND METHODS FOR ALTERING FLOWERING AND PLANT ARCHITECTURE TO IMPROVE YIELD POTENTIAL

(71) Applicant: Monsanto Technology LLC, St. Louis, MO (US)

(72) Inventors: Brent Brower-Toland, St. Louis, MO (US); Rico A. Caldo, Eureka, MO (US); Shunhong Dai, Creve Coeur, MO (US); Karen Gabbert, St. Louis, MO (US); Alexander Goldshmidt, David, CA (US); Miya D. Howell, Ballwin, MO (US); Balasulojini Karunanandaa, Creve Coeur, MO (US); Sivalinganna Manjunath, Chesterfield, MO (US); Bradley W. McDill, Carlsbad, CA (US); Daniel J. Ovadya, Davis, CA (US); Sasha Preuss, Webster Groves, MO (US); Elena A. Rice, Olivette, MO (US); Beth Savidge, Davis, CA (US); Vijay K. Sharma, Wildwood, MO (US)

(73) Assignee: Monsanto Technology LLC, St. Louis, MO (US)

(*) Notice: Subject to any disclaimer, the term of this patent is extended or adjusted under 35 U.S.C. 154(b) by 262 days.

(21) Appl. No.: 15/131,987

(22) Filed: Apr. 18, 2016

(65) Prior Publication Data

US 2016/0304891 A1    Oct. 20, 2016

Related U.S. Application Data

(60) Provisional application No. 62/150,142, filed on Apr. 20, 2015, provisional application No. 62/233,019, filed on Sep. 25, 2015.

(51) Int. Cl.
*C12N 15/82* (2006.01)
*C07K 14/415* (2006.01)

(52) U.S. Cl.
CPC .......... *C12N 15/827* (2013.01); *C07K 14/415* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| 5,880,330 | A | 3/1999 | Weigel et al. |
| 6,225,530 | B1 * | 5/2001 | Weigel ................. C07K 14/415 800/290 |
| 8,935,880 | B2 | 1/2015 | Ovadya et al. |
| 2004/0031072 | A1 | 2/2004 | La Rosa et al. |
| 2005/0223428 | A1 | 10/2005 | Torii et al. |
| 2010/0192249 | A1 | 7/2010 | Creelman et al. |
| 2014/0259905 | A1 | 9/2014 | Ovadya et al. |

FOREIGN PATENT DOCUMENTS

| CN | 102146124 A | 8/2011 |
| CN | 102994516 B | 4/2014 |
| WO | WO 2013/192081 A1 | 12/2013 |

OTHER PUBLICATIONS

Bowie et al, Science 247:1306-1310, 1990.*
McConnell et al, Nature 411 (6838):709-713, 2001.*
Benfey et al (1990, Science 250:959-966).*
Benfey et al (1989, EMBO J, 8(8):2195-2202.*
Fu et al (2011, Publication No. CN102146124 (A)).*
Li et al., "Molecular characterization and functional analysis of a Flowering locus T homolog gene from a *Phalaenopsis* orchid," *Genetics and Molecular Research*, 13(3):5982-5994 (2014).
Mouradov et al., "Control of Flowering Time: Interacting Pathways as a Basis for Diversity," *The Plant Cell*, S111-S130 (2002).
Nan et al., "GmFT2a and GmFT5a Redundantly and Differentially Regulate Flowering through Interaction with and Upregulation of the bZIP Transcription Factor GmFDL19 in Soybean," *PLoS ONE*, 9(5):e97669 (2014).
Notaguchi et al., "Long-Distance, Graft-Transmissible Action of *Arabidopsis* Flowering Locus T Protein to Promote Flowering," *Plant Cell Physiology*, 49(11): 1645-1658 (2008).
Ratcliffe et al., "A common mechanism controls the life cycle and architecture of plants," *Development*, 125:1609-1615 (1998).
Shannon et al., "A Mutation in *Arabidopsis* TFL1 Gene Affects Inflorescence Meristem Development," *The Plant Cell*, 3:877-892 (1991).
Sun et al., "GmFT2a, a Soybean Homolog of Flowering Locus T, Is Involved in Flowering Transition and Maintenance," *PLoS ONE*, 6(12):e29238 (2011).

(Continued)

*Primary Examiner* — Stuart F Baum
(74) *Attorney, Agent, or Firm* — David Lanzotti; Arnold & Porter Kaye Scholer LLP

(57) ABSTRACT

The present invention provides recombinant DNA constructs, vectors and molecules comprising a polynucleotide sequence encoding a florigenic FT protein operably linked to a vegetative stage promoter, which may also be a meristem-preferred or meristem-specific promoter. Transgenic plants, plant cells and tissues, and plant parts are further provided comprising a polynucleotide sequence encoding a florigenic FT protein. Transgenic plants comprising a florigenic FT transgene may produce more bolls, siliques, fruits, nuts, or pods per node on the transgenic plant, particularly on the main stem of the plant, relative to a control or wild type plant. Methods are further provided for introducing a florigenic FT transgene into a plant, and planting transgenic FT plants in the field including at higher densities. Transgenic plants of the present invention may thus provide greater yield potential than wild type plants and may be planted at a higher density due to their altered plant architecture.

24 Claims, 25 Drawing Sheets

Specification includes a Sequence Listing.

(56) References Cited

OTHER PUBLICATIONS

Abe et al., "FD, a bZIP Protein Mediating Signals from the Floral Pathway Integrator FT at the Shoot Apex," *Science*, 309:1052-1055 (2005).
Amasino et al., "The Timing of Flowering," *Plant Physiology*, 154:516-520 (2010).
Banfield et al., "The Structure of *Antirrhinum* Centroradialis Protein (CEN) Suggests a Role as a Kinase Regulator," *Journal of Molecular Biology*, 297:1159-1170 (2000).
Blackman et al., "The Role of Recently Derived FT Paralogs in Sunflower Domestication," *Current Biology*, 20:629-635 (2010).
Chen et al., "ERECTA family genes regulate development of cotyledons during embryogenesis," *FEBS Letters*, 588:3912-3917 (2014).
Chenna et al., "Multiple sequence alignment with the Clustal series of programs," *Nucleic Acids Research*, 31:3497-3500 (2003).
Corbesier et al., "FT Protein Movement Contributes to Long-Distance Signaling in Floral Induction of *Arabidopsis*," *Science*, 316:1030-1033 (2007).
Danilevskaya et al., "A Genomic and Expression Compendium of the Expanded PEBP Gene Family from Maize" *Plant Physiology*, 146:250-264 (2008).
Efroni et al., "A Protracted and Dynamic Maturation Schedule Underlies *Arabidopsis* Leaf Development," *The Plant Cell*, 20:2293-2306 (2008).
Finn et al., "Pfam: the protein families database," *Nucleic Acids Research (Database Issue)*, 42:D222-D230 (2014).
Fleury et al., "The *Arabidopsis thaliana* Homolog of Yeast BRE1 Has a Function in Cell Cycle Regulation during Early Leaf and Root Growth," *Plant Cell*, 19:417-432 (2007).
Harig et al., "Proteins from the Flowering Locus T-like subclade of the PEBP family act antagonistically to regulate floral initiation in tobacco," *Plant Journal*, 72:908-921 (2012).
Ho et al., "Structural Features Determining Flower-Promoting Activity of Herewith *Arabidopsis* Flowering Locus T," *Plant Cell*, 26:552-564 (2014).
Hsu et al., "Popular FT2 Shortens the Juvenile Phase and Promotes Seasonal Flowering," *Plant Cell*, 18:1846-1861 (2006).
International Search Report dated Oct. 14, 2016 for International Patent Application No. PCT/US2016/028130.
Jaeger et al., "FT Protein Acts as a Long Range Signal in *Arabidopsis*," *Current Biology*, 17:1050-1054 (2007).
Jaeger et al., "Interlocking Feedback Loops Govern the Dynamic Behavior of the Floral Transition in *Arabidopsis*," *The Plant Cell*, 25:820-833 (2013).
Kojima et al.,"Hd3a, a Rice Ortholog of the *Arabidopsis* FT gene, Promotes Transition to Flowering Downstream of Hd1 under Short-Day Conditions." *Plant Cell Physiology*, 43(10):1096-1105 (2002).
Kong et al., "Two Coordinately Regulated Homologs of Flowering Locus T Are Involved in the Control of Photoperiodic Flowering in Soybean," *Plant Physiology*, 154:1220-1231(2010).
Larkin et al., "Clustal W and Clustal X version 2.0," *Bioinformatics*, 23:2947-2948 (2007).
Li et al., "Receptor-like Kinases Key Regulators of Plant Development and Defense," *Journal of Integrative Plant Biology*, 55(12):1181-1187 (2013).
Lifschitz et al., "The tomato FT ortholog triggers systemic signals that regulate growth and flowering and substitute for diverse environmental stimuli," *Proceedings of the National Academy of Sciences*, 103:6398-6403 (2006).
Liu et al., "The Soybean Stem Growth Habit Gene Dt1 is an Ortholog of *Arabidopsis* Terminal Flower1," *Plant Physiology*, 153:198-210 (2010).
Mantegazza et al., "Analysis of the *Arabidopsis* REM gene family predicts functions during flower development," *Annals of Botany*, 114(7):1507-1515 (2014).
McGarry et al., "Manipulating plant architecture with members of the CETS Herewith gene family," *Plant Science*, 188-189:71-81 (2012).
Molinero-Rosales et al., "Single Flower Truss regulates the transition and maintenance of flowering in tomato," *Planta*, 218:427-434 (2004).
Pastore et al., "Late Meristem Identity2 acts together with LEAFY to activate APETALA1," *Development*, 138:3189-3198 (2011).
Patel et al., "BAR expressolog identification: expression profile similarity ranking of homologous genes in plant species," *Plant Journal*, 71:1038-1050 (2012).
Shani et al., "Stage-Specific Regulation of *Solanum lycopersicum* Leaf Maturation by Class 1 Knotted1-Like Homeobox Proteins," *The Plant Cell*, 21:3078-3092 (2009).
Shpak et al., "Stomatal Patterning and Differentiation by Synergistic Interactions of Receptor Kinases," *Science*, 309:290-293 (2005).
Shpak, E. "Diverse Roles of ERECTA Family Genes in Plant Development," *Journal of Integrative Plant Biology*, 55:1238-1250 (2013).
Taoka et al., "14-3-3 protein act as intracellular receptors for rice Hd3a florigen," *Nature*, 476:332-335 (2011).
Thompson et al., "Clustal W: improving the sensitivity of progressive multiple sequence alignment through sequence weighting, position-specific gap penalties and weight matrix choice," *Nucleic Acids Research*, 22:4673-4680 (1994).
Toufighi et al., "The Botany Array Resource: e-Northerns, Expression Angling, and promoter analyses," *Plant Journal*, 43: 153-163 (2005).
Trankner et al., "Over-expression of an FT-homologous gene of apple induces early flowering in annual and perennial plants," *Planta*, 232: 1309-1324 (2010).
Turck et al., "Regulation and Identity of Florigen: Flowering Locus T Moves Center Stage," *Annual Review of Plant Biology*, 59:573-594 (2008).
Wickland et al., "The Flowering Locus T/Terminal Flower 1 Gene Family: Functional Evolution and Molecular Mechanisms," *Molecular Plant*, 8:983-997.
Xiang et al., "Functional analysis of Flowering Locus T orthologs from spring orchid (*Cymbidium goeringii* Rchb. f.) that regulates the vegetative to reproductive transition," *Plant Cell & Biochemistry*, 58:98-105 (2012).
Yokoyama et al., "The *Arabidopsis* ERECTA gene is expressed in the shoot apical meristem and organ primordia," *The Plant Journal*, 15:301-310 (1998).
Zhai et al.,"GmFt4, a Homolog of Flowering Locus T, Is Positively Regulated by E1 and Functions as a Flowering Repressor in Soybean," *PLoS ONE*, 9(2):1-11 (2014).
McGarry et al., "Geminivirus-Mediated Delivery of Florigen Promotes Determinate Growth in Aerial Organs and Uncouples Flowering from Photoperiod in Cotton," *PLOS One*, 7(5):e36746 (2012).
McGarry et al., "Virus-Induced Flowering: An Application of Reproductive Biology to Benefit Plant Research and Breeding," *Plant Physiology*, 173:47-55 (2017).
Partial European Search Report dated Sep. 3, 2018 in European Application No. 16783657.6.

\* cited by examiner

| | SEQUENCE | 1 | 2 | 3 | 4 | 5 | 6 | 7 | 8 | 9 | 10 |
|---|---|---|---|---|---|---|---|---|---|---|---|
| 1 | Gm.FT2a | - | 90.6 (481) | 69.5 (369) | 71 (377) | 66.7 (354) | 60.6 (322) | 68.7 (365) | 64.2 (341) | 73.4 (390) | 66.5 (353) |
| 2 | Gm.FT2b | 90.6 (481) | - | 67.6 (359) | 69.9 (371) | 64.2 (341) | 58.4 (310) | 65.9 (350) | 62 (329) | 70.4 (374) | 65.9 (350) |
| 3 | Nt.FT | 70.3 (369) | 68.4 (359) | - | 76.6 (402) | 67.4 (354) | 58.5 (307) | 67 (352) | 62.9 (330) | 73.7 (387) | 67.8 (356) |
| 4 | Le.FT | 70.6 (377) | 69.5 (371) | 75.3 (402) | - | 67.4 (360) | 60.1 (321) | 67.4 (360) | 64.6 (345) | 73 (390) | 66.9 (357) |
| 5 | Gm.FT5A | 68.2 (354) | 65.7 (341) | 68.2 (354) | 69.4 (360) | - | 61.1 (317) | 65.9 (342) | 62.6 (325) | 70.7 (367) | 65.7 (341) |
| 6 | Zm.ZCN8 | 61 (322) | 58.7 (310) | 58.1 (307) | 60.8 (321) | 60 (317) | - | 57 (301) | 59.3 (313) | 61.4 (324) | 56.3 (297) |
| 7 | At.FT | 69.1 (365) | 66.3 (350) | 66.7 (352) | 68.2 (360) | 64.8 (342) | 57 (301) | - | 65.9 (348) | 72.5 (383) | 82.2 (434) |
| 8 | Os.HD3A | 63.1 (341) | 60.9 (329) | 61.1 (330) | 63.9 (345) | 60.2 (325) | 58 (313) | 64.4 (348) | - | 71.1 (384) | 63.9 (345) |
| 9 | Pt.FT | 74.3 (390) | 71.2 (374) | 73.7 (387) | 74.3 (390) | 69.9 (367) | 61.7 (324) | 73 (383) | 73.1 (384) | - | 71.8 (377) |
| 10 | At/TSF | 66.9 (353) | 66.3 (350) | 67.4 (356) | 67.6 (357) | 64.6 (341) | 56.3 (297) | 82.2 (434) | 65.3 (345) | 71.4 (377) | - |

*FIG. 1A*

|   | SEQUENCE | 1 | 2 | 3 | 4 | 5 | 6 | 7 | 8 | 9 | 10 |
|---|---|---|---|---|---|---|---|---|---|---|---|
| 1 | Gm.FT2a | - | 90.9 (160) | 74.4 (131) | 79.5 (140) | 65.6 (116) | 60.2 (106) | 72.2 (127) | 76.7 (135) | 80.7 (142) | 71.6 (126) |
| 2 | Gm.FT2b | 90.9 (160) | - | 72.2 (127) | 75.6 (133) | 61.9 (109) | 57.4 (101) | 71.6 (126) | 71.6 (126) | 76.1 (134) | 71 (125) |
| 3 | Nt.FT | 75.3 (131) | 73 (127) | - | 77.6 (135) | 65.5 (114) | 59.2 (103) | 74.1 (129) | 71.8 (125) | 77.6 (135) | 72.4 (126) |
| 4 | Le.FT | 79.1 (140) | 75.1 (133) | 76.3 (135) | - | 66.1 (117) | 59.3 (105) | 75.7 (134) | 79.1 (140) | 84.7 (150) | 75.1 (133) |
| 5 | Gm.FT5a | 67.4 (116) | 63.4 (109) | 66.3 (114) | 68 (117) | - | 58.7 (101) | 65.1 (112) | 65.1 (112) | 69.2 (119) | 67.4 (116) |
| 6 | Zm.ZCN8 | 60.6 (106) | 57.7 (101) | 58.9 (103) | 60 (105) | 57.7 (101) | - | 56.6 (99) | 58.3 (102) | 62.3 (109) | 56.6 (99) |
| 7 | At.FT | 72.6 (127) | 72 (126) | 73.7 (129) | 76.6 (134) | 64 (112) | 56.6 (99) | - | 71.4 (125) | 77.7 (136) | 81.7 (143) |
| 8 | Os.HD3A | 75.4 (135) | 70.4 (126) | 69.8 (125) | 78.2 (140) | 62.6 (112) | 57 (102) | 69.8 (125) | - | 79.3 (142) | 69.8 (125) |
| 9 | Pt.FT | 81.6 (142) | 77 (134) | 77.6 (135) | 86.2 (150) | 68.4 (119) | 62.6 (109) | 78.2 (136) | 81.6 (142) | - | 75.9 (132) |
| 10 | At.TSF | 72 (126) | 71.4 (125) | 72 (126) | 76 (133) | 66.3 (116) | 56.6 (99) | 81.7 (143) | 71.4 (125) | 75.4 (132) | - |

*FIG. 1B*

CLUSTAL 2.0.9 MULTIPLE SEQUENCE ALIGNMENT

```
Gm.FT2a    MPS---GSRDPLVGGVIGDVLDPFEYSIPMRVTYNNRDVSNGCEFKPSQVVNQPRVNIGG
Gm.FT2b    MPR---GSRDPLVGGVIGDVLDPFECSIPMRVTYNNKDVSNGCEFKPSQVVNQPRINIGG
Le.FT      MP----RERDPLVGRVVGDVLDPFTRTIGLRVIYRDREVNNGCEIRPSQVINQPRVEVGG
Pt.FT      MS----RBRDPLSVGRVIGDVLDPFTTKSISLRVTVSSREVNNGCEIKPSQVANQPRVDIGG
Os.HD3a    MAGSGRDRDPLVVGRVVGDVLDAFVRSTNLKVTGSKTVSSNCCEIKPSMVTHQPRVEVGG
At.FT      MS---INIRDPLIVSRVVGDVLDPFNRSITLKVTGQREVTNGLDIRPSQVNKPRVEIGG
At.TSF     MS---LSRRDPLVVGSVVGDVLDPFTRLVSLKVTYGHREVTNGLDIRPSQVLNKPIVEIGG
Nt.FT      ------MPRIDPLIVGRVVGDVLDPFTRSVDLRVVYNNREVNNACGLKPSQIVTQPRVQIGG
Gm.FT5a    ------MARENPLIVGGVIGDVLNPFTSSVSLTVSINNRAISNGLEIRPSQVVNRPRVTVGG
Zm.ZCN8    ------MSATDHLVMARVIQDVLDPFTPTIPLRITVMNRLLPSAELKPSAVVSKPRVDIGG
                      *  *:  ****:.*    :.  :   :       *:   *  .  :**

Gm.FT2a    DDLRNFYTLIAVDPDAPSPSDPNLREYLHWLVTDIPATTGASFGHEVTYESPRPMMGIH
Gm.FT2b    DDFRNFYTLIAVDPDAPSPSDPNLREYLHWLVTDIPATTGPTFGHEVTYENPRPMMGIH
Le.FT      DBLRTFFTLVMDDPDAPSPSDPNLREYLHWLVTDIPATTGSSFGQEIVSYESPRPSMGIH
Pt.FT      EDLRTFYTLVMDDPDAPSPSDPSLREYLHWLVTDIPATTGASFGHETVCYESPRPTMGIH
Os.HD3a    NDMRTFYTLVMVDPDAPSPSDPNLREYLHWLVTDIPGTAASFGQEVNCYESPRPTMGIH
At.FT      EDLRNFYTLVMVDPDVPSPSNPHLREYLHWLVTDIPATTGTFGNEIVCYENPSPTAGIH
At.TSF     DDFRNFYTLVMVDPDVPSPSNPHQREYLHWLVTDIPATTGNAFGNEVVCYESPRPPSGIH
Nt.FT      DDLRNFYTLVMVDPDAPSPSNPNLREYLHWLVTDIPATTDTSFGNEVICYENPQPSLGIH
Gm.FT5a    EDLRTFYTLVMVDADAPSPSNPVLREYLHWWVTDIPATTNASFGREVVFYESPNPSVGIH
Zm.ZCN8    SDMRAFYTLVLIDPPDAPSPSHPSLREYLHWVTDIPETTSVNFGQELIFYERPDPRSGIH
             :*  :  .  * :****.*  .****  *****.**  .    :  ** * *** 
```

FIG. 1C

```
Gm.FT2a    RLVFVLFRQLGRETVYAPGWRQNFNTKEFAELYNLGLPVAAVYFNIQRESGSGGRRLY--    176
Gm.FT2b    RIVFVLFRQQGRETVYAPGWRQNFTTREFAELYNLGLPVAAVYFNIQRESGCGGRRLC--    176
Le.FT      REVFVLFRQLGRQTVYAPGWRQNFNTRDFAELYNLGLPVAAVYFNCQRESGSGGRRRSAD    177
Pt.FT      REVFVLFRQLGRQTVYAPGWRQNFNTRDFAEVYNLGSPVAAVYFNCQRESGSGGRRR---    174
Os.HD3a    RLVFVLFQQLGRQTVYAPGWRQNFNTKDFAELYNLGSPVAAVYFNCQREAGSGGRRVYP-    179
At.FT      RVVFILFRQLGRQTVYAPGWRQNFNTREFAELYNLGLPVAAVYFNCQRESGCGGRRL---    175
At.TSF     RIVFVLFRQLGRQTVYAPGWRQQFNTREFAELYNLGLPVAASYFNCQRENGCGGRRT---    175
Nt.FT      REVFVLFRQLGRETVYAPGWRQNFSTRDFAEVYNLGLPVSAVYFNCHRESGTGGRRAY--    174
Gm.FT5a    RIVFVLFQQLGRDTVITPEWRHNFNSRNFAEINNL-APVAAAYANCQRERGCGGRRY---    172
Zm.ZCN8    RLVFVLFRQLGRGTVFAPEMRHNFNCRSFARQYHLSIATAT-HFNCQREGGSGGRRFREE    175
           *.*::**:.** :  ** .:  * .: :* .**  .:*: *:*    *.::   *
```

FIG. 1C
CONTINUED

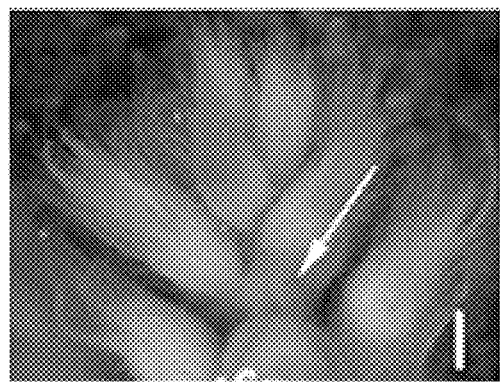
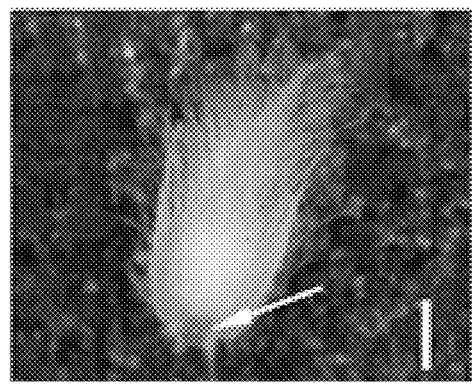
*FIG. 5A*  *FIG. 5B*
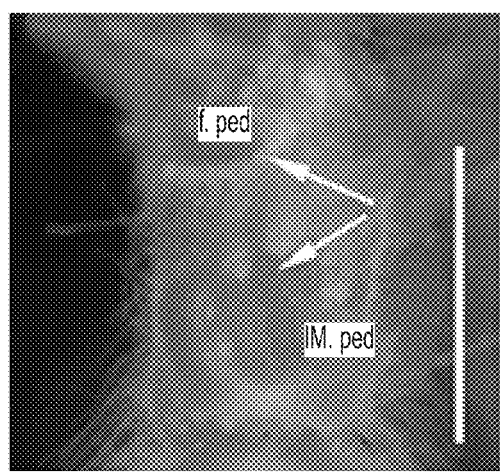
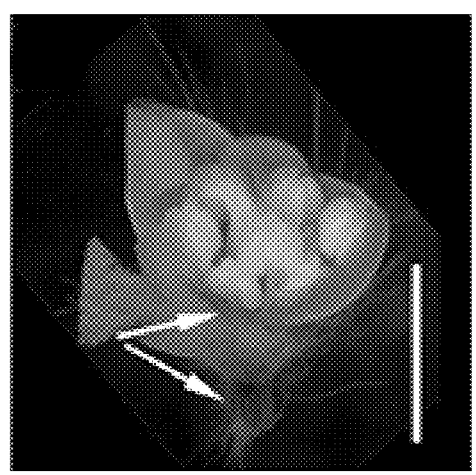
*FIG. 5C*  *FIG. 5D*
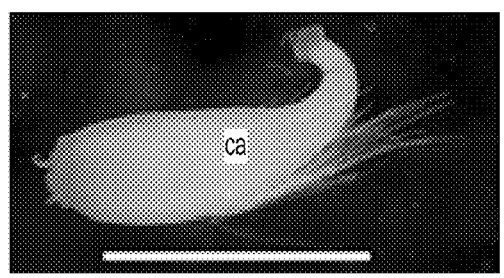
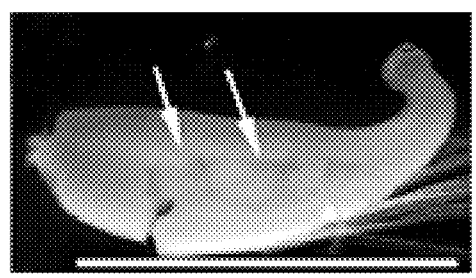
*FIG. 5E*  *FIG. 5F*

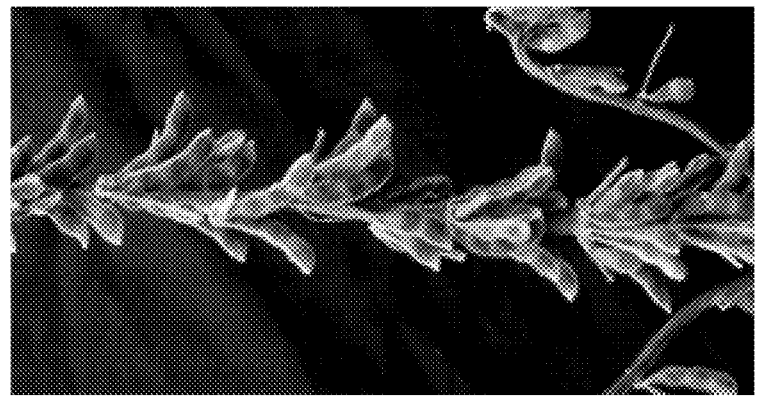
FIG. 11

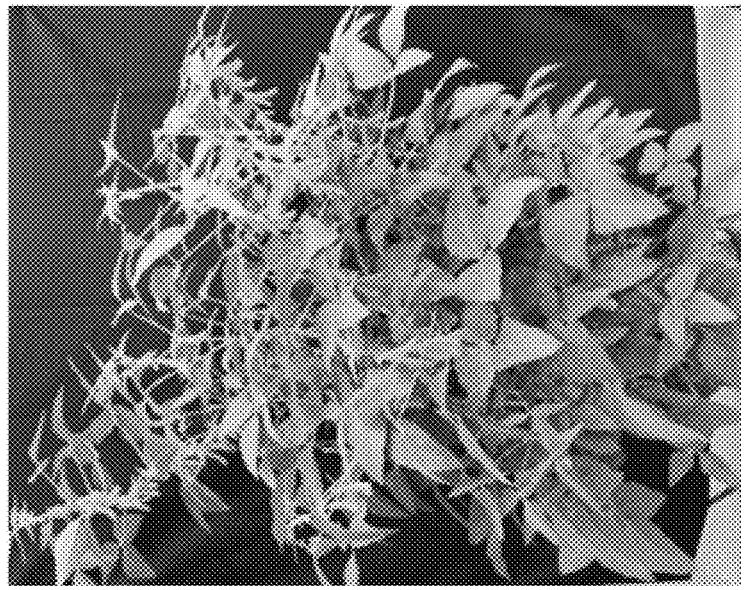
FIG. 12A

FIG. 12B

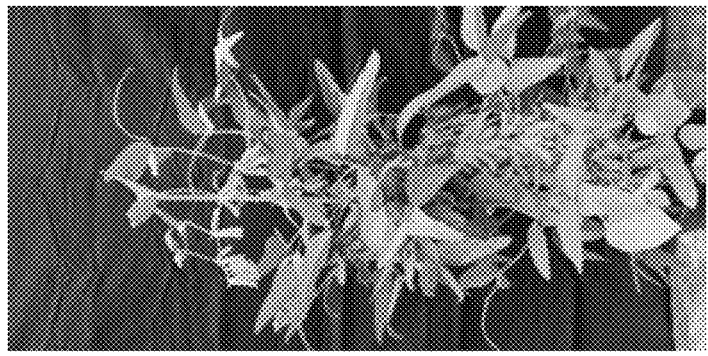
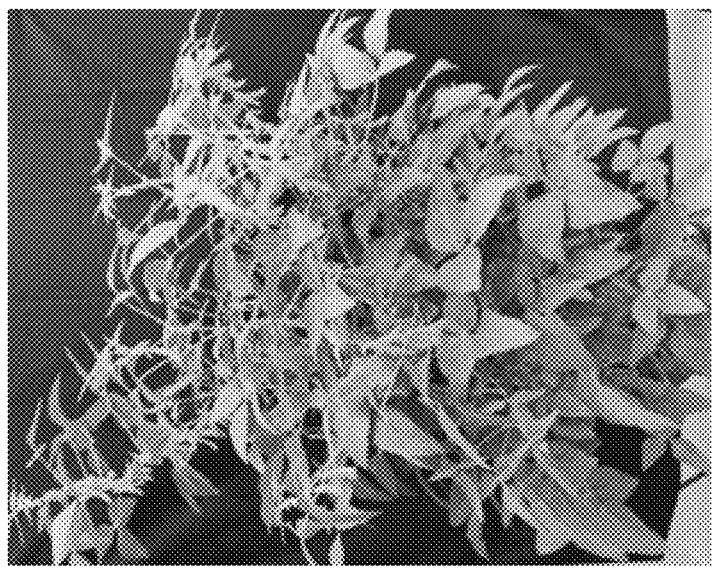
FIG. 13A

FIG. 13B

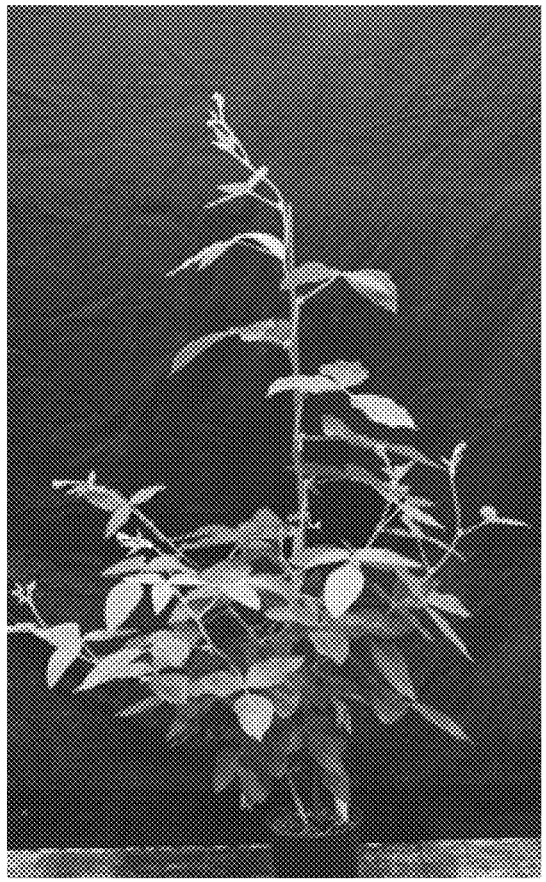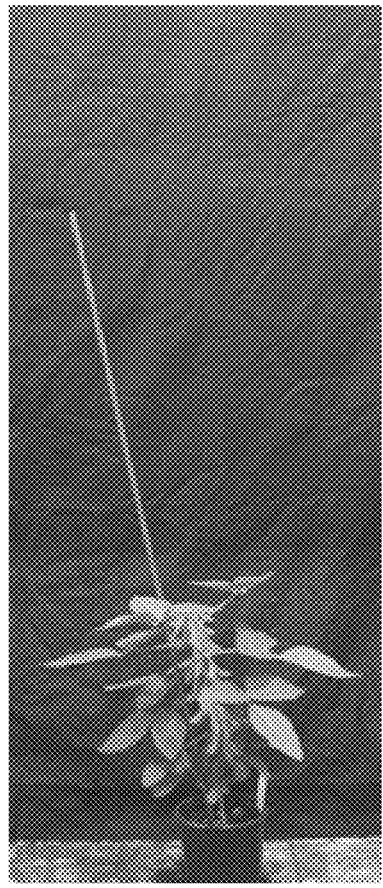
FIG. 15

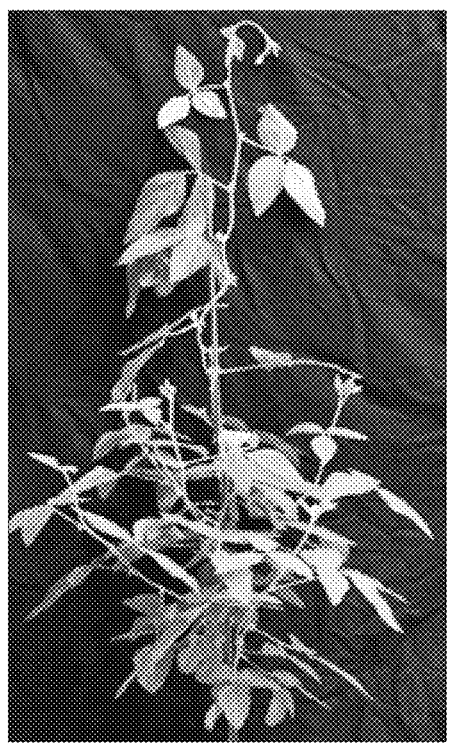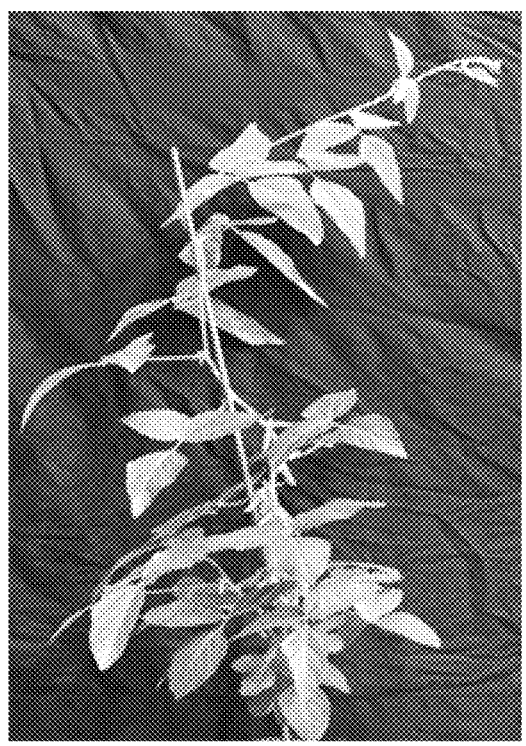
WT  pER::Gm.FT5a
*FIG. 16*

SEQUENCE LISTING

<160> NUMBER OF SEQ ID NOS: 38

<210> SEQ ID NO 1
<211> LENGTH: 531
<212> TYPE: DNA
<213> ORGANISM: Glycine max

<400> SEQUENCE: 1

```
atgcctagtg aagtaggga tcctctcgtt gttggggag taattgggga tgtattggat      60
ccttttgaat attctattcc tatgagggtt acctacaata acagagatgt cagcaatgga     120
tgtgaattca accctcaca gttgtcaac caaccaaggg taaatatcgg tggtgatgac     180
ctcaggaact tctatacttt gattgcggtt gatcccgatg cacctagccc aagtgacccc     240
aatttgagag aatacctcca ttggttggtg actgatatcc cagcaacaac aggggctagt     300
ttcggccatg aggttgtaac atatgaaagt ccaagaccaa tgatgggat tcatcgtttg     360 gtgtttgtgt tatttcgtca actgggtagg agaccgtgt atgcaccagg atggcgccag     420
aatttcaaca ctaaagaatt tgctgaactt acaaccttg dattgccagt tgctgctgtc      480
tatttcaaca ttcagaggga atctggttct ggtggaagga ggttatacta a              531
```

<210> SEQ ID NO 2
<211> LENGTH: 176
<212> TYPE: PRT
<213> ORGANISM: Glycine max

<400> SEQUENCE: 2

Met Pro Ser Gly Ser Arg Asp Pro Leu Val Val Gly Val Ile Gly
1               5                   10                  15

Asp Val Leu Asp Pro Phe Glu Tyr Ser Ile Pro Met Arg Val Thr Tyr
                20                  25                  30

Asn Asn Arg Asp Val Ser Asn Gly Cys Glu Phe Lys Pro Ser Gln Val
            35                  40                  45

Val Asn Gln Pro Arg Val Asn Ile Gly Gly Asp Asp Leu Arg Asn Phe
        50                  55                  60

Tyr Thr Leu Ile Ala Val Asp Pro Asp Ala Pro Ser Pro Ser Asp Pro
65                  70                  75                  80

Asn Leu Arg Glu Tyr Leu His Trp Leu Val Thr Asp Ile Pro Ala Thr
                85                  90                  95

Thr Gly Ala Ser Phe Gly His Glu Val Val Thr Tyr Glu Ser Pro Arg
            100                 105                 110

Pro Met Met Gly Ile His Arg Leu Val Phe Val Leu Phe Arg Gln Leu
        115                 120                 125

Gly Arg Glu Thr Val Tyr Ala Pro Gly Trp Arg Gln Asn Phe Asn Thr
    130                 135                 140

Lys Glu Phe Ala Glu Leu Tyr Asn Leu Gly Leu Pro Val Ala Ala Val
145                 150                 155                 160

Tyr Phe Asn Ile Gln Arg Glu Ser Gly Ser Gly Gly Arg Arg Leu Tyr
                165                 170                 175

<210> SEQ ID NO 3
<211> LENGTH: 519
<212> TYPE: DNA
<213> ORGANISM: Glycine max

<400> SEQUENCE: 3

```
atggcacggg agaaccctct tgttattggt ggtgtgattg ggatgttct caaccctttt      60
```

```
acaagctccg tttctttgac tgtttcaatc aataataggg cgattagcaa tggcttggaa    120
ctcaggccct ctcaagttgt taatcgccct agggttactg ttggtggtga agacctaagg    180
accttctaca ctctggttat ggtggatgca gatgcaccta gccctagcaa ccctgtcttg    240
agggaatacc ttcactggat ggtgacagat attccagcta ccacaaatgc aagctttggg    300
agagaggttg tgttttatga gagcccgaac ccttcagtag ggattcatcg aatcgtgttc    360
gtattgttcc agcaattggg cagagacact gtcatcaccc cagaatggcg ccataatttc    420
aattccagaa actttgctga aattaataac cttgcacctg ttgcagcagc ttatgccaac    480
tgccaaagag agcgtggttg cggtggaagg agatattaa                           519
```

<210> SEQ ID NO 4
<211> LENGTH: 172
<212> TYPE: PRT
<213> ORGANISM: Glycine max

<400> SEQUENCE: 4

```
Met Ala Arg Glu Asn Pro Leu Val Ile Gly Gly Val Ile Gly Asp Val
1               5                   10                  15

Leu Asn Pro Phe Thr Ser Ser Val Ser Leu Thr Val Ser Ile Asn Asn
            20                  25                  30

Arg Ala Ile Ser Asn Gly Leu Glu Leu Arg Pro Ser Gln Val Val Asn
        35                  40                  45

Arg Pro Arg Val Thr Val Gly Gly Glu Asp Leu Arg Thr Phe Tyr Thr
    50                  55                  60

Leu Val Met Val Asp Ala Asp Ala Pro Ser Pro Ser Asn Pro Val Leu
65                  70                  75                  80

Arg Glu Tyr Leu His Trp Met Val Thr Asp Ile Pro Ala Thr Thr Asn
                85                  90                  95

Ala Ser Phe Gly Arg Glu Val Val Phe Tyr Glu Ser Pro Asn Pro Ser
            100                 105                 110

Val Gly Ile His Arg Ile Val Phe Val Leu Phe Gln Gln Leu Gly Arg
        115                 120                 125

Asp Thr Val Ile Thr Pro Glu Trp Arg His Asn Phe Asn Ser Arg Asn
    130                 135                 140

Phe Ala Glu Ile Asn Asn Leu Ala Pro Val Ala Ala Ala Tyr Ala Asn
145                 150                 155                 160

Cys Gln Arg Glu Arg Gly Cys Gly Gly Arg Arg Tyr
                165                 170
```

<210> SEQ ID NO 5
<211> LENGTH: 531
<212> TYPE: DNA
<213> ORGANISM: Glycine max

<400> SEQUENCE: 5

```
atgcctcgtg gaagtaggga ccctctagtt gttgggcgtg tgattgggga tgtattggac     60 cctttttgaat gttctattcc tatgagggtc acctacaata acaaagatgt cagcaatgga    120
tgtgaattca aaccctcaca agttgtcaac caaccaagaa taaatatcgg tggtgatgat    180
ttcaggaact tctacacttt gatcgcggtt gatcctgatg cacctagccc aagtgatccc    240
aatttcagag aataccttcca ttggttagta actgacattc agcaacaac ggggcctact    300 ttcggtcatg aggttgtaac atatgaaaat ccacgaccca tgatgggat ccatcgtata    360 gtctttgtgt tatttcgtca acagggtaga gagacagtgt atgcaccagg atggcgccaa    420
```

```
aatttcatta ctagagaatt tgctgaactt tacaatcttg gattgccagt tgctgctgtc    480
tattttaaca tccagagaga atctggttgt ggtggaagaa ggctatgtta a            531
```

<210> SEQ ID NO 6
<211> LENGTH: 176
<212> TYPE: PRT
<213> ORGANISM: Glycine max

<400> SEQUENCE: 6

```
Met Pro Arg Gly Ser Arg Asp Pro Leu Val Val Gly Arg Val Ile Gly
1               5                   10                  15

Asp Val Leu Asp Pro Phe Glu Cys Ser Ile Pro Met Arg Val Thr Tyr
            20                  25                  30

Asn Asn Lys Asp Val Ser Asn Gly Cys Glu Phe Lys Pro Ser Gln Val
        35                  40                  45

Val Asn Gln Pro Arg Ile Asn Ile Gly Gly Asp Asp Phe Arg Asn Phe
    50                  55                  60

Tyr Thr Leu Ile Ala Val Asp Pro Asp Ala Pro Ser Pro Ser Asp Pro
65                  70                  75                  80

Asn Phe Arg Glu Tyr Leu His Trp Leu Val Thr Asp Ile Pro Ala Thr
                85                  90                  95

Thr Gly Pro Thr Phe Gly His Glu Val Val Thr Tyr Glu Asn Pro Arg
            100                 105                 110

Pro Met Met Gly Ile His Arg Ile Val Phe Val Leu Phe Arg Gln Gln
        115                 120                 125

Gly Arg Glu Thr Val Tyr Ala Pro Gly Trp Arg Gln Asn Phe Ile Thr
    130                 135                 140

Arg Glu Phe Ala Glu Leu Tyr Asn Leu Gly Leu Pro Val Ala Ala Val
145                 150                 155                 160

Tyr Phe Asn Ile Gln Arg Glu Ser Gly Cys Gly Arg Arg Leu Cys
                165                 170                 175
```

<210> SEQ ID NO 7
<211> LENGTH: 528
<212> TYPE: DNA
<213> ORGANISM: Zea mays

<400> SEQUENCE: 7

```
atgtcagcaa ccgatcattt ggttatggct cgtgtcatac aggatgtatt ggatcccttt    60
acaccaacca ttccactaag aataacgtac aacaataggc tacttctgcc aagtgctgag   120
ctaaagccat ccgcggttgt aagtaaacca cgagtcgata tcggtggcag tgacatgagg   180
gctttctaca ccctggtact gattgacccg gatgccccaa gtccaagcca tccatcacta   240
agggagtact tgcactggat ggtgacagat attccagaaa caactagtgt caactttggc   300
caagagctaa tattttatga gaggccggac ccaagatctg gcatccacag gctggtattt   360
gtgctgttcc gtcaacttgg caggggggaca gttttgcac agaaatgcg ccacaacttc    420
```
(continuing)
```
aactgcagaa gctttgcacg gcaatatcac ctcagcattg ccaccgctac acatttcaac   480
tgtcaaaggg aaggtggatc cggcggaaga aggtttaggg aagagtag                528
```

<210> SEQ ID NO 8
<211> LENGTH: 175
<212> TYPE: PRT
<213> ORGANISM: Zea mays

<400> SEQUENCE: 8

```
Met Ser Ala Thr Asp His Leu Val Met Ala Arg Val Ile Gln Asp Val
1               5                   10                  15

Leu Asp Pro Phe Thr Pro Thr Ile Pro Leu Arg Ile Tyr Asn Asn
            20              25                  30

Arg Leu Leu Pro Ser Ala Glu Leu Lys Pro Ser Ala Val Val Ser
        35              40                  45

Lys Pro Arg Val Asp Ile Gly Gly Ser Asp Met Arg Ala Phe Tyr Thr
50                  55                  60

Leu Val Leu Ile Asp Pro Asp Ala Pro Ser Pro Ser His Pro Ser Leu
65                  70                  75                  80

Arg Glu Tyr Leu His Trp Met Val Thr Asp Ile Pro Glu Thr Thr Ser
                85                  90                  95

Val Asn Phe Gly Gln Glu Leu Ile Phe Tyr Glu Arg Pro Asp Pro Arg
                100                 105                 110

Ser Gly Ile His Arg Leu Val Phe Val Leu Phe Arg Gln Leu Gly Arg
                115                 120                 125

Gly Thr Val Phe Ala Pro Glu Met Arg His Asn Phe Asn Cys Arg Ser
130                 135                 140

Phe Ala Arg Gln Tyr His Leu Ser Ile Ala Thr Ala Thr His Phe Asn
145                 150                 155                 160

Cys Gln Arg Glu Gly Gly Ser Gly Gly Arg Arg Phe Arg Glu Glu
                165                 170                 175

<210> SEQ ID NO 9
<211> LENGTH: 525
<212> TYPE: DNA
<213> ORGANISM: Nicotiana tabacum

<400> SEQUENCE: 9
atgccaagaa tagatccttt gatagttggt cgtgtggtag agatgttttt agatccattc    60
acaaggtctg ttgatcttag agtggtttac aataataggg aagtcaacaa tgcatgtggc   120
ttgaaacctt ctcaaattgt tacgcaacct agggttcaaa ttggagggga tgatcttcgc   180 aactttttaca ctctggttat ggtggatcct gatgctccaa gcccaagcaa ccctaacctg   240
agggagtatc tacactggct ggtcacagat atcccagcaa ctacagatac aagctttgga   300
aatgaagtta tatgctacga gaatccacaa ccatcattgg gaattcatcg ctttgttttc   360
gtgttgtttc gacaattggg tcgcgaaact gtgtatgcac aggttggcg tcagaatttc   420 agcacaagag actttgcaga agtttacaat cttggtttgc ccgtttctgc tgtttacttc   480
aattgccata gggagagtgg tactggtggc cgccgcgcat attaa                   525

<210> SEQ ID NO 10
<211> LENGTH: 174
<212> TYPE: PRT
<213> ORGANISM: Nicotiana tabacum

<400> SEQUENCE: 10

Met Pro Arg Ile Asp Pro Leu Ile Val Gly Arg Val Val Gly Asp Val
1               5                   10                  15

Leu Asp Pro Phe Thr Arg Ser Val Asp Leu Arg Val Val Tyr Asn Asn
            20                  25                  30

Arg Glu Val Asn Asn Ala Cys Gly Leu Lys Pro Ser Gln Ile Val Thr
        35                  40                  45

Gln Pro Arg Val Gln Ile Gly Gly Asp Asp Leu Arg Asn Phe Tyr Thr
50                  55                  60
```

Leu Val Met Val Asp Pro Asp Ala Pro Ser Pro Ser Asn Pro Asn Leu
65                  70                  75                  80

Arg Glu Tyr Leu His Trp Leu Val Thr Asp Ile Pro Ala Thr Thr Asp
            85                  90                  95

Thr Ser Phe Gly Asn Glu Val Ile Cys Tyr Glu Asn Pro Gln Pro Ser
            100                 105                 110

Leu Gly Ile His Arg Phe Val Phe Val Leu Phe Arg Gln Leu Gly Arg
            115                 120                 125

Glu Thr Val Tyr Ala Pro Gly Trp Arg Gln Asn Phe Ser Thr Arg Asp
            130                 135                 140

Phe Ala Glu Val Tyr Asn Leu Gly Leu Pro Val Ser Ala Val Tyr Phe
145                 150                 155                 160

Asn Cys His Arg Glu Ser Gly Thr Gly Gly Arg Arg Ala Tyr
            165                 170

<210> SEQ ID NO 11
<211> LENGTH: 534
<212> TYPE: DNA
<213> ORGANISM: Solanum lycopersicum

<400> SEQUENCE: 11

| | | |
|---|---|---|
| atgcctagag aacgtgatcc tcttgttgtt ggtcgtgtgg taggggatgt attggaccct | 60 |
| ttcacaagaa ctattggcct aagagttata tatagagata gagaagttaa taatggatgc | 120 |
| gagcttaggc cttcccaagt tattaaccag ccaagggttg aagttggagg agatgaccta | 180 |
| cgtacctttt tcactttggt tatggtggac cctgatgctc caagtccgag tgatccaaat | 240 |
| ctgagagaat accttcactg gttggtcacc gatattccag ctaccacagg ttcaagtttt | 300 |
| gggcaagaaa tagtgagcta tgaaagtcca agaccatcaa tgggaataca tcgatttgta | 360 |
| tttgtattat tcagacaatt aggtcggcaa acagtgtatg ctccaggatg gcgtcagaat | 420 |
| ttcaacacaa gagattttgc agaactttat aatcttggtt tacctgttgc tgctgtctat | 480 |
| tttaattgtc aaagagagag tggcagtggt ggacgtagaa gatctgctga ttga | 534 |

<210> SEQ ID NO 12
<211> LENGTH: 177
<212> TYPE: PRT
<213> ORGANISM: Solanum lycopersicum

<400> SEQUENCE: 12

Met Pro Arg Glu Arg Asp Pro Leu Val Val Gly Arg Val Val Gly Asp
1               5                   10                  15

Val Leu Asp Pro Phe Thr Arg Thr Ile Gly Leu Arg Val Ile Tyr Arg
            20                  25                  30

Asp Arg Glu Val Asn Asn Gly Cys Glu Leu Arg Pro Ser Gln Val Ile
            35                  40                  45

Asn Gln Pro Arg Val Glu Val Gly Gly Asp Asp Leu Arg Thr Phe Phe
        50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
            85                  90                  95

Gly Ser Ser Phe Gly Gln Glu Ile Val Ser Tyr Glu Ser Pro Arg Pro
            100                 105                 110

Ser Met Gly Ile His Arg Phe Val Phe Val Leu Phe Arg Gln Leu Gly
            115                 120                 125

```
Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Ser Ala
                165                 170                 175

Asp

<210> SEQ ID NO 13
<211> LENGTH: 528
<212> TYPE: DNA
<213> ORGANISM: Arabidopsis thaliana

<400> SEQUENCE: 13
atgtctataa atataagaga ccctcttata gtaagcagag ttgttggaga cgttcttgat      60
ccgtttaata gatcaatcac tctaaaggtt acttatggcc aaagagaggt gactaatggc    120
ttggatctaa ggccttctca ggttcaaaac aagccaagag ttgagattgg tggagaagac    180
ctcaggaact tctatacttt ggttatggtg atccagatg ttccaagtcc tagcaaccct     240
caccctccgag aatatctcca ttggttggtg actgatatcc ctgctacaac tggaacaacc   300
tttggcaatg agattgtgtg ttacgaaaat ccaagtccca ctgcaggaat tcatcgtgtc    360
gtgtttatat tgtttcgaca gcttggcagg caaacagtgt atgcaccagg tggcgccag    420
aacttcaaca ctcgcgagtt tgctgagatc tacaatctcg gccttcccgt ggccgcagtt    480
ttctacaatt gtcagaggga gagtggctgc ggaggaagaa gactttag                  528

<210> SEQ ID NO 14
<211> LENGTH: 175
<212> TYPE: PRT
<213> ORGANISM: Arabidopsis thaliana

<400> SEQUENCE: 14

Met Ser Ile Asn Ile Arg Asp Pro Leu Ile Val Ser Arg Val Val Gly
1               5                  10                  15

Asp Val Leu Asp Pro Phe Asn Arg Ser Ile Thr Leu Lys Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
        50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175
```

<210> SEQ ID NO 15
<211> LENGTH: 528
<212> TYPE: DNA
<213> ORGANISM: Arabidopsis thaliana

<400> SEQUENCE: 15

```
atgtctttaa gtcgtagaga tcctcttgtg gtcggcagtg ttgttggaga tgttcttgat      60
cctttcacga ggttggtctc tcttaaggtc acttatggcc atagagaggt tactaatggc     120
ttggatctaa ggccttctca agttctgaac aaaccaatag tggagattgg aggagacgac     180
ttcagaaatt tctacacctt ggttatggtg atccagatg tgccgagtcc aagcaaccct      240
caccaacgag aatatctcca ctggttggtg actgatatac ctgccaccac tggaaatgcc     300
tttggcaatg aggtggtgtg ctacgagagt ccacgtcccc cctcgggaat tcatcgtatt     360
gtgttggtat tgttccggca actcggaaga caaacggttt atgcaccggg gtggcgccaa     420
cagttcaaca ctcgtgagtt tgctgagatc tacaatcttg gtcttcctgt ggctgcctct     480
tacttcaact gccagaggga gaatggctgt ggggaagaa gaacgtag                   528
```

<210> SEQ ID NO 16
<211> LENGTH: 175
<212> TYPE: PRT
<213> ORGANISM: Arabidopsis thaliana

<400> SEQUENCE: 16

```
Met Ser Leu Ser Arg Arg Asp Pro Leu Val Val Gly Ser Val Val Gly
1               5                   10                  15
Asp Val Leu Asp Pro Phe Thr Arg Leu Val Ser Leu Lys Val Thr Tyr
            20                  25                  30
Gly His Arg Glu Val Thr Asn Gly Leu Asp Leu Arg Pro Ser Gln Val
        35                  40                  45
Leu Asn Lys Pro Ile Val Glu Ile Gly Gly Asp Asp Phe Arg Asn Phe
    50                  55                  60
Tyr Thr Leu Val Met Val Asp Pro Asp Val Pro Ser Pro Ser Asn Pro
65                  70                  75                  80
His Gln Arg Glu Tyr Leu His Trp Leu Val Thr Asp Ile Pro Ala Thr
                85                  90                  95
Thr Gly Asn Ala Phe Gly Asn Glu Val Val Cys Tyr Glu Ser Pro Arg
            100                 105                 110
Pro Pro Ser Gly Ile His Arg Ile Val Leu Val Leu Phe Arg Gln Leu
        115                 120                 125
Gly Arg Gln Thr Val Tyr Ala Pro Gly Trp Arg Gln Gln Phe Asn Thr
    130                 135                 140
Arg Glu Phe Ala Glu Ile Tyr Asn Leu Gly Leu Pro Val Ala Ala Ser
145                 150                 155                 160
Tyr Phe Asn Cys Gln Arg Glu Asn Gly Cys Gly Gly Arg Arg Thr
                165                 170                 175
```

<210> SEQ ID NO 17
<211> LENGTH: 540
<212> TYPE: DNA
<213> ORGANISM: Oryza sativa

<400> SEQUENCE: 17

```
atggccggaa gtggcaggga cagggaccct cttgtggttg gtagggttgt gggtgatgtg      60
ctggacgcgt tcgtccggag caccaacctc aaggtcacct atggctccaa gaccgtgtcc     120
aatggctgcg agctcaagcc gtccatggtc acccaccagc ctagggtcga ggtcggcggc     180
```

```
aatgacatga ggacattcta caccctttgtg atggtagacc cagatgcacc aagcccaagt     240
gaccctaacc ttagggagta tctacattgg ttggtcactg atattcctgg tactactgca     300
gcgtcatttg gcaagaggt gatgtgctac gagagcccaa ggccaaccat ggggatccac      360
cggctggtgt tcgtgctgtt ccagcagctg gggcgtcaga cagtgtacgc gcccgggtgg     420
cgtcagaact tcaacaccaa ggacttcgcc gagctctaca acctcggctc gccggtcgcc     480
gccgtctact tcaactgcca gcgcgaggca ggctccggcg caggagggt ctaccccctag     540
```

<210> SEQ ID NO 18
<211> LENGTH: 179
<212> TYPE: PRT
<213> ORGANISM: Oryza sativa

<400> SEQUENCE: 18

```
Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Pro
```

<210> SEQ ID NO 19
<211> LENGTH: 525
<212> TYPE: DNA
<213> ORGANISM: Populus trichocarpa

<400> SEQUENCE: 19

```
atgtcaaggg acagagatcc tctgagcgtt ggccgtgtta taggggacgt gctggacccc     60
ttcacaaagt ctatctccct cagggtcact tacagctcca gagaggtcaa caatggttgc    120
gagctcaagc cctctcaggt tgccaaccag cctaggggttg atattggcgg ggaagatcta    180
aggaccttct acactctggt tatggtggac cctgatgcac ccagcccaag tgaccccagc    240
ctaagagaat atttgcattg gttggtgact gatattccag caacaactgg ggcaagcttt    300
ggccatgaaa ctgtgtgcta tgagagcccg aggccgacaa tgggaattca tcggtttgtt    360
ttcgtcttgt ttcggcaact gggcaggcaa actgtgtatg cccctgggtg gcgccagaac    420
ttcaacacca gagactttgc tgaggtctac aatcttggat cgccagtggc tgctgtttat    480
```
ttcaactgcc agagggagag tggctctggt ggtaggaggc gataa         525

<210> SEQ ID NO 20
<211> LENGTH: 174
<212> TYPE: PRT
<213> ORGANISM: Populus trichocarpa

<400> SEQUENCE: 20

Met Ser Arg Asp Arg Asp Pro Leu Ser Val Gly Arg Val Ile Gly Asp
1               5                   10                  15

Val Leu Asp Pro Phe Thr Lys Ser Ile Ser Leu Arg Val Thr Tyr Ser
            20                  25                  30

Ser Arg Glu Val Asn Asn Gly Cys Glu Leu Lys Pro Ser Gln Val Ala
        35                  40                  45

Asn Gln Pro Arg Val Asp Ile Gly Gly Glu Asp Leu Arg Thr Phe Tyr
    50                  55                  60

Thr Leu Val Met Val Asp Pro Asp Ala Pro Ser Pro Ser Asp Pro Ser
65                  70                  75                  80

Leu Arg Glu Tyr Leu His Trp Leu Val Thr Asp Ile Pro Ala Thr Thr
                85                  90                  95

Gly Ala Ser Phe Gly His Glu Thr Val Cys Tyr Glu Ser Pro Arg Pro
            100                 105                 110

Thr Met Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Val Tyr Asn Leu Gly Ser Pro Val Ala Ala Val Tyr
145                 150                 155                 160

Phe Asn Cys Gln Arg Glu Ser Gly Ser Gly Arg Arg Arg
                165                 170

<210> SEQ ID NO 21
<211> LENGTH: 901
<212> TYPE: DNA
<213> ORGANISM: Arabidopsis thaliana

<400> SEQUENCE: 21
aaaccgaccg gagccaacca aaccggttaa catcctaaaa ccaatcatat tttattaagt    60
tttgtgttga tgctaaacca aaaatcattg gcatgcatat ttctaaattt agtaataaac   120
aaaaacactt agaaatcaca cgttcactat actaaaaaac gttgacaaaa acacaacaac   180
tatactaata attaaagaag agaaaactga accaaacttt ttgtaaactc ctgaatttaa   240
attagtaatt gaagtaagaa gatgaagaag aacatgttaa gcaaacaaaa aaattacact   300
aaaatcatat aaaaatacat aattacaaaa gtacccataa gatggattta ttgatatggg   360
tcatctgtga acaagccac agagagacaa agactcgtaa gtattgggca acgaaagcga   420
cctcctttat tcaccactgc cattaacatg ttcttcttct ccttcttctt ctacatttta   480
tgaccgtttt acccttcaag agagagaaac aaaatcactc cctctcactc actctatctc   540
tctcttctgc aaagcttcag aactctggca gagagataaa agatgatggg gttttttaact   600 ttatcctccc caaataattc ttcttccctt catctctctc tcttacacaa caggtccta   660 catttgtaca atctcctctc tttaaagact ctctctcttt ctctctccat ctctatctta   720
ctctgtattt ctgtcgtctg agcactcaat gaaaccactg taaatttccg ccagaatttg   780
atgtgatgga acgataaaaa tcatttttc tcggttaaag taaaaaaaca aaaacaaatt   840

```
tctgtagaaa tcataataaa agaaagaaaa aaaatctaat gtcggtacat aatacggttc      900
t                                                                     901

<210> SEQ ID NO 22
<211> LENGTH: 507
<212> TYPE: DNA
<213> ORGANISM: Arabidopsis thaliana

<400> SEQUENCE: 22
aaaccgaccg gagccaacca aaccggttaa catcctaaaa ccaatcatat tttattaagt       60
tttgtgttga tgctaaacca aaaatcattg gcatgcatat ttctaaattt agtaataaac      120
aaaaacactt agaaatcaca cgttcactat actaaaaaac gttgacaaaa acacaacaac      180
tatactaata attaaagaag agaaaactga accaaacttt ttgtaaactc ctgaatttaa      240
attagtaatt gcacaacagg tccctacatt tgtacaatct cctctcttta aagactctct      300
ctctttctct ctccatctct atcttactct gtatttctgt cgtctgagca ctcaatgaaa      360
ccactgtaaa tttccgccag aatttgatgt gatggaacga taaaaatcat ttttctcgg      420 ttaaagtaaa aaaacaaaaa caaatttctg tagaaatcat aataaagaa agaaaaaaaa      480 tctaatgtcg gtacataata cggttct                                         507

<210> SEQ ID NO 23
<211> LENGTH: 2000
<212> TYPE: DNA
<213> ORGANISM: Glycine max

<400> SEQUENCE: 23
catgagcaag taagtaaaca ttttatctct gttacactcc aaacacatac actaacttaa       60
gcagagtcct ttttcggcta ttcactccat caccaaagaa tgagctcatc cataaaaaca      120
tatacatgtc aacatgtcga agatgtaga acctggtaac aataataaag aatgataatt      180 ttttatttt taaaacgaag cactaaaata gatttaatta tatttatcat ataaaattac      240
caattaatca tatatctagt gaaatgatca cttcaagtat aaaaaaagat tttatacttt      300
tcgtctttct gtatttagaa atattagcaa agtcttggat aaaaaagtgg tcgtagcctg      360
tccctgtagt ttccttgtta gtcttgatga acaagaagtt ctcagttctc cccacccat      420 tctgattcgg tttacatgga agtagtaagt aaccatacac cattatagaa ataatacgat      480
aaccacacgc catgtcttac ctcatgcgtt tactgaagtt gttttcttct tttattttc      540 tttgatggag ttatggtatt aatattcaat attagattgg aacttgcaga tcaacttcaa      600
gaggcactct tgataagga taccccaggc attgctttt gacataacgc caaaccctc      660 ctaaaaaacc cttcattttc tatctcttag ttccatttta tgcaatgaaa taaaacttct      720
caaatagtgt caaagcccga aaattgccta ccatatattt atcacgattc atgaagggta      780
tcttaattcc ttttttttt ttttcctgaa atgttttttt tgaaggaatt ttcttgaaat      840
gttttaatgc ctttttttt actcaagaaa tgtcttaatg cttgtttact tacataaagt      900
aatatcgttt gtctttttt acgcaatatt atattctagt actctgtctc tccaatctta      960
ttatttttaa aattttctt ccttcctatc ctattatgca caaaaggtg taattttaac     1020 atttttctac tagtaaaaaa cctacaaact ttttctattg ttaaaattaa atataaaagt     1080 aattatttt atttttatata aaaatacaaa gattttatgg aaaaatatgt aagatataaa     1140
aatatgatta attattttac tttcatctta acttagcaaa tactttctga tcagtgcctt     1200
```

-continued

| | |
|---|---|
| atctcgcaca atccacaaac attatctcgc acaagccaca aacacgcgct tcatgatcca | 1260 |
| aaattgtacg agcgacgctg tccatgtctc ctagaacgcg cgtagtaaga aataagtgtc | 1320 |
| cctttgattt catgttgcat agttaatttt tagtttaaga ttaattttag atagttttcc | 1380 |
| atattttaa ttttatatta aagataaagt caaaattaat gtttagaatt aattgagttt | 1440 |
| aagtcatttt aggtaccttt tggataaaga aatttaaatt aaatttaat tcaaaattaa | 1500 |
| tataaaccaa aattattaaa acataaatca tattacttta aaattaattt ttcgaaaaag | 1560 |
| cacattcaaa gctccactaa aaattgtctt tgattaatag ccgtggatga gatttgattt | 1620 |
| attagtgaga aaagacaaag aggtttaagc gcacgcgaag agaggcgcgt aagtaaatag | 1680 |
| gagaaacttt agctgtcaaa tatgctggga acggcgagt acgaatgacg gcggctacca | 1740 |
| cccttatatt acagtgacag tctcactctc acctatctag cctaacgtcg cttcaccgcc | 1800 |
| gtttcccatt cttattctct ctcttcataa cactcttcct atttacagtt cacgccaaat | 1860 |
| gcctgcactc tttctctact attaccaagc attggccaca ccaacaccaa cgaataacct | 1920 |
| ttgttattgt aactaataac cactgcattt ttcccatact cgttgatctc ttccactaag | 1980 |
| tgctgtggtt ggtgaccgca | 2000 |

<210> SEQ ID NO 24
<211> LENGTH: 2479
<212> TYPE: DNA
<213> ORGANISM: Glycine max

<400> SEQUENCE: 24

| | |
|---|---|
| ttggattgtg tagaagaaaa aaattgaaaa aaaatatgac atccatgtta atttttgaaa | 60 |
| ttttcttata ataattttcc gtcttcaacc aaaccagact cctattaagt atagtaaata | 120 |
| ctattatatt tttgtggact tcttaataaa tagtagtaat attttgaaaa gcttttttat | 180 |
| ttttacgaaa gtcataataa attataaaca aacttataaa aaatattaaa tcttatagta | 240 |
| ctacttttat ataataataa taataataat aataataa taaaacgtgt | 300 |
| tcaaaattat taatattcct cttgaagttc cgtttcatat tctgtaaaaa aaagttgcgt | 360 |
| ttgatattaa aatataacag tactaaaaaa acaacataaa aaagaaaatc atgtttgatg | 420 |
| aaagaaaata caaatatatt ttcataaaga gaacttcaca attactcgca atgctgtgtg | 480 |
| aaatagggat ataaccttta tccaagacac gttcccatca ttgaagtata attaaatctt | 540 |
| ttacggttaa ttataatgaa atcattttgg atttgctttt gcctattatc acttttcaca | 600 |
| cgatgatact taattattca tagaccttt tgtcgagtaa gagggaaat gctaaacttt | 660 |
| tctgcttaga ttttttggca tagttaatgg attttagcct ttttcttct tattaattt | 720 |
| tttctttcat aagcatagtc ccggtaaaat tctcactttc agttgatact ttacctcctc | 780 |
| cgaaaagttt cccatattag agactcaatg gcgtataaaa tcatcttaaa catttactta | 840 |
| taatgaatgg aaataaaatc taaaagtta gctactaatt cttcacggc cattacgaag | 900 |
| actttgctta aaatggaa aaaagcaaaa tataaagag tgtacattgt ctatttttat | 960 |
| aattgacttg gctctgtatg tattatgtaa ttaattttta atcttatatt ttgattattt | 1020 |
| atagagatat aaaatgaatt tgatagttaa agaagaaaa gaagagatga aaaattgtgt | 1080 |
| gttcgatcct ctaataaaac taacatttta ataaattaat atttatcatt tttttaatta | 1140 |
| tttgagtttt ggaagtgtaa tgagtcgagt aatttttattt gatggttgtt tggttcactt | 1200 |
| atctatgttg atcaagtaat cgatcaattt atctccatga ataatgatga tttttaagaa | 1260 |
| tatttaacat ttgaccatca attccttaaa tcatgtaatt attttgtca accatgcaac | 1320 |

```
ctctataaat ataggtccta catatgtttg acattcatca tagtgtgtaa tgtattttt    1380 ttattaaaaa aaacagagat gatgaactcg tgataaagaa tcacctaaca cattactgat    1440
actctctata aatatcacat gacaaccttt aacaaatacg cacaattcat atatcaatat    1500
ccattacttt gtcatattct aatttgagtg taaaagtctt tattattaca gtcttttaag    1560
ttggtttaga gcaatttgag ttaatatctt tatacaaaaa taacttaatt ttttaatatt    1620 attttttaaga catatttctc ataaaaaatc acataattta gttataatt tttaatttaa    1680 tattatcttc attttttattt ataaaattta attacctaat tcatcaatat taaaaaaata    1740
aattaattta attaatatca ataaatttat cctaaactta taaacattat cattaatgct    1800
cttctctctt aaatgtttat ggatataact tcttttattt aattaaaatg tttattttaa    1860 attaaaattaa tgtaagaaat aatacaaatt gaatattgta taaaggaaca aacataattt    1920
tgttttgtat tagaccataa gtaatactcc atattagatt atatatataa cttttatttt    1980
aaaattatag agtatacttt ttttagagga aattatagag caaactacat tcatatgatt    2040
tctcttttat aaatattgaa aacaaaatag ggatatgcaa cagcaaacga gggaggtttg    2100
aggagagagg gagagagaga gaatgtaggc gcgtgtggca cagttatgag ttaagactta    2160
ggagaagtac acattggcat aggcattgtt attggattat gtgtagagtc cgatagacta    2220
gaatgacggc tactagttac tactctctct cttcataaac acaccattta tgttttccc     2280 ttcccttcac gccaaacgcc tgcactctac actctactct ctcgtgctct gtgactactg    2340
tcactctctc ataaaccaaa catgccctta atccattttc catagtagtt agtgttgtta    2400
ctcatctctt ccatcttcaa tctctcttct ttccttattg ttgctcacca aggtgggtt     2460 ttttgtacgt gtggtggca                                                 2479

<210> SEQ ID NO 25
<211> LENGTH: 2000
<212> TYPE: DNA
<213> ORGANISM: Glycine max

<400> SEQUENCE: 25
cattaaataa ttctaaaaaa gatataaatt tttgtataca aatctatatt taagaaactt      60
ttaatctaga tgtcgatttt aaaaaatatt atttaattaa aaaatattag atggtgtaat     120
aattaatcaa aattatatca agataatctg attcctttct atacacacat aatattattt    180
catccttagt ccctaatatt ttcaattctc attttgttac cagacttgta ccgaacaaaa    240
acaaaatatc taatcatagt tttcattcaa caaaaatgat ttttaactca atttgaaaca    300
cttttcattc atttttaaaa ctaagaaaaa atttgtgatt tattttata atttttgaaaa    360 acattctacc atcattatta ttgtttctac taccatcatt attaatgtta ctactatcac    420
cttcctagtt ataaccgtaa gcattatata ttttattat tattgttatt atgttatttt     480
gttaatatat ttatttttgt tctaaaaaat tattattttt tcatatcttt cactattttt    540
gttattattt tagcaagttt gattattttt tattttaaat attttatgt gtcacttttt    600 atatcacatt atttaacagt gtgaatcgat aaaaaatata ataattatct ttaatttgta    660 agaattttt caaaattaaa actgattta gttcttgaaa aatgtaaaac taaaaatgaa    720
aaccacctaa cggggcctta gtaattagga catggtctcc ctggttaccc acgggatttt    780
ttcacatcaa agaagacctg gtattttcat tttcatgaga tttttgcata tcgaacaagg    840
cattaagaca gggggttgtca ttgtcgtgat agtataattt acatggtcga agtgatagaa    900
```

| | |
|---|---|
| actttaacca tcatttacct tgtaccttac tataacacaa atactacga tttccaaaca | 960 |
| ctagatcgcg cgcttatgtt ttcagacaca ttattcttct tcattcataa ataaatttgc | 1020 |
| agctagtata tgataattgt accaatttat gtaagttttt tacaaaggac attcttatct | 1080 |
| caataaaaaa ctaaatgttt aaaatattct ctagcacatt ttttaaatac attttgtcta | 1140 |
| attaattaaa attaaaagag gatataaaaa atatgctgct aacatcttga acatttccgc | 1200 |
| aatcaataat ttctcaatct atctgaatat ttttgcaact gtatacaaaa atctcagaac | 1260 |
| agaaaattat tgattaaact ggaagaattt aataacattt gattcacgtt tgtttagtga | 1320 |
| ttaaaaaatc ataacattac actatctaac aaatgcagca tccataacta ccaaacatta | 1380 |
| aacaagagaa acagacaaag tccaataatc acagagacac gcagtgacaa agaaaagaaa | 1440 |
| gagggaacgg taaagagaaa ggtgtctctg tcatctcaaa tagattgcca taactccctc | 1500 |
| cttctctctc acaagctctt gcagagtgaa agcgaccact ttccgatctc aattaaaagt | 1560 |
| atggcataat ttgcaatggc ggaactgaac gaataataat aagagatacc atagttaaga | 1620 |
| gagagaaaca caaacatgga aaaagctggg cctcactccc tgggtacaca tagatagaga | 1680 |
| ctatggtgca gtgttgcagg ttgtagcaga agctctgcca aatagtgtta actttattcg | 1740 |
| agaaaattat tattattatt attattatta ttattctctc tctctagtct attatcagtg | 1800 |
| gtaattcagt aatgttgttg cattatagag agagcgtggt ctatgtgcca gggtgatgtg | 1860 |
| atgtcatttc actaccttca aagccagaaa atgcaacag aaaaagcttt catcccatca | 1920 |
| catcatttga accatgaatc atgaactagt tttctaaact aaaactataa caacaccttc | 1980 |
| ggttgttgtt gttgttggct | 2000 |

<210> SEQ ID NO 26
<211> LENGTH: 2000
<212> TYPE: DNA
<213> ORGANISM: Glycine max

<400> SEQUENCE: 26

| | |
|---|---|
| aacatttaag atcttaaaga tgccaagagc ttcatatgaa aatgtacaaa agagatttta | 60 |
| aaggcaatat caatgctgtg acgccatatt aaaataaaag ggatggtttc tcctgtatat | 120 |
| tgagcaattt gtattactta tatacacaaa atctaaattg attcttaaca aatatgtaaa | 180 |
| gaaattaata atatgatcaa gttacctgaa gaagctaaaa taaaatagaa attaagtaa | 240 |
| aagaaatgag gagtagaata taagataaca tcaaaaaatt atttcagcat attttaagaa | 300 |
| catcaaattt acctttcatc aaaattaatc ttaaagact aaaacattta attaagttta | 360 |
| taaatactca cacaaaatat taatttattt tgtaattatt attttttata tttttattta | 420 |
| ctattgcctc aaaatttgca ctaaacaaga gaccctagag atttcgttag aacaataata | 480 |
| gacacggtat taaataatta aattaatacg aggatgcata actaccaaac aaatgcgata | 540 |
| aataaatgag acgacgagag agcacaacgc gggaatgaga taattaagaa aaaaaatcta | 600 |
| ataaattagg aaaaaaaaga cataatatca taagcttgaa tccaatgtac aaagagaggt | 660 |
| tggcaataaa gagaaagaga aaagacgtcc ctgtcacctc aaatggattg cattactcat | 720 |
| tgaaaaggac attattactt ccgacttttt atattaactt actaattata aaatatataa | 780 |
| aaaaatactt caaagatgca tatatttat tttattacat aattacataa cagaataata | 840 |
| taaataatg taactacaca ttaaaacatt aaaatagtga ttggagtagt ggtataagag | 900 |
| gacgttgaat tcacgcggaa gagaaggata tatttcatgt ttaatttgtt gtcatgccta | 960 |
| gttcaatgta atctaataag taaaaataaa atacaaacaa aataaagatt ttggttcctt | 1020 |

```
aacaaaagta cttttacttt aaatatatat ttttatctgg ttttaaaaca tgcacatatt        1080
taacataaaa gttcatatta aacttttttcc tacatacttg gatcaaatag tcacgtattg        1140
caggtaaaaa ataatagtgt agcttataga aatcgtagaa ataagtctat aaaccagaag        1200
aaaaaaaaca ttaaaataat agtatagaaa tctatatcag tgtccccagt tcttacattc        1260
atgacccatt tccccataaa ctctttgcag ataatgcaat ggcaaaacca cacagaaagt        1320 gaccctggg aatcaaaagt taaaccaat ggcacagcat agcacagtgt acagtgttta         1380
tttactatat agcaaaacac tcactggcat aacactttag ggagagagag agtgaaaaca        1440
agtgtaaaaa gagagaaagt taggaggggg atagagagtg tgtgtgtgtg cagagtttgc        1500
aggcttgtag cagaaatggt ggcagatggt tttaacttta tgtgtgaaat aattttcttc        1560
tatctctttt ctctttagtg ttttctctct ctctctctct cttctttttc ttcctgcatc        1620
ttcttgtgtt tagggagtgt gatgttttgt ggcagaagaa cgatgtgatt ggacacagcc        1680
aaagctgtgg acttgttctg ttactacttt gtaattgtaa tcacataaaa ggctagaggg        1740
tatgaagagt gcacagaaaa atactagtac tagtttcaaa caaaactcac cttactacta        1800
cccttccatc tcaagccata gttgagttga gtggtgcaca gtgtcactat acataccact        1860
aacacccttt tttggttctt gttctgtggc tccttgtgct ttgagcaaga gcttttttgag       1920 aaagagcttg gtggtggtgg ttgttgttga gtggtttcat ggttaggctg ttgttaagtt        1980
gaagttcatc agttgcagct                                                    2000

<210> SEQ ID NO 27
<211> LENGTH: 1399
<212> TYPE: DNA
<213> ORGANISM: Solanum tuberosum

<400> SEQUENCE: 27
aacgaaaaat ttagaaacta ttagtgatcc aaatgttcgt gattacctgc aacgagaaca          60
acaacgaata cttgaaaaaa gaaatcgaca atcacaacca caaccataat cgcaacaatt         120
ctcagaatca tatcctaatt tttttttcgaa tagtgctaaa tttgaaaacg acctaccgaa        180
tttctaaatt attgttgtga tcaattaatt attatgttat gtattgtatt ttatcttgta         240
tttaaattat tatgttatgt attgtattgt tatcttgtat ttaaattatc atatcatgta         300
ttgtattttt aaattaattt ttttttgcata ttctttataa tgaaaattaa taataaaaca        360
attttattat tcacgaaaat tagaaaaaaa gttaaaatac tattaatttg aaattaaaat        420
agtatatatt aaataatatt tttaaaaata ttatattata tttaaaaaga attatgaata        480 ttagatatt aattaatgga attatatgta aaataatatg ttaattagaa agtaatagaa        540
aaataataaa ataatgaaaa agtagaaata gagagtgtga atagtagaat ttggagaact        600
attcaactct ctaaatttga agaatatagg gtgatttgga ggtgggttgg agtgtccatt        660
ctctatttta ctctcaaaat atagagaatg gagagaaaaa tagaggtgga ttggagatgg        720
tcttagtgac atttttgatt ccgccaatgc tcagttggcg tagtcgctgt caaacttgag        780
aaaggattac ccctttaggc ttgcacagac agtgacttat gatgaaatga agccagagaa        840
ggcactctgt tataacactt aaatgaaaat acatgtgtat ggactagcaa taaaagggc         900 actagtaatt ttagtaattg aaaagcaagt gtatagagag agataatgag agagaaagag        960
taagtacact actactgcta ctatcccata tagctgtaat gttgcaggtc tgattttgc        1020 agttgcagac ccccttcttg gcacaagctc ttttaacttt tatcttctca aataattctc        1080
```

| | |
|---|---|
| tctctctctc tctctcttttt ttctcttttt acattgtgag gaaactgaat acccattgta | 1140 |
| tgtattagtg tgaggcctat ctgccacaag gatgtgatgg aacactatgc ttcctctgct | 1200 |
| aaaaccccac aaccccaaaa ctcttttttca cttcacattt aatcacaatt cctcagtgaa | 1260 |
| attattctgt tgctctctct aatttcaatt tcaatgtcgg taagtccaag aactggtttt | 1320 |
| tcaattcaaa ggagctgagt tagtgcaaac acttgaggtt ttgagttttg acagagactt | 1380 |
| gagtctcaga gaaactacc | 1399 |

<210> SEQ ID NO 28
<211> LENGTH: 2000
<212> TYPE: DNA
<213> ORGANISM: Solanum tuberosum

<400> SEQUENCE: 28

| | |
|---|---|
| accttatata agttacaatt tagttatgta tataagttaa aattaaatta aaagacattt | 60 |
| cgaaataata tgattatacc atttcgaaat taattagaga gagaaataag atctcgcaaa | 120 |
| attaagtgtc ttcttgaaat taagaaccat ttttaggaga taattatgta ttttttcatt | 180 |
| tttaatttga cacgtatgca tatccactat tttgttttat tccaaagtga cccctacttc | 240 |
| ttttggtaat ttctttgagt attttaaact ctagtccccc tttctcaagc aaaaaggctc | 300 |
| actcgcgcac gcgcgaagag acattgtgac gcgctggatg gaaaatccag aagcgtaact | 360 |
| gtcaaaaaat agaacaactt tgggaaacgg ggtgacggcc gctgccacca cttttttcat | 420 |
| ttccaaacac tcattaacta acgtcgtttc accgccgttt actgcttaat gagtatgaat | 480 |
| tacactctaa tagtctatttt ttacttattt ttaatgtgtt tatcaaatta tattttttaaa | 540 |
| tataatactt taaaaatatt atcatcaata ataagagtaa attaaaaaat aaatgacaaa | 600 |
| ttgtttctta aattgttaaa ttaaacaatt aaaactgaat atttacaaaa tacctcttaa | 660 |
| cttgctaaat taaacaattg aaactatatt tatattaata aattgaactg acaaaaataa | 720 |
| ataaaggaac tatatatttt ctcaattata tcttttttact aaaatattat ttttctaata | 780 |
| ctagttaaac ttttaaaaaa catctaataa agaaaaagaa tttgttcaat tatactttag | 840 |
| aagcttttat tattattatt attattagta gtagtagtag tagtaataaa ttagattaaa | 900 |
| ttaaagagag aagtattcaa aactcccaaa actattgtat tagttttatt tcagaactat | 960 |
| tgacaatctt aatttttttt ttttttaattt gactaggtga acttaaatat acttcatttt | 1020 |
| ttgcaaaaca agtgaagtac actcttaaat tttcatcaag tttagaaatg ttttcaacaa | 1080 |
| tttactagac tctttattaa gaacttcatg ttcctttcaag agtttatgag cacttgctat | 1140 |
| gtcatgttac agatcaagaa tatctacaga gtgtatctaa atttagtact agtaaagtag | 1200 |
| aaaatgtatt acttatctct caaacaatag gtattcatta tactattttg agatgtccaa | 1260 |
| caatttttttt tcactttatg aaatcaatga ataatttaac acttagttcc taattcccag | 1320 |
| taagcattaa ttatagttat ttacttatta tattttttcaa cacattatat tgaaaaagtg | 1380 |
| atatagtaaa tctatctttt tattttattta tttcttaaaa tttgtacaaa cttaataata | 1440 |
| gacaaatatt gttgaatagg aataataatt tacattaaat ccaatatatt tttcaatagt | 1500 |
| tgtcactaaa tgaaaatact tcatctgttt caatttatgt gatagttttc attttttcaaa | 1560 |
| agtcagacaa ttatatattt ataaattaag taaaaaatat tataagtcac actaattaac | 1620 |
| aattcgaaat attcggtacg gaggaactaa cacttatgtt tttagaccat attagtcttt | 1680 |
| tctctctatt tattatataa tattgagagg agagtgcaac caccatggca actttctctg | 1740 |
| tcttcataaa acgcagctga cattaaaaaac acagacacac acttcgcatt tcatatccct | 1800 |

```
ctcactacac gccaaatgcc tgctcttcct atttctcttc ttcttctttt tcttcttctc    1860
tctcattcac ataacacaca ttcttgtact aactctgcat cataaactct accccacttt    1920
cttcttcttc tccggtcata ttgctctgaa actccactta ttgctctctc ccggcattta    1980
tttttagttt ctcagaaata                                                2000

<210> SEQ ID NO 29
<211> LENGTH: 471
<212> TYPE: DNA
<213> ORGANISM: Arabidopsis thaliana

<400> SEQUENCE: 29
taataagaga cgaaaaaaaa ataactaact gatcattacc atccataaat aaatagttgc      60
tgccataaac caaacacatt gtgcttatca aaagaagaa atttgtactt aatgaaacat     120
tcattattag caaagtgtaa aaccaaagaa aaacaaactt tatttctcat tttattagta     180
aaagtgaaga agagtaaaga aaagagaga ctgagatgag gctgagagcc tgagtctgcg     240
ggtggagaga gagagaaaga aagcctcttt acacgtgatt tttaaaagag accaaaaccc     300
caaaagcaaa cctcttttgc atgcgtcctt aaaagacata aatttctctc aaaattttct     360
acatcacaaa atcaatcttt ttctcttctt cttcgtcttc atcatcatca tcatcatctt     420
cctctttctc ttcctactga gatattttct ccacattgag aggaaagcta t             471

<210> SEQ ID NO 30
<211> LENGTH: 1231
<212> TYPE: DNA
<213> ORGANISM: Arabidopsis thaliana

<400> SEQUENCE: 30
aggataaatt tcatctatta agatatcagt caattataat gtgttacgtg attcgataaa      60
aaaaaaagac caaaaaaaaa aagaagataa ctattggtaa gcgtaagaaa tgtgtttaca     120
ttttggcatt ttgccaaaac acataaagat ggttagtgat gagacgagac gagtcatgcg     180
ctacttttaa aacaaaatga aaacatcat taagctaaca aaccaaacac acttgttttg     240
ataacatgtt ctagggaact agttatgcca aatctaatcc gcataagaag actaagtcac     300
aacataattc agtaatttgg ttgagattaa atcctataaa tatgatttta aggtataaga     360
gagaagagac tcttttgatc aacacaatca acatctaca aagaaaatta tctcacatag     420
ctacttctta atctaatttt ttcattaatc cattttattt taaatgtgaa gaatcgcatc     480
tagatgtgac ctctcatgat aaaaaattaa accattgtaa aaaaaatgtt gtgtaaaact     540
aaatataata aattattaaa aaaatacaaa ttcaatccac taggttaaaa actcctatgt     600
agaacatttt tttatattaa aatgtaaata catgaatctt ttttttcgaa aaactaaaga     660 catcttttt ttatatatta attaccaaaa caaaataaga cgacaaaaat attctttgat     720
atagtaaaag aaaactagaa aactagaaaa caataaatta ccaaaacaat ctagaaaaca     780
ataaatccta ctttgcatta ctttattata aaatcccgaa atgaatctat aaatgtagaa     840
aatattatac aaaagttgta agagatttta atatacataa ttacatatat atacaagtaa     900
atacaccgta tatacatacg aaggagtaaa cagtattatt tggtatatag ttacgtctct     960
atatacgaag ggttcaaact tcaaagtaat aatttaatca acaatgtgta catattgata    1020
agtagtagta tatatgtaaa ggtctcacgt ctctataata aagtatgact cgtcacgtga    1080
cctcctcttc ttcgcagaga cagagatagg atgagacaga aagaaaccaa caaaaccaaa    1140
```

```
cccaaaacc caagaaaaag agaaaaacac tctcttctct tctctctctc tctttctatt    1200
taagagactt cactgtctct ctcagtcttt t                                  1231
```

<210> SEQ ID NO 31
<211> LENGTH: 1548
<212> TYPE: DNA
<213> ORGANISM: Arabidopsis thaliana

<400> SEQUENCE: 31

```
ttcacgtgtt tatttattta tttgggttat taaacataaa tcatgtaaat ctgaatcctg     60
tggagatctc tccctagttg atgaatagat atgatgaatt taattctttc atgaaataaa    120
aatatatgaa acatatgtag cagaaaaaga agcatatcta tgaaacaaca acattcaaa     180 aaaaaaagga aaacggaaaa ttattaatat gaaaactacg gctttgactt gtagctgact    240
acatttacga catatatata taaatggacc ccactgagtg tctgcaaggt ctttacacaa    300
cagtatcttc ttctgtttct ttgactcttt gtgatcccta agcctaccca taatacgtgt    360
ctacatttta ttggattgtt tcgtgactct gtaatctttt ttataagaaa acaagtaata    420
gtgaaattga agtaaatagc tcagcacaga aacttcgaca aaaataactc acagattaga    480
aaagaaaata tatgcataaa tagccatggt tcatttatga acaatttatt cgtttttta     540 gtttataatt tcattaaaac atgtttgtca catcacattt catgtccttc ggctcctact    600
acaacaacaa gtcactgtca tctccattac ttccacttct gctccttct  ttattaactt    660 gttcaaaaac aattctaaga taaataacaa taaatgttgg tctctcttta ttatttcccg    720
gctaaagaag gaggatgtct cgtattatcc gccatcaatg ctcttttgtt tcctgtttct    780
tgcaatttga atccctgaga atcctagccc acttatttac tactttgcct tagctgtttt    840
cgacatcaaa attttggtca tatgactcat atcaatcttc aaatttgata aaatatgttc    900
ccaattcaca aaaacaaaaa agtttcgaa  agctcaaaaa cctttaccat ttcaatagta    960
gataggattc ttttagattt gcatttcacg aaaagagaag aaaaaaaatc gaaaatatt    1020 tgcaatcatg atttttttgtt tctgaaggag acctgtagtt gctgtcatga acattaaata    1080
caaatctaat aaatgttgta cgaattttgc gtgtaataaa tggtcagggc cggctcgaag    1140
ctcgctgatc gtccttttt  cgtgtctcta tagcaacaca caatcgtatt tatttcaaac    1200 ttttttact  ttgtttccca tccatcaaat ataagtataa aaatgtaaag aatcatcata    1260
tatagatcgt aaattcattg cttcctttgg cttttatt   catctagacg acgttaaaac    1320
cagaccagac caaatacatt tatcattttt cccttttttc taaaattctc tctttgattc    1380
ctatcttctt ctctttatt  tcactttgtg ctttctctgt ctctcctatt atgagtctaa    1440
aagtctacta gctgttcaat agttttgtct ttctgtgttt cttcttcttc aaaaccgaaa    1500
gaaattcaaa aagagtcttt cgctgcttgt tagtggggtg aggaacaa                 1548
```

<210> SEQ ID NO 32
<211> LENGTH: 440
<212> TYPE: DNA
<213> ORGANISM: Arabidopsis thaliana

<400> SEQUENCE: 32

```
aaacccgaac ccgaaccaaa cccgaaccaa aatcttaaat tacccgaatg ggtcttaaat     60
ttctaaatcc gaaaacccg  aacccaaaat acccaacccg aatctgaccc gaatatccga    120
acgcctaatt tttctatgtt aatgaaatca attatatgac atgtttataa agagaaataa    180
attacggtga gaattaagcc catttacgtt acggaaataa aacacccatt taaaaaagcc    240
```

```
caacacgtga agcccatttc cgagtgcgtc ccacatttac tccaacggtc gaatcgactc    300
aaacattcaa aatacaaaaa cgctatcttt atcgtcttcc tctgtctctc tctcacaaca    360
cataacgttc aaatcctctc tctctctatc tcgtctctta tctctagatc taaaaatctc    420
ttctttcctc aatctctgtt                                                440
```

<210> SEQ ID NO 33
<211> LENGTH: 317
<212> TYPE: DNA
<213> ORGANISM: Arabidopsis thaliana

<400> SEQUENCE: 33

```
acagacattt acttatacgg ttattgaggt tgaactggac cggagtagca ataaattatc     60
ggttcagttt gggagatcaa accgttaaaa agaaaataat ttgaaatggc cacgcagaat    120
acgagggtct gaggattgta cctcctttct ctgcaaaaac ttaaacgttg atttgactca    180
agcgtcaagg taaggtactc tctcttcata caacatttta gctttacttt ttctctttac    240
tcttctctct ctctttctct ttctctttct ctttcactcg ttctctctca ctcactctct    300
tcacacacag atccaag                                                   317
```

<210> SEQ ID NO 34
<211> LENGTH: 3912
<212> TYPE: DNA
<213> ORGANISM: Arabidopsis thaliana

<400> SEQUENCE: 34

```
acaccaataa aaatacacag caataaaatc gctacgtata tatatatata atatgtatta     60
tctattacaa gatagtaata gagtatagca agttgtatca tctaacaaac tatgcgaata    120
aaatttgaac attgtgacat gtagatgtag tgtaatttag ctaagtgctt atcatcagta    180
acatagaccg acttaacttt ttacgaaaaa aaaaagtaa catagaccga aaaaatgcat    240
atcgtaaatt taatggaaaa cacaatttac gataagtaaa aaacaaaaag aaattacgat    300
aagtcgagaa aaatgcaaca aattgagata agtattgat aaaaccatga agtgtcggc    360 gtatgtaaat gcggtgatta atgtgatcat tagagcgtgt gtgttaaacg cggcggtttt    420
agtggagatt gatcagctga taacactctt accgggacga atctaattcc atattcatgg    480
cttgttaaaa cctaagacat acgcaatctc taatttgcta gtatagttag ttctatatta    540
tttttcgact aataatgtaa acatatgatt attaagtcgc aaaaagagtg cttaacaacc    600
aaaaagtgga ttaattaact tggtgggaaa agttacaaaa cctttaatga ttactctttg    660
taccaagaat agtggcgaag cactataaga gcagagaaaa gaagctcaat aatgtactaa    720
aagttgtaga ttttacagc ttaaatacac caaaattaat agaaagttg gtaattttt    780 aattcatggc tactgattta gattttagaa acaatagta gtatcattgt cacatcttaa    840
acacacaata ggtatgtttt aaatcaaagg ccgtagttaa tttgtcaaaa atgtatgcat    900
ttggtatttg gatgtctccg aaaggatgga tatatggact tgttagataa tttcatacct    960
cagtatcaat agtcatggag cccaaattgc tcaaaaacat atttttaatt ccaagacttt   1020
gatgaagacg taataatgag tccaatgggc catcagatac aatgttcgga atttaacggg   1080
tttgttagtt ataagtattg ggcttgacct atctggttca atgatatgta ggaacaaccc   1140
aatttgcaaa gctttattaa aagactcttt agttgtcgtc aaggtttaac ttgtagtagt   1200
tggtaagaaa ttctacgtga aataggcaac attacaaaaa caaaaatcaa ttcgaaatca   1260
```

```
tacaaaacga aaccaagtag taaccaacta cactattatg acattaatga ttagacattc   1320
ccaaatcata caagttcctg tcatgaagga acaatggtc cgtatttgca acgattaca    1380 aaaattcaaa ccaaaaatga aaaaacgagt taaattattt ggtttataaa aatagtaatg   1440
tcaacagaag actagattgg gaaacctgaa gcgaacagag cttttaaaaa cgagtttgaa   1500
cggctgggat catttggtac aatacccacc gtaagtttgt ttaccctagg gatgcaagcc   1560
aaaggcccaa atcagttact acttactgct acaaccatcg tctcagcttt ttgtctcagc   1620
tttttactaa tgaagcatac aatttcttgg gcatgtcaca tctcgacacg tgtccactat   1680
tctcttctct tattggctac tcgttcgtag gcttctgtta atagatgatc tctctataac   1740
tctaacagtc ttttctttct ctttatttcg ttttggtatt ttaagtttca aattgaaaat   1800
aataggagga aaagtctagt tttaaatatt gttttttttac aagtgaacgt gaaccaattt   1860
acctcttttt ttttatatat cctatcggct aatctggtta gtatcggtag aaatgcaccg   1920
aggtgctaca gagattaatg ctagggatag tcagaccgct tgtatttctg actatcaagt   1980
aaatctacgc ccaactcaca tatttcccaa acaaatgtga ttttttttttt ttttttttttt   2040 tttttttttt ttttgtaaca aatgtgattt tgttttcaag gaaaatagaa cttacgtttg   2100
ggaatttcac ccttcactaa agcttccttc tgccattaga ccacaaaggc ttgggcaatt   2160
taccattttt gtaaaagtag aaaacaaaat gcctaaaatg ttcatacttc attacatcaa   2220
caaggttatg cccacgatat agaggcatgt aacatttata tatatagtgg aagaagccta   2280
cgagctttat taataagtat aaactctgat tattaggtaa ataaattact taaaacgatt   2340
actcaactga caaaaccgta gttgaataat aaggttacta tgaataccga ttgaatattg   2400
caaagccgga attgaaaaat atataacaga tcaaatgttc aagtgtggtc ataattctca   2460
cataggtcat atagctgaac ccatgcatct atttactagt ctatagaaag tactagagac   2520
gcatacagct gaacctactc tattcttta ttaattttgg ttctcgtgga tacaaaattc   2580
ctccaacatt tattagaacg aataaaaacca atatgatgat gattagttat tggtaaacat   2640
ataaacgttg agtaaacttc aaaatagatt gaagtactat taagacttgc atttttttccc   2700 cttgggttat attcttgaat cgtttcgaag tattttaact ttcaagaata gaaggttcct   2760
caactataaa caattacatt aatcaaaacc atttctatgt aaacaacata atttttgtat   2820
attttagtct tccccaaaag tttgaccgat agggcggttt agaccgtata gtacgactgt   2880
acaacaaaaa ggactctgga gacctaaaga tccaaaacta tgcaaaataa agatacggtc   2940
ggaccaattt aatctaacaa aaccaaatcc ttatactaaa ctatttaccg atacatttcc   3000
atataacaca gtacacacaa ttaaatcaaa cattattgga agaacaagat agaatattgg   3060
cttaatctcg aacgattaga gttatcctag agcctcggag cttttgtcac atataatata   3120
aactatggta tatataaaca tgactctcat ttgtatttat cgcaaggtac aattccacca   3180
atttttttcg tcccactcat acagctttaa ttgtgaaatc aatccataaa aaccaacat   3240 gtgacatggt ctctataact ataactataa gatagtaaaa aattcacatc aacataaaag   3300 aaaccaatc atattggcta aaaaaaacta acggtcgaaa aacgtataac cacaaaacca   3360
aaccggtcca accggtgtcc ccaatcacta tcaaagcatt aactaacttt cacaaggaaa   3420
agcatagttc agtttctcta catcgcttcc catcctctta accctgttta ctcgaatcat   3480
ccaccgttgg atcaaacacg cgctacaaat ctagcgcgtg accgaggttt ttacacagtg   3540
gaatattacc atgcattgga aagcggcgtc tacaacaaac ggcgggtcat gtcaccgtca   3600 aaatcaaccct ttcttaattc ctaacgccgt tacttatctc cgtttactaa aaatgttaat   3660
```

| | |
|---|---:|
| gcgtgtgaga gtgaagatca tatactaatt agaagtggct aatgttttaa cgtgacatta | 3720 |
| ttatcatagt taatggttcg atcagagttt aagtagtaa atgatataag tgtgtgtata | 3780 |
| taattgcata catatatact ctcacactct gacagatttg tcgtggtctt agtattctct | 3840 |
| ttcatggcta gttatatagg gctctagtac attatctctc tctccccatt tctctgtctc | 3900 |
| tctcttcttt aa | 3912 |

<210> SEQ ID NO 35
<211> LENGTH: 2000
<212> TYPE: DNA
<213> ORGANISM: Arabidopsis thaliana

<400> SEQUENCE: 35

| | |
|---|---:|
| atctttatgg tcaccgagtc tactgatata attttactgt cgcagtttgt ttccactact | 60 |
| taagtttcta taatttcaca gtttgaaaga aaaattactg gttattcagc taaattacaa | 120 |
| agattagttt aattagttta gccagtataa tgttttagta aagtattaaa cggcattttt | 180 |
| cgttgggaga attatgttat ggtataatct actaatacat acttttacac atatatcaaa | 240 |
| aagtttgacc atagtaggta gtacaacata gaagaatcaa gatcggaacc agcaaggaag | 300 |
| aagatacggt cggtccatat aagctaaga ggaccaacgt aactcgatat atattttct | 360 |
| gttctctacg ttaccaccat ataaatttta atattgaaaa aatcatcttt tggcattgtg | 420 |
| tttgatgtcg gattcggaat atggaaagag gagagatatg agattttggc acaaaggaag | 480 |
| ctgccaaagc attagggcaa ccgagtagta acgagatcaa acatcgtttc aatcggacgg | 540 |
| tcgggggtttg accaatattt ctcggatatc ttttggaccc tacgttctga cttgaacttg | 600 |
| atcagtcact tcagtacctt agttttcatt ttcaatgtga tcatgagttt ttttttacat | 660 |
| gttagcttca aaacaaatac taatattcat taactatgga tcggcatagt tttcatgtaa | 720 |
| tcagctgagc gtttatcata ttgattgaag ctaacatgta aaattctcat gatcacattg | 780 |
| acttttgcct acaaatttta aaagagtata caaataattg cttaatgaag atagcttcca | 840 |
| tagagaaaga gtaacagctt tatacggagg catagcttta gacacgatct ctgctcttgt | 900 |
| gttttttgtt taacactgaa tccacagtga aattactgct cattttttttt catttttat | 960 |
| tacattttt tttttacttt tttatttatt acaatctaca gttctaccaa cttattcaac | 1020 |
| ctagtggtac catatcgacc ccaaaattaa tcaatctaat tacaaggtag aaatagaaag | 1080 |
| attttatcaa aggagacaac tctgatcgat aatatgttgc aataaaacca tgaaaaactg | 1140 |
| taaaaaatat tgaaagctga agaaaaattt tcaaatcgat aaaaggatag tactaaacca | 1200 |
| atccggtttg tggcatcttt ttcacccaat cactatcaaa gcattaacta aaaatcacaa | 1260 |
| ggaagagcat aatttgattc tctacatcgc agtccacgat aggatttctc tatccaccgt | 1320 |
| tggatcaaat ttaataatga tgcacgcgcg cgtcaacggg attttaccca gcaaaggaat | 1380 |
| gtcttttcac cggactctta aaagacgttc ttctttttc accttgcat tggaaaacgg | 1440 |
| cgtttcttct tagaaccgtc gccgtcaaat catacggcct aataaatctc cgtttaacgc | 1500 |
| cgttacttta ccgttaagta ctaaaaaaac aaaaaaaaat catttcgatc actgtctcat | 1560 |
| taagatgatc ggagatgttt tagcagggtt taacaagtga tgatagtaat gtatgtatat | 1620 |
| atgttactga cattattttg tcgttgtcta ataggagggt actaaagttt ctctctctca | 1680 |
| tggcgtcgga gctcagcctc tagtaatgta gactgtcctc tctttctctc tctcttcttt | 1740 |
| aaacatctct gctctgtttt ccttccagtt cacgctaatc tcctgtgtcg gtcccctctc | 1800 |

```
tcttttccctt tggtctctcc caacaatggc agaacgactt tgtacccttc ttttgctctt      1860
tgtttgaatt tcgtttcttg ctacaaagct tcaaaggatc tgacttttcc ctaaacagaa      1920
aaagaggtct ttaaccaaaa aaggttgtta cttgttttct gggtttcgtg gtgttactct      1980
tgaggaagaa gaagaagaag                                                  2000
```

<210> SEQ ID NO 36
<211> LENGTH: 1470
<212> TYPE: DNA
<213> ORGANISM: Arabidopsis thaliana

<400> SEQUENCE: 36

```
ctacctaata taactagcta gggatttcta ctcttgtttt cataatcgat ctacggacat        60
ttctcggaac gtggtcaaga ttcatgagtc ttctgttttt tatgtctctg ttcaatttgg       120
tttagagatt agtatgctta tttgtttatt tcatatatgg ttatgagagg agaggctaat       180
ggcatatact ctgatgtttg tgatggctgc taatatcgtt gaggagttat tcacgttgtt       240
tcatgcgcaa aaatcaacag aaaaaattct gattatgagc caactctgtg aacccttata       300
gtgcgcccag aggtttgcga ggcaaaatcc cgatgaacca aaggaatttt tagatctcta       360
tcaacaataa ctatgatgga gctcgtttaa attcatcaca gcgacaacat cattaggctg       420
cccaacgtct atgtctcctg gaggtgatgg tacttgatct ctcaaccaat tttcttgaaa       480
atatcatgcc ttgtgagcgc tttcatattg cgcctaaaat acccaatacg caatgaacct       540
acttccaaag gcatagaaaa aaaactgata atgataatga gatttgtcac tatacttatc       600
ctatccctac ataggagccg tttgattgtt tagtccatgt tttcattttg tttagtctaa       660
tgctatataa cttttcttta tcagtctatt gttatatgac ttatatatat ctcaagagat       720
aaggccaata aatcttcttc ttaattatat ctgaagactc aaaacatatt ttgagtttaa       780
taaaataaat aacgtccaaa tgctacatac aaacggacca aattcatgga ggtataaatt       840
taaattattt tttgttccaa agtgtatgca gtgatttatt gatgaatgcg atagagcggc       900
gaaagagaat aatcgtcacc tagaagacaa attgatcggc cgtacatata tacataaata       960
caaacctgcc acttcacatg tcacccaccc ttaagcaccc ccttcacata catactttct      1020
ataacaaaaa tatcagcttc tagttcatat ttatgttaca ataactcgag tgaatcatac      1080
taaaaaaatg taatgctttc tctaaatagg agataaaatg caccctccga cctaactaaa      1140
gattccttat tttagctatt taagacatat tgcacatgta tagagataca taaacacata      1200
tgcaatatgc acatcttcta tacattgaaa aaagctgatc ttgcaaatat ttgtcttaca      1260
caacacaagc gaccaaagcg atgcgtttcc caatgataag gttacgacat acttacacga      1320
ctctctctat tgtctcgtct ctttcttttcc tcatccctct cctttgtctc ctttcactct      1380 attttttcact tttcagaata cttttacgta aaaatcatgg acatgtcatt gtctccaccc      1440
tactatactc tttttttgtt cttttttgttt                                      1470
```

<210> SEQ ID NO 37
<211> LENGTH: 1793
<212> TYPE: DNA
<213> ORGANISM: Arabidopsis thaliana

<400> SEQUENCE: 37

```
ttggttgtct ggcatcatca ttttgtaccg tttctcccaa agtaagaaac ggtacaatct        60
tctcttatat agatttcata cccccaaaacc ctaaattcat tagggttttc aaaaaaaaaa      120
atcacgttta cctctaaacc aatcttctct tatatagata aatcataacg tttgtttgat       180
```

```
ttttcagttt tctacttaac caatattaaa ctaaagtcga attgagatga gtggtagcaa      240
accacagttt aattaagaag ttaattatag gccacatgat tgagcaagcc tttttgtttt      300
gtaacacatc ttatcagctg cttaaaattt tggctgcctc ccattggcca actggtctaa      360
acatcattgc attggcattc tcataatcaa tcaatctaat gagaaacttt gaatatttat      420
gaaaaactga ataacaacat aacataaacg aacaatgtaa aaagaaaaa cacaaaaaaa       480 aaaacacttt aaaaaacaaa aaccaaaaac tcttaaacta taaactcatg aacacttagt      540
gatgaggtct gaaagggtgt aaccaccacc tgttgtcaat aggtgacaac ttcttcttgg      600
gaacattcgg gaaagtgaag gcttaggtga cggttgtctt aaaagtctct tttagttaat      660
tcatcgtatt ttcgatgggc attacgtttg atgcataaag gcccatatgg gctatacatg      720
tactgcgttt gagtggcttt ctaaggattg atgtattgtc tctatgagag tattcgttta      780
actcatggag atctactctc cacgatattt tctgtaaact tttcttttg ttgattagat       840 aaatagaaaa ttgtgtagag cgaaacttt aatgaattaa aatgcggaag cgattaaagc       900
atgaatagat aaattggaca agagattaaa cgagggatca tctagttttt acactgatca      960
ctagtcatct gcttgcagaa gaagtatatc attaatcaag caaaacgagg gcataaattt     1020
cttacaaata acttttacag taggttaatg atttttttaat aacttgtcca tttcacatgc    1080
atgtgtatct ttgtactata catgctaagt gtttcattaa tcaagataaa cgtgtctacg     1140
aataacttaa aacagtacaa cttccctaaa aaattcatta aatgaaaggt ttttatagat     1200
tatacattgc acggtacggt tcggttacca ttcgaagtct aaaaagagaa tgacggttct     1260
gataatgctt ttaatcgctt ttgtattgta aatcattaaa acagtaagcc ggataccgaa     1320
ttactaatca gacccaaaaa agaatctata ggaaaaatat caactgaaga gcgggtaggc     1380
ttgaccttga aaggaagaat ggtgagcgag cggtggatag atatgtaata aattgtaacg     1440
ctttcaaaat gtcaaagtca caagtcacat tactcacgag ccaacactaa ccatgcaact     1500
tttgttttga cattttccta aactttaggt ataaaatacc cgcgtaataa ataacctctt     1560
cataattggg tccacccact cacaggtcca cacataagga accgaaaaag gtaaaattca    1620
aaaacttaca aagttttta gagatgatgt ggtgaagtat tgcattaatg gaataatggg     1680
aaaagaaagt aattgcaacg tacgtataga ttaatccatt gacacaaatg aaaagtttct    1740
ttctatttaa tgtacacaac aaaggttctc ttcagagtaa tttaggggaa aaa           1793

<210> SEQ ID NO 38
<211> LENGTH: 257
<212> TYPE: DNA
<213> ORGANISM: Arabidopsis thaliana

<400> SEQUENCE: 38
acacaacagg tccctacatt tgtacaatct cctctcttta aagactctct ctctttctct       60
ctccatctct atcttactct gtatttctgt cgtctgagca ctcaatgaaa ccactgtaaa      120
tttccgccag aatttgatgt gatggaacga taaaaatcat tttttctcgg ttaaagtaaa      180 aaacaaaaa caaatttctg tagaaatcat aataaaagaa agaaaaaaaa tctaatgtcg      240
gtacataata cggttct                                                     257
```

COMPOSITIONS AND METHODS FOR ALTERING FLOWERING AND PLANT ARCHITECTURE TO IMPROVE YIELD POTENTIAL

CROSS-REFERENCE TO RELATED APPLICATIONS

This application claims priority benefit to U.S. Provisional Patent Application Nos. 62/150,142 and 62/233,019, filed on Apr. 20, 2015 and Sep. 25, 2015, respectively, which are incorporated herein by reference in their entirety.

INCORPORATION OF SEQUENCE LISTING

A computer readable form of a sequence listing is filed with this application by electronic submission and is incorporated into this application by reference in its entirety. The sequence listing is contained in the file named 60760-anniversary_ST25.txt, which is 61,089 bytes in size (measured in operating system MS Windows) and created on Apr. 18, 2016.

FIELD OF THE INVENTION

The present invention relates to compositions and methods for modulating floral development and vegetative growth by genetic modification of crop plants to increase yield.

BACKGROUND

The transition from vegetative growth to flowering is a crucial process during plant development that is necessary for the production of grain yield in crop plants. There are four major pathways controlling flowering time in land plants that respond to environmental or developmental cues, including photoperiodism (i.e., day length), vernalization (i.e., response to winter cold), and plant hormones (e.g., gibberellins or GA), in addition to the autonomous (environmentally independent) pathways. Except for the GA and autonomous pathways, regulation of flowering in plants generally involves two central regulators of flowering time, CONSTANS (CO) and FLOWERING LOCUS C (FLC). The FLC gene is a floral repressor that regulates flowering in response to vernalization, whereas the CO gene is a floral activator that responds to photoperiod conditions. Under inductive photoperiodic conditions, CO activity in source leaves increases expression of FLOWERING LOCUS T (FT), which translocates to the meristem to trigger expression of downstream floral activating genes, including LEAFY (LFY), APETALA1 (AP1) and SUPPRESSOR OF OVEREXPRESSION OF CO 1 (SOC1). Other genes, such as FLOWERING LOCUS C (FLC) and TERMINAL FLOWER 1 (TFL1), act to inhibit the expression or activity of these genes.

Except for day length neutral plants, most flowering plants respond to daily photoperiodic cycles and are classified as either short day (SD) or long day (LD) plants based on the photoperiod conditions required to induce flowering. The photoperiod refers to the relative length or duration of light and dark periods within a 24-hour cycle. In general, long day plants tend to flower when the day length exceeds a photoperiod threshold (e.g., as the days are getting longer in the spring), whereas short day plants tend to flower when the day length falls below a photoperiod threshold (e.g., as the days are getting shorter after the summer solstice). In other words, SD plants flower as the days are getting shorter, while LD plants flower as the days are getting longer. Soybean is an example of a short day (SD) plant in which flowering is induced when plants are exposed to shorter daylight conditions.

Plant growers are always looking for new methods to manipulate the yield of a plant, especially to enhance the seed yield of agronomically important crops. Thus, there is a continuing need in the art for improved compositions and methods for increasing yields of various crop plants. It is presently proposed that improved crop yields may be achieved by enhancing agronomic traits related to flowering and reproductive development.

SUMMARY

According to a first aspect of the present invention, a recombinant DNA construct is provided comprising a polynucleotide sequence encoding a florigenic FT protein operably linked to a vegetative stage promoter. The florigenic FT protein encoded by the polynucleotide sequence may comprise an amino acid sequence having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or least 99% identity to a sequence selected from the group consisting of SEQ ID NOs: 2, 4, 6, 8, 10, 12, 14, 16, 18, and 20, or a functional fragment thereof. The polynucleotide sequence may also be at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or least 99% identity to a sequence selected from the group consisting of SEQ ID NOs: 1, 3, 5, 7, 9, 11, 13, 15, 17, and 19. The vegetative stage promoter may further be a meristem-preferred or meristem-specific promoter. DNA molecules and vectors comprising such a recombinant DNA construct are further provided.

According to a second aspect of the present invention, transgenic plants, plant cells, plant tissues and plant parts are further provided comprising an insertion of the recombinant DNA construct of the present invention into the genome of such plants, cells, tissues, and plant parts. A transgenic plant of the present invention may be homozygous or hemizygous for an insertion of the recombinant DNA construct. A transgenic plant may be a short day plant and/or a dicotyledonous plant. Depending on the plant species, transgenic plants of the present invention may produce more bolls, siliques, fruits, nuts, or pods per node of the transgenic plant, relative to a control or wild type plant not having the recombinant DNA construct. Transgenic plants of the present invention may also produce more flowers and/or floral racemes per node relative to a control or wild type plant not having the recombinant DNA construct.

According to a third aspect of the present invention, methods for producing a transgenic plant having improved yield-related traits or phenotypes are provided comprising (a) transforming at least one cell of an explant with a recombinant DNA construct comprising a polynucleotide sequence encoding a florigenic FT protein operably linked to a vegetative stage promoter; and (b) regenerating or developing the transgenic plant from the transformed explant. Such methods may further comprise (c) selecting a transgenic plant having one or more of the following traits or phenotypes: earlier flowering, longer reproductive or flowering duration, increased number of flowers per node, increased number of floral racemes per node, increased number of pods, bolls, siliques, fruits, or nuts per node, and increased number of seeds per node, as compared to a control plant not having the recombinant DNA construct.

According a fourth aspect of the present invention, methods are provided for planting a transgenic crop plant of the present invention at a normal or higher density in the field. According to some embodiments, methods are provided comprising: planting a transgenic crop plant at a higher density in the field, wherein the transgenic crop plant is transformed with a recombinant DNA construct comprising a polynucleotide sequence encoding a florigenic FT protein operably linked to a vegetative stage promoter. According to some of these embodiments, the vegetative stage promoter may be a meristem-preferred or meristem-specific promoter. For soybean, a higher density of about 150,000 to 250,000 seeds of the transgenic soybean plant may be planted per acre. For cotton, a higher density of about 48,000 to 60,000 seeds of the transgenic cotton plant may be planted per acre. For canola, a higher density of about 450,000 to 680,000 seeds of the transgenic canola plant may be planted per acre.

BRIEF DESCRIPTION OF THE DRAWINGS

FIG. 1A provides a matrix table showing a comparison of nucleotide sequences for each combination of the various FT genes including their percent identity.

FIG. 1B provides a matrix table showing a comparison of protein sequences for each combination of the various FT proteins including their percent identity.

FIG. 1C provides a CLUSTAL 2.0.9 multiple sequence alignment of various FT proteins identified as Gm.FT2a with SEQ ID NO: 2, Gm. FT2b with SEQ ID NO: 6, Le. FT with SEQ ID NO: 12, Pt.FT with SEQ ID NO: 20, Os.HD3a with SEQ ID NO: 18, At.FT with SEQ ID NO: 14, At. TSF with SEQ ID NO: 16, Nt.FT with SEQ ID NO: 10, Gm.FT5a with SEQ ID NO: 4 and Zm.ZCN8 with SEQ ID NO: 8.

FIGS. 3A to 3O are a set of black and white images of stained tissues, and the images in FIGS. 4A to 4O correspond to FIGS. 3A to 3O but are filtered for blue GUS staining. FIGS. 3A to 3C and 4A to 4C show expression in a 3-day-old germinating seedling; FIGS. 3M to 3O and 4M to 4O show expression in the 30 d old mature and immature leaves of the reproductive shoot. Bars are 100 μm.

FIGS. 5A to 5F and FIGS. 6A to 6F show the GUS expression pattern with the pAT.Erecta promoter during R1 and floral stages of development (35-40 days after germination). FIGS. 5A to 5F are a set of black and white images of stained tissues, and the images in FIGS. 6A to 6F correspond to FIGS. 5A to 5F but are filtered for blue GUS staining. FIGS. 5A and 6A show expression in the inflorescence stems or pedicels (arrows), and FIGS. 5B and 6B show expression in the floral peduncle (arrows). Expression is also shown in the vasculature and parenchyma cells (FIGS. 5C and 6C), in stamen filaments (FIGS. 5D and 6D; arrow), and un-pollinated ovules (FIGS. 5E, 5F, 6E and 6F; arrows). Bars are 1 mm.

FIG. 9A depicts a null segregant showing normal axillary buds, whereas FIG. 9B and FIG. 9C (corresponding to plants homozygous or hemizygous for the Gm.FT2a transgene, respectively) each show early flowering and increased pods per node relative to the null segregant.

FIG. 11 shows images of the main stem of plants that are homozygous or hemizygous for the pAt.Erecta-Gm.FT2a transgene in comparison to a null segregant as indicated.

FIG. 12A shows whole plant images of a wild type null segregant and a plant homozygous for the pEr:Zm.ZCN8 transgene as indicated.

FIG. 12B shows close up images of pods on the mainstem of a wild type null segregant and a plant homozygous for the pEr:Zm.ZCN8 transgene as indicated.

FIG. 13A shows whole plant images of a wild type null segregant and a plant homozygous for the pEr:Nt.FT-like transgene as indicated.

FIG. 13B shows close up images of pods on the mainstem of a wild type null segregant and a plant homozygous for the pEr:Nt.FT-like transgene as indicated.

FIG. 15 shows whole plant images of a wild type null segregant and a plant homozygous for the pEr:Le.SFT transgene as indicated.

FIG. 16 shows whole plant images of a wild type null segregant and a plant homozygous for the pEr:FT5a transgene as indicated.

DETAILED DESCRIPTION

Figure 2:
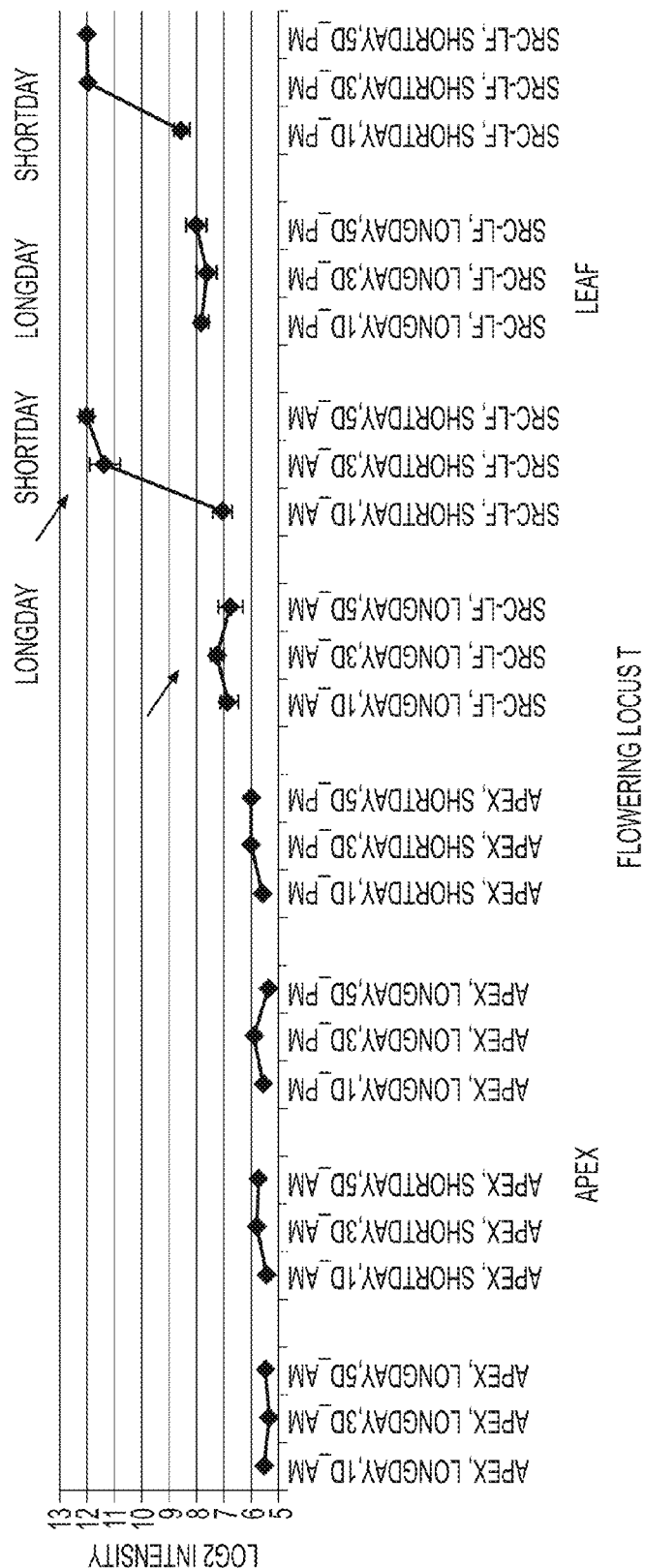
FIG. 2 shows the total FT transcript levels in soybean leaf and apex tissues collected at 1, 3 and 5 days after either a short day or long day light treatment.
Figure 3A:
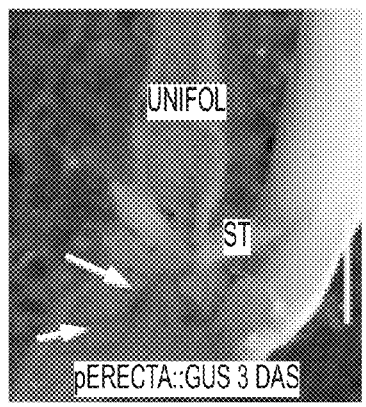
FIGS. 3A to 3O and FIGS. 4A to 4O show the expression pattern of the pAt.Erecta promoter by monitoring GUS activity during early soybean development.
Figure 3B:
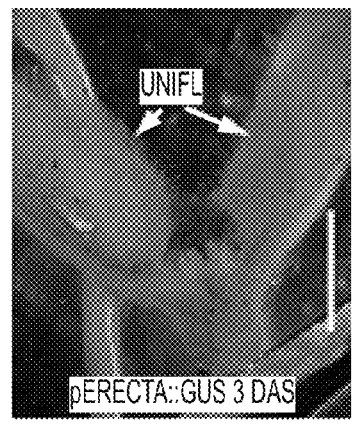
Figure 3C:
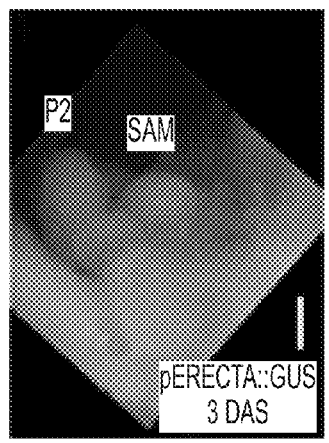
Figure 3D:
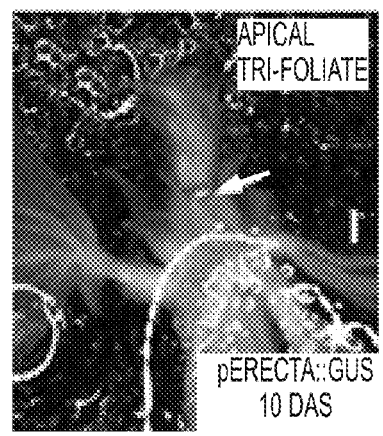
FIGS. 3D to 3I and 4D to 4I show expression in a 10-day-old vegetative shoot (grown in 14 hour light/10 hour dark photoperiod)
Figure 3E:
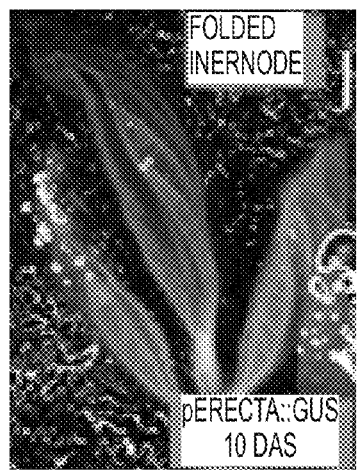
Figure 3F:
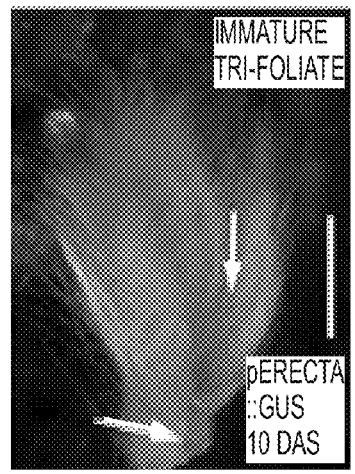
Figure 3G:
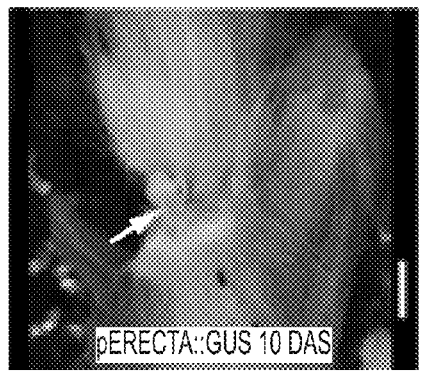
Figure 3H:
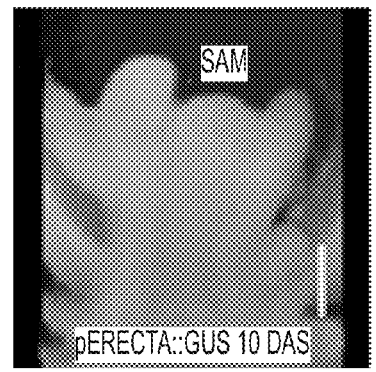
Figure 3I:
Figure 3J:
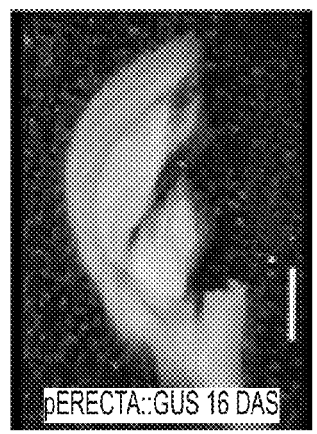
FIGS. 3J to 3L and 4J to 4L show expression in a 16-day-old reproductive shoot.
Figure 3K:
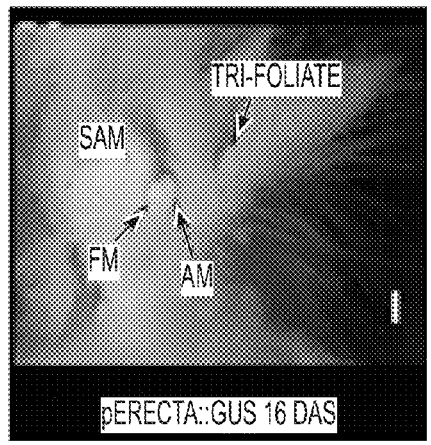
Figure 3L:
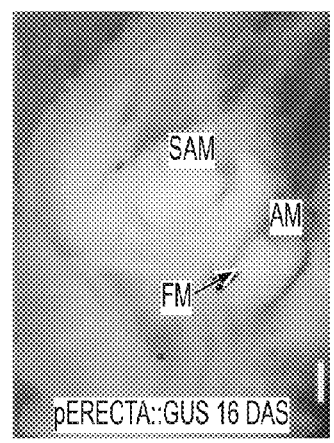
Figure 3M:
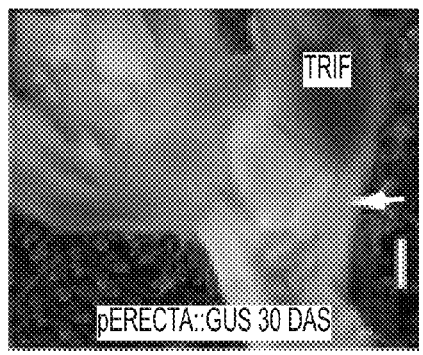
Figure 3N:
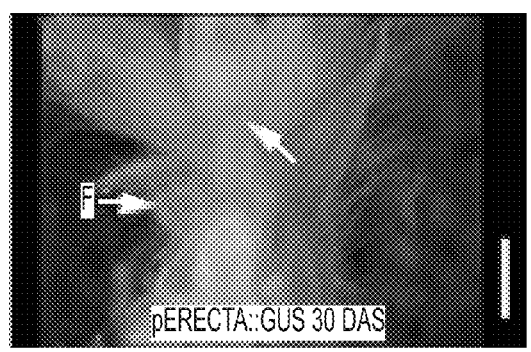
Figure 3O:
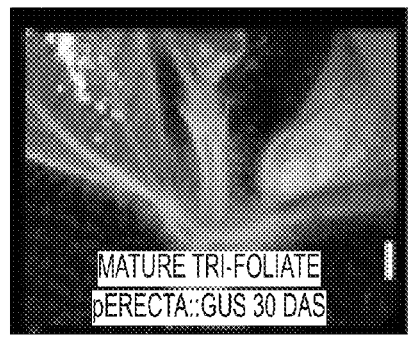

The goal of improving yield is common to all crops across agriculture. The present invention includes methods and compositions for improving yield in flowering (angiosperm) or seed-bearing plants by modification of traits associated with flowering time, reproductive development, and vegetative growth to improve one or more flowering and/or yield-related traits or phenotypes, such as the number of flowers, seeds and/or pods per plant, and/or the number of flowers, seeds and/or pods per node (and/or per main stem) of the plant. Without being bound by any theory, compositions and methods of the present invention may operate to improve yield of a plant by increasing the number of floral meristems, increasing synchronization of lateral meristem release, and/or extending the time period for pod or seed development in the plant.

Previously, it was discovered that growing short day plants, such as soybean, under long day conditions (e.g., about 14-16 hours of light per day) and then briefly subjecting those plants to short day growing conditions (e.g., about 9-11 hours of light per day for about 3-21 days) before returning the plants to long day (non-inductive) growing conditions, produced plants having increased numbers of pods/seeds per plant (and pods/seeds per node and/or per branch). See, e.g., U.S. Pat. No. 8,935,880 and U.S. Patent Application Publication No. 2014/0259905, the entire contents and disclosures of which are incorporated herein by reference.

As described further below, this short day induction phenotype in soybean was used to identify genes having altered expression in these plants through transcriptional profiling. These studies identified several genes with altered expression in these treated soybean plants including an endogenous FT gene, Gm.FT2a, having increased expression in response to the short day induction treatment. Thus, it is presently proposed that transgenic FT expression as described herein may be used in place of short day induction to increase seed yield, alter reproductive traits or phenotypes in plants, or both. According to an aspect of the present invention, ectopic or transgenic expression of a Gm.FT2a gene or other FT sequence, or a functional fragment, homolog or ortholog thereof, in a flowering or seed-bearing plant may be used to increase seed yield and/or alter one or more reproductive phenotypes or traits, which may involve an increase in the number of pods/seeds per plant (and/or the number of pods/seeds per node or main stem of the plant). As explained further below and depending on the particular plant species, these yield-related or reproductive phenotypes or traits may also apply to other botanical structures analogous to pods of leguminous plants, such as bolls, siliques, fruits, nuts, tubers, etc. Thus, a plant ectopically expressing a FT sequence may instead have an increased number of bolls, siliques, fruits, nuts, tubers, etc., per node(s), main stem, and/or branch(es) of the plant, and/or an increased number of bolls, siliques, fruits, nuts, tubers, etc., per plant.

According to embodiments of the present invention, a recombinant DNA molecule comprising an FT transgene is provided, which may be used in transformation to generate a transgenic plant expressing the FT transgene. The polynucleotide coding sequence of the FT transgene may include Gm.FT2a (SEQ ID NO: 1), or any polynucleotide sequence encoding the Gm.FT2a protein (SEQ ID NO: 2). The polynucleotide coding sequence of an FT transgene may also correspond to other FT genes in soybean or other plants. For example, other polynucleotide FT coding sequences from soybean that may be used according to present embodiments include: Gm.FT5a (SEQ ID NO: 3) or a polynucleotide encoding a Gm.FT5a protein (SEQ ID NO: 4), or Gm.FT2b (SEQ ID NO: 5) or a polynucleotide encoding a Gm.FT2b protein (SEQ ID NO: 6). In addition, examples of polynucleotide FT coding sequences from other plant species that may be used include: Zm.ZCN8 (SEQ ID NO: 7) from maize or a polynucleotide encoding Zm.ZCN8 protein (SEQ ID NO: 8), Nt.FT-like or Nt.FT4 (SEQ ID NO: 9) from tobacco or a polynucleotide encoding Nt.FT-like or Nt.FT4 protein (SEQ ID NO: 10), Le.FT or SFT (SEQ ID NO: 11) from tomato or a polynucleotide encoding Le.FT or SFT protein (SEQ ID NO: 12), At.FT (SEQ ID NO: 13) from *Arabidopsis* or a polynucleotide encoding At.FT protein (SEQ ID NO: 14), At.TSF (SEQ ID NO: 15) from *Arabidopsis* or a polynucleotide encoding At.TSF protein (SEQ ID NO: 16), Os.HD3a (SEQ ID NO: 17) from rice or a polynucleotide encoding Os.HD3a protein (SEQ ID NO: 18), or Pt.FT (SEQ ID NO: 19) from *Populus trichocarpa* or a polynucleotide encoding Pt.FT protein (SEQ ID NO: 20).

Polynucleotide coding sequences for FT transgenes encoding additional FT proteins from other species having known amino acid sequences may also be used according to embodiments of the present invention, which may, for example, include the following: Md.FT1 and Md.FT2 from apple (*Malus domestica*); Hv.FT2 and Hv.FT3 from barley (*Hordeum vulgare*); Cs.FTL3 from *Chrysanthemum*; Ls.FT from lettuce (*Lactuca sativa*); Pn.FT1 and Pn.FT2 from Lombardy poplar (*Populus nigra*); Pa.FT from London plane tree (*Platanus acerifolia*); Dl.FT1 from Longan (*Dimocarpus longan*); Ps.FTa1, Ps.FTa2, Ps.FTb1, Ps.FTb2, and Ps.FTc from pea (*Pisum sativum*); Ac.FT from pineapple (*Ananas comosus*); Cm-FTL1 and Cm-FTL2 from pumpkin (*Cucurbita maxima*); Ro.FT from rose; Cg.FT from spring orchid (*Cymbidium*); Fv.FT1 from strawberry (*Fragaria vesca*); Bv.FT2 from sugar beet (*Beta Vulgaris*); Ha.FT4 from sunflower (*Helianthus annuus*); and Ta.FT or TaFT1 from wheat (*Triticum aestivum*). See, e.g., Wickland, D P et al., "The Flowering Locus T/Terminal Flower 1 Gene Family: Functional Evolution and Molecular Mechanisms", *Molecular Plant* 8: 983-997 (2015), the content and disclosure of which is incorporated herein by reference.

Unless otherwise stated, nucleic acid or polynucleotide sequences described herein are provided (left-to-right) in the 5' to 3' direction, and amino acid or protein sequences are provided (left-to-right) in the N-terminus to C-terminus direction. Additional known or later discovered FT genes and proteins from these or other species may also be used according to embodiments of the present invention. These FT genes may be known or inferred from their nucleotide and/or protein sequences, which may be determined by visual inspection or by use of a computer-based searching and identification tool or software (and database) based on a comparison algorithm with known FT sequences, structural domains, etc., and according to any known sequence alignment technique, such as BLAST, FASTA, etc.

According to embodiments of the present invention, an FT transgene of a recombinant DNA molecule may comprise a polynucleotide sequence that (when optimally aligned) is at least 60% identical, at least 65% identical, at least 70% identical, at least 75% identical, at least 80% identical, at least 85% identical, or at least 90%, at least 91%, at least 92%, at least 93%, at least 94%, at least 95%, at least 96%, at least 97%, at least 98%, or least 99% identical to one or more of the polynucleotide FT coding sequences listed above (e.g., SEQ ID NOS: 1, 3, 5, 7, 9, 11, 13, 15, 17, or 19), or to any other known florigenic FT coding sequence. Sequence identity percentages among polynucleotide sequences of the above listed full length FT genes are presented in FIG. 1A. Each cell in the table in FIG. 1A shows the percentage identity for the FT gene in the corresponding row (query sequence) as compared to the FT gene in the corresponding column (subject sequence) divided by the total length of the query sequence, and the number in parenthesis is the total number of identical bases between the query and subject sequences. As shown in this figure, the percentage identities among polynucleotide sequences for these sampled FT genes range from about 60% to about 90% identity. Thus, a polynucleotide sequence that is within one or more of these sequence identity ranges or has a higher sequence identity may be used according to embodiments of the present invention to induce flowering, increase yield, and/or alter one or more reproductive traits of a plant. Similar polynucleotide coding sequences for FT may be designed or chosen based on known FT protein sequences, conserved amino acid residues and domains, the degeneracy of the genetic code, and any known codon optimizations for the particular plant species to be transformed.

As described below, an FT transgene comprising any one of the above coding sequences may further include one or more expression and/or regulatory element(s), such as leader(s), intron(s), etc. Indeed, an FT transgene may comprise a genomic sequence encoding an FT protein or amino acid sequence, or a fragment or portion thereof.

According to embodiments of the present invention, an FT transgene of a recombinant DNA molecule may comprise a polynucleotide sequence encoding an amino acid or protein sequence that (when optimally aligned) is at least 60% identical, at least 65% identical, at least 70% identical, at least 75% identical, at least 80% identical, at least 85% identical, or at least 90%, at least 91%, at least 92%, at least 93%, at least 94%, at least 95%, at least 96%, at least 97%, at least 98%, or least 99% identical to any one or more of the FT protein or amino acid sequences listed above (e.g., SEQ ID NOS: 2, 4, 6, 8, 10, 12, 14, 16, 18, or 20) or any other known florigenic FT protein sequence, or a functional fragment thereof. Such a "functional fragment" is defined as a protein having a polypeptide sequence that is identical or highly similar to a full-length FT protein but lacking one or more amino acid residues, portions, protein domains, etc., of the full-length FT protein, as long as the fragment remains active in causing one or more of the phenotypic effects or changes similar to the full-length protein when transgenically expressed in a plant. Sequence identity percentages among the above listed full length FT proteins are presented in FIG. 1B. The percentages are calculated as described above in reference to FIG. 1A based on the number of identical amino acid residues (in parenthesis) between the query and subject FT protein sequences. Multiple sequence alignment of these FT proteins is also shown in FIG. 1C. As can be seen from these figures, the percentage identity among protein sequences for these FT genes ranges from about 60% to about 90% identity. Thus, a polynucleotide sequence encoding an amino acid or protein sequence that is within one or more of these sequence identity ranges or has a higher sequence identity may be used according to embodiments of the present invention to induce flowering, increase seed yield, and/or alter one or more reproductive traits of a plant. These FT protein sequences encoded by a polynucleotide sequence of the present invention may be designed or chosen based on known FT protein sequences and their conserved amino acid residues and domains.

As used herein, the term "sequence identity" refers to the extent to which two optimally aligned DNA sequences are identical. Various pair-wise or multiple sequence alignment algorithms and programs are known in the art, such as ClustalW, etc., that may be used to compare the sequence identity or similarity between two or more sequences, such as between two or more FT genes or protein sequences, or an FT gene (nucleotide) or protein sequence and another nucleotide or protein sequence. For example, the percentage identity of one sequence (query) to another sequence (subject) may be calculated as described above in reference to FIGS. 1A and 1B (i.e., with the sequences optimally aligned, divide the number of identical bases or residues by the total number of bases or residues for the query sequence, and multiply by 100%). Although other alignment and comparison methods are known in the art, the alignment and percent identity between two sequences (including the percent identity ranges described above) may be as determined by the ClustalW algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); and Larkin M A et al., "Clustal W and Clustal X version 2.0," *Bioinformatics* 23: 2947-48 (2007), the entire contents and disclosures of which are incorporated herein by reference. For purposes of the present invention, when two sequences are optimally aligned (with allowance for gaps in their alignment), then the "percent identity" for the query sequence is calculated as described above in reference to FIGS. 1A and 1B—i.e., Percent Identity=(Number of Identical Positions between query and subject sequences/Total Number of Positions in the Query Sequence)×100%, with each sequence consisting of a series of positions (nucleotide bases or amino acid residues).

An FT protein sequence encoded by a polynucleotide sequence or transgene of the present invention may also be designed or chosen to have one or more amino acid substitution(s) known to be chemically and/or structurally conservative (e.g., replacing one amino acid with another having similar chemical or physical properties, such as hydrophobicity, polarity, charge, steric effect, acid/base chemistry, similar side chain group, such as hydroxyl, sulfhydryl, amino, etc.) to avoid or minimize structural changes to the protein that might affect its function. For example, valine is often a conservative substitute for alanine, and threonine may be a conservative substitute for serine. Additional examples of conservative amino acid substitutions in proteins include: valine/leucine, valine/isoleucine, phenylalanine/tyrosine, lysine/arginine, aspartic acid/glutamic acid, and asparagine/glutamine. An FT protein sequence encoded by a polynucleotide sequence or transgene of the present invention may also include proteins that differ in one or more amino acids from those of a known FT protein or similar sequence as a result of deletion(s) and/or insertion(s) involving one or more amino acids.

Various FT genes and proteins from different plant species may be identified and considered FT homologs or orthologs for use in the present invention if they have a similar nucleic acid and/or protein sequence and share conserved amino acids and/or structural domain(s) with at least one known FT gene or protein. As used herein, the term "homolog" in reference to a FT gene or protein is intended to collectively include any homologs, analogs, orthologs, paralogs, etc., of the FT gene or protein, and the term "homologous" in reference to polynucleotide or protein sequences is intended to mean similar or identical sequences. Such a FT homolog may also be defined as having the same or similar biological function as known FT genes (e.g., acting to similarly influence flowering and/or other reproductive or yield-related traits or phenotypes when ectopically expressed in a plant).

Sequence analysis and alignment of FT protein sequences from different plant species further reveals a number of conserved amino acid residues and at least one conserved structural domain. By subjecting the various aligned FT protein sequences (see, e.g., FIGS. 1B and 1C) to a protein domain identification tool using a Pfam database (e.g., Pfam version 26.0, released November 2011, or later version), these FT proteins have been found to contain and share at least a portion of a putative phosphatidyl ethanolamine-binding protein (PEBP) domain (Pfam domain name: PBP_N; Accession number: PF01161). See, e.g., Banfield, M J et al., "The structure of *Antirrhinum* centroradialis protein (CEN) suggests a role as a kinase inhibitor," *Journal of Mol Biol.,* 297(5): 1159-1170 (2000), the entire contents and disclosure of which are incorporated herein by reference. This PEBP domain was found to correspond, for example, to amino acids 28 through 162 of the full length Gm.FT2a protein (See Table 5 below). Thus, FT proteins encompassed by embodiments of the present invention may include those identified or characterized as having or containing at least a PEBP domain (Accession number: PF01161) according to Pfam analysis. Accordingly, the present invention may further include a polynucleotide sequence(s) encoding an FT protein having at least a PEBP domain. As known in the art, the "Pfam" database is a large collection of multiple sequence alignments and hidden Markov models covering many common protein families and containing information about various protein families and their domain structure(s). By identifying a putative Pfam structural domain(s) for a given protein sequence, the classification and function of the protein may be inferred or determined. See, e.g., Finn, R D et al., "The Pfam protein families database," *Nucleic Acids Research (Database Issue)*, 42:D222-D230 (2014), the entire contents and disclosure of which are incorporated herein by reference.

Embodiments of the present invention may further include polynucleotide sequence(s) encoding inductive or florigenic FT proteins. An FT protein encoded by a polynucleotide sequence may be "inductive" or "florigenic" if the FT protein, when ectopically expressed in a plant, is able to cause earlier flowering and/or an increased prolificacy in the number of flowers, pods, and/or seeds per one or more node(s) of the plant. Without being bound by any theory, such increased prolificacy in the number of flowers, pods, and/or seeds per node(s) of the plant may result from an increase in the number of meristems at those node(s) that undergo a vegetative to reproductive transition and produce flowers. Such an increased prolificacy at each node due to ectopic expression of a "florigenic" FT may be due to increased synchronization of the release and floral development of early racemes and lateral meristems at each node. Although a "florigenic" FT protein may function to induce earlier flowering when ectopically expressed in a plant, a transgenically expressed "florigenic" FT protein may increase the number of flowers, pods, and/or seeds per node(s) of a plant through one or more pathways or mechanisms that are independent of, or in addition to, any florigenic effects related to flowering time and/or reproductive duration.

Florigenic FT-like genes from various plant species are generally well conserved. However, many proteins in the PEBP family have amino acid sequences that are substantially similar to florigenic FT proteins but do not behave as florigens. For example, Terminal Flower (TFL) genes from various plant species have similar protein sequences to florigenic FT genes but actually delay flowering. Recent work has identified specific amino acid residues that are generally not shared between florigenic FT proteins and other PEBP proteins, such as TFLs, and substitutions at many of these positions have been shown to convert florigenic FT proteins into floral repressor proteins. See, e.g., Ho and Weigel, *Plant Cell* 26: 552-564 (2014); Danilevskaya et al., *Plant Physiology* 146(1): 250-264 (2008); Hang et al., *Plant Journal* 72: 908-921 (2012); Hsu et al., *Plant Cell* 18: 1846-1861 (2006); Kojima et al., *Plant Cell Physiology* 43(10): 1096-1105 (2002); Kong et al., *Plant Physiology* 154: 1220-1231 (2010); Molinero-Rosales et al., *Planta* 218: 427-434 (2004); Zhai et al., *PLoS ONE*, 9(2): e89030 (2014), and Wickland D P et al. (2015), supra, the entire contents and disclosures of which are incorporated herein by reference. Thus, these amino acid residues can serve as signatures to further define and distinguish florigenic FT proteins of the present invention.

According to embodiments of the present invention, an "inductive" or "florigenic" FT protein may be further defined or characterized as comprising one or more of the following amino acid residue(s) (amino acid positions refer to corresponding positions of the full-length *Arabidopsis* FT protein, SEQ ID NO: 14): a proline at amino acid position 21 (P21); an arginine or lysine at amino acid position 44 (R44 or K44); a glycine at amino acid position 57 (G57); a glutamic acid or an aspartic acid at amino acid position 59 (E59 or D59); a tyrosine at amino acid position 85 (Y85); a leucine at amino acid position 128 (L128); a glycine at amino acid position 129 (G129); a threonine at amino acid position 132 (T132); an alanine at amino acid position 135 (A135); a tryptophan at amino acid position 138 (W138); a glutamic acid or an aspartic acid at amino acid position 146 (E146 or D146); and/or a cysteine at amino acid position 164 (C164). Corresponding amino acid positions of other FT proteins can be determined by alignment with the *Arabidopsis* FT sequence (see, e.g., FIG. 1C). One skilled in the art would be able to identify corresponding amino acid positions of other FT proteins based on their sequence alignment. Several of these key residues fall within an external loop domain of FT-like proteins, defined as amino acids 128 through 145 of the *Arabidopsis* full-length FT sequence (SEQ ID NO: 14) and corresponding sequences of other FT proteins (see, e.g., FIG. 1C). Thus, polynucleotides of the present invention may encode florigenic FT proteins having one or more of these conserved amino acid residues.

Florigenic FT proteins of the present invention may also have one or more other amino acids at one or more of the above identified residue positions. For example, in reference to the above amino acid positions of the *Arabidopsis* FT (At.FT) protein sequence (SEQ ID NO: 14), a florigenic FT protein may alternatively have one or more of the following amino acids: an alanine (in place of proline) at the position corresponding to position 21 of the At.FT protein sequence (P21A), or possibly other small, nonpolar residues, such as glycine or valine, at this position; a histidine (in place of lysine or arginine) at the amino acid position corresponding to position 44 of the At.FT protein sequence, or possibly other polar amino acids at this position; an alanine or cysteine (in place of glycine) at the amino acid position corresponding to position 57 of the At.FT protein sequence, or possibly other small, nonpolar residues, such proline or valine, at this position; an asparagine or serine (in place of glutamic acid or aspartic acid) at the amino acid position corresponding to position 59 of the At.FT protein sequence, or possibly other small, polar residues, such as glutamine, cysteine, or threonine, at this position; a variety of polar and nonpolar uncharged residues (other than tyrosine) at the amino acid position corresponding to position 85 of the At.FT protein sequence; a nonpolar or hydrophobic uncharged residue (other than leucine), such as isoleucine, valine, or methionine, at the amino acid position corresponding to position 128 of the At.FT protein sequence; a variety of smaller nonpolar and uncharged residues (other than glycine), such as alanine, valine, leucine, isoleucine, methionine, etc., at the amino acid position corresponding to position 129 of the At.FT protein sequence, although some polar and charged residues may be tolerated at this position; a polar uncharged residue (other than threonine) at the amino acid position corresponding to position 132 of the At.FT protein sequence; a variety of amino acids other than proline, such as threonine, at the amino acid position corresponding to position 135 of the At.FT protein sequence; a variety of other bulky nonpolar or hydrophobic amino acids (in place of tryptophan), such as methionine or phenylalanine, at the amino acid position corresponding to position 138 of the At.FT protein sequence; a variety of other polar or non-positively charged amino acids, such as asparagine or serine, at the amino acid position corresponding to position 146 of the At.FT protein sequence; and/or a variety of other polar or nonpolar amino acids (in place of cysteine, such as isoleucine, at the amino acid position corresponding to position 164 of the At.FT protein sequence. One skilled in the art would be able to identify corresponding amino acid positions and substitutions of FT proteins based on their sequence alignment to the *Arabidopsis* FT protein sequence. In addition, other chemically conservative amino acid substitutions are also contemplated within the scope of florigenic FT proteins based on the knowledge of one skilled in the art of protein biochemistry. Accordingly, polynucleotides of the present invention may further encode florigenic FT proteins having one or more conservative amino acid substitutions. Indeed, florigenic FT proteins encoded by polynucleotides of the present invention include native sequences and artificial sequences containing one or more conservative amino acid substitutions, as well as functional fragments thereof.

Florigenic FT proteins of the present invention may also be defined as excluding (i.e., not having) one or more amino acid substitutions that may be characteristic of, or associated with, TFL or other non-florigenic or anti-florigenic proteins. For example, in reference to the amino acid positions of the *Arabidopsis* FT protein sequence (SEQ ID NO: 14), a florigenic FT protein may exclude one or more of the following amino acids: a phenylalanine or serine at the position corresponding to position 21 of the At.FT protein sequence (e.g., in place of proline or alanine); a phenylalanine at the position corresponding to position 44 of the At.FT protein sequence (e.g., in place of arginine or lysine); a histidine, glutamic acid, or aspartic acid at the position corresponding to position 57 of the At.FT protein sequence (e.g., in place of glycine); a glycine or alanine at the position corresponding to position 59 of the At.FT protein sequence (e.g., in place of glutamic acid or aspartic acid); a histidine at the position corresponding to position 85 of the At.FT protein sequence (e.g., in place of tyrosine); a lysine, arginine, alanine, or methionine at the position corresponding to position 109 of the At.FT protein sequence; a lysine or arginine at the position corresponding to position 128 of the At.FT protein sequence (e.g., in place of leucine); a glutamine or asparagine at the position corresponding to position 129 of the At.FT protein sequence (e.g., in place of glycine); a valine or cysteine at the position corresponding to position 132 of the At.FT protein sequence (e.g., in place of threonine); a lysine, arginine, or alanine at the position corresponding to position 134 of the At.FT protein sequence (e.g., in place of tyrosine); a proline at the position corresponding to position 135 of the At.FT protein sequence (e.g., in place of alanine or threonine); a serine, aspartic acid, glutamic acid, alanine, lysine, or arginine at the position corresponding to position 138 of the At.FT protein sequence (e.g., in place of tryptophan or methionine); a lysine or arginine at the position corresponding to position 140 of the At.FT protein sequence; a lysine or arginine at the position corresponding to position 146 of the At.FT protein sequence (e.g., in place of acidic or uncharged polar residues); a lysine or arginine at the position corresponding to position 152 of the At.FT protein sequence; and/or an alanine at the position corresponding to position 164 of the At.FT protein sequence (e.g., in place of cysteine or isoleucine). One skilled in the art would be able to identify corresponding amino acid positions and substitutions of other FT proteins based on their sequence alignment. Accordingly, embodiments of the present invention may exclude polynucleotides that encode FT-like proteins having one or more of the above amino acid substitutions associated with TFL or other anti-florigens. However, an FT protein may tolerate one or some of these amino acid substitutions while still maintaining florigenic activity.

A florigenic FT protein of the present invention may also be defined as being similar to a known FT protein in addition to having one or more of the above signature amino acid residues. For example, a florigenic protein may be defined as having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or least 99% identity to a sequence selected from the group consisting of SEQ ID NOs: 2, 4, 6, 8, 10, 12, 14, 16, 18, and 20, or a functional fragment thereof, in addition to one or more of the following signature residues: a tyrosine or other uncharged polar or nonpolar residue (e.g., alanine, tryptophan, methionine, leucine, threonine, cysteine, serine, or asparagine) at the amino acid position corresponding to position 85 of the At.FT protein sequence; a leucine or other nonpolar or hydrophobic residue (e.g., isoleucine, valine, or methionine) at the amino acid position corresponding to position 128 of the At.FT protein sequence; and/or a tryptophan or other large nonpolar or hydrophobic residue (e.g., methionine or phenylalanine) at the amino acid position corresponding to position 138 of the At.FT protein sequence. Such a florigenic FT protein may be further defined as having additional signature amino acid residue(s), such as one or more of the following: a glycine or other small nonpolar and uncharged residue (e.g., alanine, valine, leucine, isoleucine, or methionine) at the amino acid position corresponding to position 129 of the At.FT protein sequence; and/or a threonine at the amino acid position corresponding to position 132 of the At.FT protein sequence.

A florigenic FT protein of the present invention may also be defined as having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or least 99% identity to a sequence selected from the group consisting of SEQ ID NOs: 2, 4, 6, 8, 10, 12, 14, 16, 18, and 20, or a functional fragment thereof, but not having (i.e., excluding) one or more non-florigenic or anti-florigenic residues, such as one or more of the following: a histidine at the amino acid position corresponding to position 85 of the At.FT protein sequence; a lysine or arginine at the amino acid position corresponding to position 128 of the At.FT protein sequence; and/or a serine, aspartic acid, glutamic acid, lysine or arginine at the amino acid position corresponding to position 138 of the At.FT protein sequence. Such a florigenic FT protein may be further defined as not having (i.e., excluding) one or more additional residues, such as one or more of the following: a glutamine or asparagine at the amino acid position corresponding to position 129 of the At.FT protein sequence; and/or a valine or cysteine at the amino acid position corresponding to position 132 of the At.FT protein sequence.

Flowering Locus T (FT) genes play a key role in higher plants and function to integrate floral pathways. FT proteins have been shown to function as a mobile signal or florigen transported from leaves to the shoot apical apex where it triggers initiation of reproductive development in diverse species. See, e.g., Jaeger, K. E. et al., "Interlocking feedback loops govern the dynamic behavior of the floral transition in *Arabidopsis*," *The Plant Cell*, 25:820-833 (2013); Corbesier, L et al., "FT protein movement contributes to long distance signaling in floral induction of *Arabidopsis*," *Science* 316: 1030-1033 (2007); Jaeger, K E et al., "FT protein acts as a long range signal in *Arabidopsis,*" *Curr Biol* 17: 1050-1054 (2007); and Amasino, R. M. et al., "The Timing of Flowering," *Plant Physiology,* 154(2):516-520 (2010), the entire contents and disclosures of which are incorporated herein by reference. In *Arabidopsis,* FT protein binds to 14-3-3 and Flowering Locus D (FD) proteins in the meristem to form a flowering complex triggering activation of key floral meristem identity genes, such as APETATAL1 (AP1) and SOC1 at the shoot apex. See, e.g., Taoka, K. et al., "14-3-3 protein act as intracellular receptors for rice Hd3a florigen." *Nature* 476:332-335 (2011). The TERMINAL FLOWER 1 (TFL1) gene is a key repressor of FT targets that maintains the center of the shoot apical meristem (SAM) in a vegetative state. TFL1 acts by repressing the LEAFY (LFY) and AP1 genes. Thus, the relative concentrations of FT and TFL1 in the target tissues act competitively to control the timing of the reproductive transition of meristems from a vegetative state that may terminate further vegetative growth. See, e.g., Abe, M et al., *Science* 309: 1052-1055 (2005); and McGarry, R C et al., *Plant Science* 188/189: 71-81 (2012).

FT genes have been identified from many diverse species, and ectopic FT expression has been reported to induce early flowering. See, e.g., Kong, F. et al., "Two Coordinately Regulated Homologs of Flowering Locus T Are Involved in the Control of Photoperiodic Flowering in Soybean," *Plant Physiology* 154: 1220-1231 (2010); Turck, F. et al., "Regulation and identity of florigen: Flowering Locus T moves center stage," *Ann Rev Plant Biol* 59: 573-594 (2008); Blackman, B K et al., "The role of recently derived FT paralogs in sunflower domestication," *Curr Biol* 20: 629-635 (2010); Lifschitz, E. et al., "The tomato FT orthologs triggers systemic signals that regulate growth and flowering and substitute for diverse environmental stimuli," *PNAS* 103: 6398-6403 (2006); Trankner, C. et al., "Over-expression of an FT-homologous gene of apple induces early flowering in annual and perennial plants," *Planta* 232: 1309-1324 (2010); and Xiang, L. et al., "Functional analysis of Flowering Locus T orthologs from spring orchid (*Cymbidium goeringii* Rchb. f.) that regulates the vegetative to reproductive transition," *Plant Cell & Biochem* 58: 98-105 (2012), the entire contents and disclosures of which are incorporated herein by reference. However, prior studies with expression of FT transgenes used constitutive or tissue specific promoters that produced either very severe phenotypes, non-cell autonomous (systemic) phenotypes, or autonomous leaf specific phenotypes with plants or seedlings flowering earlier than controls and terminating at early stages of development. Given these findings, ectopic FT expression was generally not seen as a viable approach to increasing yield in plants by inducing flowers or altering flowering time.

According to embodiments of the present invention, a recombinant DNA molecule or polynucleotide is provided comprising a polynucleotide coding sequence encoding a FT protein that is operably linked to one or more promoter(s) and/or other regulatory element(s) that are operable in a plant cell to control or bias the timing and/or location of FT expression when transformed into a plant. As commonly understood in the art, the term "promoter" may generally refer to a DNA sequence that contains an RNA polymerase binding site, transcription start site, and/or TATA box and assists or promotes the transcription and expression of an associated transcribable polynucleotide sequence and/or gene (or transgene). A promoter may be synthetically produced, varied or derived from a known or naturally occurring promoter sequence or other promoter sequence (e.g., as provided herein). A promoter may also include a chimeric promoter comprising a combination of two or more heterologous sequences. A promoter of the present invention may thus include variants of promoter sequences that are similar in composition, but not identical to, other promoter sequence(s) known or provided herein. As used herein, the term "operably linked" refers to a functional linkage between a promoter or other regulatory element and an associated transcribable polynucleotide sequence or coding sequence of a gene (or transgene), such that the promoter, etc., operates to initiate, assist, affect, cause, and/or promote the transcription and expression of the associated coding or transcribable sequence, at least in particular tissue(s), developmental stage(s), and/or under certain condition(s).

A promoter may be classified according to a variety of criteria relating to the pattern of expression of a coding sequence or gene (including a transgene) operably linked to the promoter, such as constitutive, developmental, tissue-specific, inducible, etc. Promoters that initiate transcription in all or most tissues of the plant are referred to as "constitutive" promoters. Promoters that initiate transcription during certain periods or stages of development are referred to as "developmental" promoters. Promoters whose expression is enhanced in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. A promoter that expresses in a certain cell type of the plant is referred to as a "cell type specific" promoter. An "inducible" promoter is a promoter that initiates transcription in response to an environmental stimulus such as cold, drought or light, or other stimuli, such as wounding or chemical application. A promoter may also be classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed. The term "heterologous" may refer more broadly to a combination of two or more DNA molecules or sequences when such a combination is not normally found in nature.

According to embodiments of the present invention, a recombinant DNA molecule or polynucleotide is provided comprising a florigenic FT transgene or coding sequence operably linked to a promoter that functions in a plant, which may be introduced or transformed into a plant to cause the plant to have an altered flowering, reproductive and/or yield-related trait or phenotype. Since FT proteins are believed to operate in the meristems of a plant, including the apical and/or axillary meristems, to trigger floral transitioning of those meristems and induce flowering, embodiments of the present invention provide a recombinant DNA molecule comprising a FT transgene or coding sequence operably linked to a "vegetative stage" promoter to cause, when introduced or transformed into a plant, expression of the FT transgene earlier in the development of the plant (i.e., during the vegetative growth phase of the plant) to produce an increased level of FT in target tissues than would otherwise occur in a wild type plant at the same stage of development. Timing FT transgene expression during the vegetative stage(s) of development may be important for affecting one or more reproductive, flowering and/or yield-related traits or phenotypes by providing a timely inductive signal for the production of an increased number of floral meristems and successful flowers at one or more node(s) of the plant. Without being bound by any theory, vegetative stage expression of an FT transgene in a plant may operate to synchronize and/or increase early flowering at one or more node(s) to produce more flowers per node of the plant. The promoters described below as a part of the present invention provide options for timing FT expression.

As used herein, a "vegetative stage" promoter includes any promoter that initiates, causes, drives, etc., transcription or expression of its associated gene (or transgene) during one or more vegetative stage(s) of plant development, such as during one or more of Ve, Vc, V1, V2, V3, V4, etc., and/or any or all later vegetative stages of development (e.g., up to $V_n$ stage). Such a "vegetative stage" promoter may be further defined as a "vegetative stage preferred" promoter that initiates, causes, drives, etc., transcription or expression of its associated gene (or transgene) at least preferably or mostly, if not exclusively, during one or more vegetative stage(s) of plant development (as opposed to reproductive stages). However, a "vegetative stage" and a "vegetative stage preferred" promoter may each also permit, allow, cause, etc., transcription or expression of its associated gene (or transgene) during reproductive phase(s) of development in one or more cells or tissues of the plant. The features and characteristics of these vegetative stages for a given plant species are known in the art. For dicot plants, vegetative morphological features and characteristics of the plant during vegetative stages of development may include cotyledon form, vegetative meristems (apical, lateral/axillary, and root), leaf arrangement, leaf shape, leaf margin, leaf venation, petioles, stipules, *ochrea*, hypocotyl, and roots. According to embodiments of the present invention, a "vegetative stage" promoter may also be further defined by the particular vegetative stage during which observable or pronounced transcription or expression of its associated gene (or transgene) is first initiated. For example, a vegetative stage promoter may be a Vc stage promoter, a V1 stage promoter, a V2 stage promoter, a V3 stage promoter, etc. As such, a "Vc stage" promoter is defined as a vegetative stage promoter that first initiates transcription of its associated gene (or transgene) during the Vc stage of plant development, a "V1 stage" promoter is defined as a vegetative stage promoter that first initiates transcription of its associated gene (or transgene) during the V1 stage of plant development, a "V2 stage" promoter is defined as a vegetative stage promoter that first initiates transcription of its associated gene (or transgene) during the V2 stage of plant development, and so on, although expression of the associated gene (or transgene) may be present continuously or discontinuously in one or more tissues during later vegetative stage(s) of development. One skilled in the art would be able to determine the timing of expression of a given gene (or transgene) during plant development using various molecular assays and techniques known in the art.

According to embodiments of the present invention, a "vegetative stage" promoter may include a constitutive, tissue-preferred, or tissue-specific promoter. For example, a vegetative stage promoter may drive FT expression in one or more plant tissue(s), such as in one or more of the root(s), stem(s), leaf/leaves, meristem(s), etc., during a vegetative stage(s) of plant development. However, such a vegetative stage promoter may preferably drive expression of its associated FT transgene or coding sequence in one or more meristem(s) of the plant. According to many embodiments, a "vegetative stage" promoter may preferably be a "meristem-specific" or "meristem-preferred" promoter to cause expression of the FT transgene or coding sequence in meristematic tissue. FT proteins are known to operate in the meristems of a plant to help trigger the transition from vegetative to reproductive growth after translocation of the FT protein from the leaves. In contrast, embodiments of the present invention provide selective expression of an FT transgene directly in the meristem of a plant to induce flowering and cause the plant to adopt an altered reproductive and/or yield-related trait or phenotype. Thus, according to embodiments of the present invention, a recombinant DNA molecule is provided comprising an FT transgene or coding sequence operably linked to a "meristem-specific" or "meristem-preferred" promoter that drives expression of the FT transgene at least preferentially in one or more meristematic tissues of a plant when transformed into the plant. As used herein, "meristem-preferred promoter" refers to promoters that preferentially cause expression of an associated gene or transgene in at least one meristematic tissue of a plant relative to other plant tissues, whereas a "meristem-specific promoter" refers to promoters that cause expression of an associated gene or transgene exclusively (or almost exclusively) in at least one meristem of a plant.

Recent work using artificial early "short day" light treatments during vegetative stages of development revealed that flowering time could be altered in a way that alters one or more yield-related traits or phenotypes (e.g., by causing an increased number of pods or seeds per node on a plant) and that the effect of these treatments was dosage-dependent with the number of flowers, seeds and/or pods per plant (and/or per node of the plant) depending on (i) the duration of the short day exposure (i.e., floral induction signal dosage) and (ii) the length of the post-short day photoperiods under long day conditions (i.e., the dosage or length of the vegetative growth inducing signal after the short day induction signal). See, e.g., U.S. Pat. No. 8,935,880 and U.S. Patent Application Publication No. 2014/0259905, introduced above. Soybean plants experiencing a lower or less prolonged early short day induction (eSDI) treatment (prior to returning to long day growing conditions) had more flowers, pods and seeds per plant with more normal plant height and maturity, whereas soybean plants exposed to a greater or more prolonged eSDI treatment produced shorter, earlier-terminating plants with fewer pods and seeds per plant (albeit perhaps with an increased number of pods and/or seeds per node).

Without being bound by any theory, it is proposed that an early florigenic signal (e.g., short days for soybean and other SD plants) triggers an early vegetative to reproductive transition of plants and even termination of a subset of its primary meristems. However, by returning those plants to non-inductive growth conditions (e.g., long days for SD plants) after the initial SD signal, the remaining meristematic reserves of the plant may be preserved and reproductive and/or flowering duration may be extended or maintained, thus allowing for the successful development of a greater number of productive flowers, pods and/or seeds per node (and/or per plant) during the reproductive phase. With early floral induction, a greater overlap may also be created between reproductive development and vegetative growth of the plant, which may further promote or coincide with an extended reproductive and/or flowering duration. For purposes of the present invention, "reproductive duration" refers to the length of time from the initiation of flowering until the end of seed/pod development and/or filling, whereas "flowering duration" or "duration of flowering" refers the length of time from the appearance of the first open flower until the last open flower closes. By returning to non-inductive growth conditions after early floral induction, more abundant resources may be available and directed toward the production of an increased number of successful (i.e., non-aborting) flowers, pods and/or seeds per plant, unlike normal floral development in short day plants, which may coincide with declining plant resources due to termination of meristematic growth and maturation of the plant.

However, in addition to early flowering, a floral induction signal (e.g., early short day conditions) also causes early termination of the plant. Therefore, it is proposed that an optimal dosage and timing of the floral induction signal may be needed to maximize yield by balancing (i) the early vegetative to reproductive transition and/or synchronization of flowering with the early floral induction signal (leading to potential yield gains at each node of the plant) against (ii) earlier growth termination (leading to smaller plants with fewer internodes, less branching, and fewer nodes and/or flowers per plant). It is believed that lower dosages of a floral induction signal may be sufficient to induce flowering while lessening or minimizing earlier termination of the plant, such that larger plants are produced with increased numbers of flowers, pods and/or seeds per node (and/or per plant). On the other hand, higher dosages of a floral induction signal may cause early termination of the plant (in addition to early flowering) to produce smaller plants with relatively fewer numbers of flowers, pods and/or seeds per plant due to the smaller plant size with fewer internodes and/or branches per plant, despite having perhaps a greater number of flowers, pods and/or seeds per node (and/or per plant) relative to wild-type or control plants under normal growth conditions. As stated above, these effects of ectopic FT expression may also include an increased number of bolls, siliques, fruits, nuts, tubers, etc., per node (and/or per plant), depending on the particular plant species.

As mentioned above, the short day induction phenotype in soybean was used to screen for genes having altered expression in those plants through transcriptional profiling. These studies led to the identification of an endogenous FT gene, Gm.FT2a, having increased expression in response to the short day induction treatment. Accordingly, it is presently proposed that expression of a florigenic FT transgene can be used as a floral induction signal to cause early flowering and increased flowers, pods and/or seeds per node (and/or per plant) relative to a wild type or control plant not having the FT transgene. According to embodiments of the present invention, appropriate control of the timing, location and dosage of florigenic FT expression during vegetative stages of development can be used to induce flowering and produce plants having increased flowers, pods and/or seeds per node relative to a wild type or control plant not having the FT transgene. Rather than attempting to transiently express FT and recapitulate the timing of the eSDI treatments, it is proposed that FT could be weakly expressed in the vegetative meristem to provide the early floral induction signal. Accordingly, a promoter from the Erecta gene (pErecta or pEr) having weak meristematic expression during vegetative stages of development was selected for initial testing with a Gm.FT2a transgene. However, given that prior studies showed that constitutive FT expression produced plants having a severe, early termination phenotype, and further that the site of action for FT produced peripherally and translocated from the leaves is in the meristem, it was possible that direct meristematic expression of FT could produce even more potent and severe phenotypes (and/or non-viable plants) relative to constitutive FT expression.

The effects of Gm.FT2a overexpression were immediately seen in $R_0$ transformed soybean plants, which had early flowering, reduced seed yield (e.g., only about 8 seeds/plant), and very early termination, suggesting that the balance between floral induction and floral repression/vegetative growth was strongly in favor of flowering and early termination. However, enough R1 seed was salvaged from these plants to allow for additional experiments to be performed. It was proposed that growing the $R_1$ soybean seed under long day (floral repressive) photoperiod conditions in the greenhouse might delay the early flowering and termination phenotypes observed in the $R_0$ plants. Given the theorized dosage response, it was further proposed that segregating FT2a homozygous, hemizygous and null soybean plants could be tested together in the greenhouse to evaluate the dosage response resulting from FT overexpression. In these experiments (as described further below), it was observed that segregating plants did have different phenotypes: null plants were similar to wild-type plants in terms of plant architecture and pods per node (and per plant), while homozygous plants terminated early with a severe dwarf phenotype (although possibly with an increased number of pods per node). However, hemizygous plants were almost as large as null or wild-type plants but exhibited the hyper-flowering phenotype with an increased number of pods per node (and/or per plant). These findings show that vegetative stage and/or meristematic expression of a florigenic FT transgene may be used to produce a high yielding plant (similar to the eSDI treatment), and that the effect of FT expression is dosage-dependent since soybean plants hemizygous for the FT2a transgene under the control of a weak meristematic promoter displayed the high yield phenotype of increased pods per node without the more severe early termination and short plant height phenotypes observed with homozygous FT2a plants when grown under long day (vegetative) conditions.

Interestingly, however, increased numbers of pods per node was often observed independently of reproductive (R1-R7) duration under greenhouse conditions and was not perfectly correlated with early flowering among the FT transgenes tested, although it is possible that the duration of flowering may still be prolonged in some cases (at least during one or more reproductive stages) even if the total reproductive duration is not significantly changed relative to control plants. Without being bound by any theory, it is believed that increased numbers of pods per node in transgenic FT plants may result at least in part from an increase in the number of inflorescence and floral meristems induced from vegetative shoot apical and axillary meristems at each of the affected node(s), which may give rise to a greater number of flowers and/or released floral racemes at those node(s). Such an increase in the number of floral meristems induced at each node of the plant in response to FT overexpression may operate through one or more mechanisms or pathways, which may be independent of flowering time and/or reproductive duration. However, meristematic changes may be microscopic at first, and thus not observed to cause "early flowering" at such stage by simple visual inspection even though reproductive changes to the meristem may have already begun to occur.

Without being bound by any theory, early vegetative FT expression may cause more reproductive meristems to form and develop earlier than normal at one or more node(s) of the transgenic plant. These reproductive meristems may then allow or cause a greater number of floral racemes to form and elongate with flowers at each node. On the other hand, it is further theorized that later expression of FT during reproductive stages may function to repress further floral development at each node. Thus, later developing flowers within the respective raceme may become terminated, and thus more of the plant's resources may be directed to the earlier developing flowers within the raceme to more effectively produce full-sized pods. Accordingly, it is contemplated that by (i) forming a greater number of inflorescence and floral meristems at each node by early FT induction, and then (ii) directing more plant resources to the earlier, more developed flowers within each of the racemes by termination of the later-developing flowers, increased synchronization of floral development may occur with a greater number of mature pods being formed per node of the plant.

According to embodiments of the present invention, a recombinant DNA molecule is provided comprising an FT coding sequence operatively linked to a vegetative stage promoter, which may also be a meristem-preferred and/or meristem-specific promoter. For example, the promoter may include the pAt.Erecta promoter from *Arabidopsis* (SEQ ID NO: 21), or a functional fragment or portion thereof. Two examples of a truncated portion of the pAt.Erecta promoter according to embodiments of the present invention are provided as SEQ ID NO: 22 and SEQ ID NO: 38. See, e.g., Yokoyama, R. et al., "The *Arabidopsis* ERECTA gene is expressed in the shoot apical meristem and organ primordia," *The Plant Journal* 15(3): 301-310 (1998). pAt.Erecta is an example of a vegetative stage promoter that is also meristem-preferred. Other vegetative stage, meristem-preferred or meristem-specific promoters have been identified based on their characterized expression profile (see, e.g., Examples 4 and 7 below) that may also be used to drive FT expression according to embodiments of the present invention. For example, the following soybean receptor like kinase (RLK) genes were identified that could be used as vegetative stage, meristem-preferred promoters: Glyma10g38730 (SEQ ID NO: 23), Glyma09g27950 (SEQ ID NO: 24), Glyma06g05900 (SEQ ID NO: 25), and Glyma17g34380 (SEQ ID NO: 26). Vegetative stage, meristem-preferred promoters according to embodiments of the present invention may also include receptor like kinase (RLK) gene promoters from potato: PGSC0003DMP400032802 (SEQ ID NO: 27) and PGSC0003DMP400054040 (SEQ ID NO: 28). Given the characterization provided herein of the pAt.Erecta promoter driving FT expression and the similar expression profiles identified for other RLK, Erecta or Erecta-like (Erl) genes, vegetative-stage, meristem-preferred or meristem-specific promoters of the present invention may further comprise any known or later identified promoter sequences of RLK, Erecta and Erecta-like genes from other dicotyledonous species having vegetative-stage pattern of expression in the meristems of plants.

Additional examples of vegetative stage, meristem-preferred or meristem-specific promoters may include those from the following *Arabidopsis* genes: Pinhead (At.PNH) (SEQ ID NO: 29), *Angustifolia* 3 or At.AN3 (SEQ ID NO: 30), ALMYB17 (At.LMI2 or Late Meristem Identity 2; At3g61250) (SEQ ID NO: 31), Kinesin-like gene (At5g55520) (SEQ ID NO: 32), AP2/B3-like genes, including ALREM17 (SEQ ID NO: 33) or ALREM19, and Erecta-like 1 and 2 genes, At.Erl1 (SEQ ID NO: 34) and At.Erl2 (SEQ ID NO: 35), and functional portions thereof. The polynucleotide sequence of these promoters (or a functional fragment thereof) may also have a relaxed sequence identity while still maintaining a similar or identical pattern of expression of an associated gene or transgene operably linked to the promoter. For example, the promoter may comprise a polynucleotide sequence that is at least 85%, at least 90%, at least 91%, at least 92%, at least 93%, at least 94%, at least 95%, at least 96%, at least 97%, at least 98%, or least 99% identical to a polynucleotide sequence selected from the above SEQ ID NOs: 21, 22, 23, 24, 25, 26, 27, 28, 29, 30, 31, 32, 33, 34, or 35, or a functional portion thereof. A "functional portion" of a known or provided promoter sequence is defined as one or more continuous or discontinuous portion(s) of the known or provided promoter sequence that may functionally drive, cause, promote, etc., expression of its associated gene (or transgene) in a manner that is identical or similar to the known or provided promoter sequence. Based on the present disclosure, one skilled in the art would be able to determine if a promoter comprising one or more portion(s) of a known or provided promoter sequence, and/or having a shorter sequence and/or more relaxed sequence identity relative to a known or provided promoter sequence, causes a similar pattern of expression and/or similar phenotypes or effects when its associated FT transgene is expressed in a plant as compared to the known or provided promoter sequence.

As stated above, a recombinant DNA molecule of the present invention may generally comprise an FT transgene or expression cassette including a polynucleotide sequence encoding an FT protein that is operatively linked to a vegetative stage promoter, which may also be a meristem-preferred or meristem-specific promoter. The polynucleotide coding sequence of the FT transgene or expression cassette may also be operatively linked to one or more additional regulatory element(s), such as an enhancer(s), leader, transcription start site (TSS), linker, 5' and 3' untranslated region(s), intron(s), polyadenylation signal, termination region or sequence, etc., that are suitable or necessary for regulating or allowing expression of the FT transgene or cassette to effectively produce an FT protein in a plant cell. Such additional regulatory element(s) may be optional and used to enhance or optimize expression of the transgene. For purposes of the present invention, an "enhancer" may be distinguished from a "promoter" in that an enhancer typically lacks a transcription start site, TATA box, or equivalent sequence and is thus insufficient alone to drive transcription. As used herein, a "leader" may be defined generally as the DNA sequence of the untranslated 5' region (5' UTR) of a gene (or transgene) between the transcription start site (TSS) and the protein coding sequence start site.

According to embodiments of the present invention, the term "recombinant" in reference to a DNA molecule, construct, vector, etc., refers to a DNA molecule or sequence that is not found in nature and/or is present in a context in which it is not found in nature, including a DNA molecule, construct, etc., comprising a combination of DNA sequences that would not naturally occur contiguously or in close proximity together without human intervention, and/or a DNA molecule, construct, etc., comprising at least two DNA sequences that are heterologous with respect to each other. A recombinant DNA molecule, construct, etc., may comprise DNA sequence(s) that is/are separated from other polynucleotide sequence(s) that exist in proximity to such DNA sequence(s) in nature, and/or a DNA sequence that is adjacent to (or contiguous with) other polynucleotide sequence(s) that are not naturally in proximity with each other. A recombinant DNA molecule, construct, etc., may also refer to a DNA molecule or sequence that has been genetically engineered and constructed outside of a cell. For example, a recombinant DNA molecule may comprise any suitable plasmid, vector, etc., and may include a linear or circular DNA molecule. Such plasmids, vectors, etc., may contain various maintenance elements including a prokaryotic origin of replication and selectable marker, as well as a FT expressing transgene or expression cassette perhaps in addition to a plant selectable marker gene, etc.

As introduced above, the florigenic effects of FT expression may be opposed by the activity of various other anti-florigenic (or non-florigenic) proteins, such as Terminal Flower (TFL) genes, in the meristem of a plant. Flowering time and duration may thus be seen as a balance between florigenic and anti-florigenic signals present within the meristem(s) of a plant. Accordingly, it is further proposed that flowering time in a plant may be altered or induced by suppression of one or more anti-florigenic genes during vegetative stages of development to render the vegetative meristem more responsive to a florigenic signal. In soybean, for example, genes related to *Arabidopsis* TFL1 are primarily expressed in floral meristems where they oppose the functions of florigenic signals to regulate developmental decisions like stem growth habit. In particular, the TFL1-like genes, TFL1a and TFL1b, in soybean are expressed in the shoot apical meristem, and allelic diversity in TFL1b may be largely responsible for changes in stem growth habit in soy resulting in determinate or indeterminate growth. See, e.g., Liu, B. et al., "The soybean stem growth habit gene Dt1 is an ortholog of *Arabidopsis* TERMINAL FLOWER 1." *Plant Physiol* 153(1):198-210 (2010). Accordingly, suppressing the expression of TFL or another anti-florigenic protein in the meristem of a dicot plant may result in increased sensitivity of those meristematic tissues to florigenic signals, such as FT, resulting in early flowering and increased pods per node, similarly to overexpression of FT in these tissues.

Thus, it is contemplated that a recombinant DNA molecule of the present invention may further comprise a suppression construct having a transcribable DNA sequence operatively linked to a vegetative stage promoter, which may also be a meristem-preferred or meristem-specific promoter, wherein the transcribable DNA sequence encodes an RNA molecule that causes targeted suppression of an endogenous anti-florigenic gene, such as a TFL gene. Various methods for suppressing the expression of an endogenous gene are known in the art.

According to another broad aspect of the present invention, methods are provided for transforming a plant cell, tissue or explant with a recombinant DNA molecule or construct comprising an FT transgene or expression cassette to produce a transgenic plant. Numerous methods for transforming chromosomes in a plant cell with a recombinant DNA molecule are known in the art, which may be used according to methods of the present invention to produce a transgenic plant cell and plant. Any suitable method or technique for transformation of a plant cell known in the art may be used according to present methods. Effective methods for transformation of plants include bacterially mediated transformation, such as *Agrobacterium*-mediated or *Rhizobium*-mediated transformation, and microprojectile bombardment-mediated transformation. A variety of methods are known in the art for transforming explants with a transformation vector via bacterially mediated transformation or microprojectile bombardment and then subsequently culturing, etc, those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods may be chimeric or non-chimeric for the transformation event depending on the methods and explants used. Methods are further provided for expressing an FT transgene in one or more plant cells or tissues under the control of a vegetative-stage promoter, which may also be a meristem-preferred or meristem-specific promoter. Such methods may be used to alter flowering time of a plant and/or the number of productive or successful flowers, fruits, pods, and/or seeds per node of the plant relative to a wild type or control plant not having the FT transgene. Indeed, methods of the present invention may be used to alter reproductive or yield-related phenotype(s) or trait(s) of the transgenic plant.

Transformation of a target plant material or explant may be practiced in tissue culture on nutrient media, for example a mixture of nutrients that allow cells to grow in vitro. Recipient cell targets or explants may include, but are not limited to, meristems, shoot tips, protoplasts, hypocotyls, calli, immature or mature embryos, shoots, buds, nodal sections, leaves, gametic cells such as microspores, pollen, sperm and egg cells, etc., or any suitable portions thereof. It is contemplated that any transformable cell or tissue from which a fertile plant can be regenerated or grown/developed may be used as a target for transformation. Transformed explants, cells or tissues may be subjected to additional culturing steps, such as callus induction, selection, regeneration, etc., as known in the art. Transformed cells, tissues or explants containing a recombinant DNA insertion may be grown, developed or regenerated into transgenic plants in culture, plugs or soil according to methods known in the art. Transgenic plants may be further crossed to themselves or other plants to produce transgenic seeds and progeny. A transgenic plant may also be prepared by crossing a first plant comprising the recombinant DNA sequence or transformation event with a second plant lacking the insertion. For example, a recombinant DNA sequence may be introduced into a first plant line that is amenable to transformation, which may then be crossed with a second plant line to introgress the recombinant DNA sequence into the second plant line. Progeny of these crosses can be further back crossed into the more desirable line multiple times, such as through 6 to 8 generations or back crosses, to produce a progeny plant with substantially the same genotype as the original parental line but for the introduction of the recombinant DNA sequence.

A recombinant DNA molecule or construct of the present invention may be included within a DNA transformation vector for use in transformation of a target plant cell, tissue or explant. Such a transformation vector of the present invention may generally comprise sequences or elements necessary or beneficial for effective transformation in addition to the FT expressing transgene or expression cassette. For *Agrobacterium*-mediated transformation, the transformation vector may comprise an engineered transfer DNA (or T-DNA) segment or region having two border sequences, a left border (LB) and a right border (RB), flanking at least the FT expressing transgene or expression cassette, such that insertion of the T-DNA into the plant genome will create a transformation event for the FT transgene or expression cassette. In other words, the FT transgene or expression cassette would be located between the left and right borders of the T-DNA, perhaps along with an additional transgene(s) or expression cassette(s), such as a plant selectable marker transgene and/or other gene(s) of agronomic interest that may confer a trait or phenotype of agronomic interest to a plant. In addition to protein encoding sequences, a gene of agronomic interest may further comprise a polynucleotide sequence encoding a RNA suppression element. According to alternative embodiments, the FT transgene or expression cassette and the plant selectable marker transgene (or other gene of agronomic interest) may be present in separate T-DNA segments on the same or different recombinant DNA molecule(s), such as for co-transformation. A transformation vector or construct may further comprise prokaryotic maintenance elements, which for *Agrobacterium*-mediated transformation may be located in the vector backbone outside of the T-DNA region(s).

A plant selectable marker transgene in a transformation vector or construct of the present invention may be used to assist in the selection of transformed cells or tissue due to the presence of a selection agent, such as an antibiotic or herbicide, wherein the plant selectable marker transgene provides tolerance or resistance to the selection agent. Thus, the selection agent may bias or favor the survival, development, growth, proliferation, etc., of transformed cells expressing the plant selectable marker gene, such as to increase the proportion of transformed cells or tissues in the $R_0$ plant. Commonly used plant selectable marker genes include, for example, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or EPSPS). Plant screenable marker genes may also be used, which provide an ability to visually screen for transformants, such as luciferase or green fluorescent protein (GFP), or a gene expressing a beta glucuronidase or uidA gene (GUS) for which various chromogenic substrates are known.

According to embodiments of the present invention, methods for transforming a plant cell, tissue or explant with a recombinant DNA molecule or construct may further include site-directed or targeted integration. According to these methods, a portion of a recombinant DNA donor template molecule (i.e., an insertion sequence) may be inserted or integrated at a desired site or locus within the plant genome. The insertion sequence of the donor template may comprise a transgene or construct, such as an FT transgene or construct comprising a polynucleotide sequence encoding a florigenic FT protein operatively linked to a vegetative-stage promoter, which may also be a meristem-preferred or meristem-specific promoter. The donor template may also have one or two homology arms flanking the insertion sequence to promote the targeted insertion event through homologous recombination and/or homology-directed repair. Thus, a recombinant DNA molecule of the present invention may further include a donor template for site-directed or targeted integration of a transgene or construct, such as an FT transgene or construct, into the genome of a plant.

Any site or locus within the genome of a plant may potentially be chosen for site-directed integration of a transgene or construct of the present invention. For site-directed integration, a double-strand break (DSB) or nick may first be made at a selected genomic locus with a site-specific nuclease, such as, for example, a zinc-finger nuclease, an engineered or native meganuclease, a TALE-endonuclease, or an RNA-guided endonuclease (e.g., Cas9 or Cpf1). Any method known in the art for site-directed integration may be used. In the presence of a donor template molecule, the DSB or nick may then be repaired by homologous recombination between the homology arm(s) of the donor template and the plant genome, or by non-homologous end joining (NHEJ), resulting in site-directed integration of the insertion sequence into the plant genome to create the targeted insertion event at the site of the DSB or nick. Thus, site-specific insertion or integration of a transgene or construct may be achieved.

According to embodiments of the present invention, a plant that may be transformed with a recombinant DNA molecule or transformation vector comprising an FT transgene may include a variety of flowering plants or angiosperms, which may be further defined as including various dicotyledonous (dicot) plant species, such as soybean, cotton, alfalfa, canola, sugar beets, alfalfa and other leguminous plants. A dicot plant could be a member of the *Brassica* sp. (e.g., *B. napus*, *B. rapa*, *B. juncea*), particularly those *Brassica* species useful as sources of seed oil, alfalfa (*Medicago sativa*), sunflower (*Helianthus annuus*), safflower (*Carthamus tinctorius*), oil palm (*Elaeis* spp.), sesame (*Sesamum* spp.), coconut (*Cocos* spp.), soybean (*Glycine max*), tobacco (*Nicotiana tabacum*), potato (*Solanum tuberosum*), peanuts (*Arachis hypogaea*), cotton (*Gossypium barbadense*, *Gossypium hirsutum*), sweet potato (*Ipomoea batatus*), cassava (*Manihot esculenta*), coffee (*Coffea* spp.), tea (*Camellia* spp.), fruit trees, such as apple (*Malus* spp.), *Prunus* spp., such as plum, apricot, peach, cherry, etc., pear (*Pyrus* spp.), fig (*Ficus casica*), banana (*Musa* spp.), etc., citrus trees (*Citrus* spp.), cocoa (*Theobroma cacao*), avocado (*Persea americana*), olive (*Olea europaea*), almond (*Prunus amygdalus*), walnut (*Juglans* spp.), strawberry (*Fragaria* spp.), watermelon (*Citrullus lanatus*), pepper (*Capsicum* spp.), sugar beet (*Beta vulgaris*), grape (*Vitis, Muscadinia*), tomato (*Lycopersicon esculentum*, *Solanum lycopersicum*), and cucumber (*Cucumis sativis*). Leguminous plants include beans and peas. Beans include, for example, guar, locust bean, fenugreek, soybean, garden beans, cowpea, mungbean, lima bean, fava bean, lentils, and chickpea. Given that the present invention may apply to a broad range of plant species, the present invention further applies to other botanical structures analogous to pods of leguminous plants, such as bolls, siliques, fruits, nuts, tubers, etc. According to embodiments of the present invention and depending on the particular plant species transformed, a plant ectopically expressing a florigenic FT sequence may have an altered or greater number of bolls, siliques, fruits, nuts, tubers, etc., per node(s), main stem, and/or branch(es) of the plant, and/or an altered or greater number of bolls, siliques, fruits, nuts, tubers, etc., per plant, relative to a wild type or control plant not having the FT transgene.

According to another broad aspect of the present invention, a transgenic plant(s), plant cell(s), seed(s), and plant part(s) are provided comprising a transformation event or insertion into the genome of at least one plant cell thereof, the transformation event or insertion comprising a recombinant DNA sequence, construct or polynucleotide including a Flowering Locus T (FT) transgene or expression cassette, wherein the FT transgene or expression cassette further comprises a polynucleotide sequence encoding an FT protein operably linked to a vegetative stage promoter, which may also be a meristem-preferred or meristem-specific promoter. The FT protein encoded by the polynucleotide sequence may be native to the transgenic plant transformed with the polynucleotide sequence, or homologous or otherwise similar to a FT protein native to the transgenic plant (i.e., not native to the transgenic plant). Such a transgenic plant may be produced by any suitable transformation method, which may be followed by selection, culturing, regeneration, development, etc., as desired or needed to produce a transgenic $R_0$ plant, which may then be selfed or crossed to other plants to generate R1 seed and subsequent progeny generations and seed through additional crosses, etc. Similarly, embodiments of the present invention further include a plant cell, tissue, explant, etc., comprising one or more transgenic cells having a transformation event or genomic insertion of a recombinant DNA or polynucleotide sequence comprising an FT transgene.

Transgenic plants, plant cells, seeds, and plant parts of the present invention may be homozygous or hemizygous for a transgenic event or insertion of an FT transgene or expression cassette into the genome of at least one plant cell thereof, or may contain any number of copies of a transgenic event(s) or insertion(s) comprising an FT transgene or expression cassette. The dosage or amount of expression of an FT transgene or expression cassette may be altered by its zygosity and/or number of copies, which may affect the degree or extent of phenotypic changes in the transgenic plant, etc. According to some embodiments, a transgenic plant comprising an FT transgene may be further characterized as having one or more altered flowering or reproductive phenotypes or traits, which may include altered yield-related phenotypes or traits, such as an increase in the number of flowers, pods, etc., and/or seeds per plant (and/or per node of the plant) relative to a wild type or control plant not having the FT transgene. Such a transgenic plant may be further characterized as having an altered structure, morphology, and/or architecture due to altered plant height, branching patterns, number of floral nodes, etc., relative to a wild type or control plant. Indeed, yield-related phenotypes or traits altered by FT overexpression in a transgenic plant may include: flowering time, reproductive duration, flowering duration, amount or timing of abscission of flowers, pods, siliques, bolls, fruits, nuts, etc., number of flowers per node, number of racemes per node, number of branches, number of nodes per plant, number of nodes on the main stem, number of nodes on branches, number of pods, bolls, siliques, fruits, nuts, etc., per plant, number of pods, bolls, siliques, fruits, nuts, etc., per node, number of pods on the main stem, number of pods, bolls, siliques, fruits, nuts, etc., on branches, 1000 seed weight, number of seeds per plant, number of seeds per node, and/or altered plant architecture, as compared to a wild type or control plant not having the FT transgene.

For purposes of the present invention, a "plant" may include an explant, seedling, plantlet or whole plant at any stage of regeneration or development. As used herein, a "transgenic plant" refers to a plant whose genome has been altered by the integration or insertion of a recombinant DNA molecule, construct or sequence. A transgenic plant includes an $R_0$ plant developed or regenerated from an originally transformed plant cell(s) as well as progeny transgenic plants in later generations or crosses from the $R_0$ transgenic plant. As used herein, a "plant part" may refer to any organ or intact tissue of a plant, such as a meristem, shoot organ/structure (e.g., leaf, stem and tuber), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, ground tissue, and the like), or any portion thereof. Plant parts of the present invention may be viable, nonviable, regenerable, and/or non-regenerable. A "propagule" may include any plant part that is capable of growing into an entire plant. For purposes of the present invention, a plant cell transformed with an FT transgene according to embodiments of the present invention may include any plant cell that is competent for transformation as understood in the art based on the method of transformation, such as a meristem cell, an embryonic cell, a callus cell, etc. As used herein, a "transgenic plant cell" simply refers to any plant cell that is transformed with a stably-integrated recombinant DNA molecule or sequence. A transgenic plant cell may include an originally-transformed plant cell, a transgenic plant cell of a regenerated or developed $R_0$ plant, or a transgenic plant cell from any progeny plant or offspring of the transformed $R_0$ plant, including cell(s) of a plant seed or embryo, or a cultured plant or callus cell, etc.

Embodiments of the present invention may further include methods for making or producing transgenic plants having altered reproductive and/or yield-related traits or phenotypes, such as by transformation, crossing, etc., wherein the method comprises introducing a recombinant DNA molecule or sequence comprising an FT transgene into a plant cell, and then regenerating or developing the transgenic plant from the transformed plant cell, which may be performed under selection pressure favoring the transgenic event. Such methods may comprise transforming a plant cell with a recombinant DNA molecule or sequence comprising an FT transgene, and selecting for a plant having one or more altered phenotypes or traits, such as one or more of the following: flowering time, reproductive duration, flowering duration, amount or timing of abscission of flowers, pods, bolls, siliques, fruits, nuts, etc., number of flowers per node, number of racemes per node, number of branches, number of nodes per plant, number of nodes on the main stem, number of nodes on branches, number of pods, bolls, siliques, fruits, or nuts per plant, number of pods, bolls, siliques, fruits, nuts, etc., per node, number of pods, bolls, siliques, fruits, nuts, etc., on the main stem, number of pods, bolls, siliques, fruits, nuts, etc., on branches, 1000 seed weight, number of seeds per plant, number of seeds per node, and altered plant architecture, as compared to a wild type or control plant not having the FT transgene. For example, embodiments of the present invention may comprise methods for producing a transgenic plant having an increased number of flowers, pods, and/or seeds per plant (and/or an increased number of flowers, pods, and/or seeds per node of the plant), wherein the method comprises introducing a recombinant DNA molecule comprising an FT transgene into a plant cell, and then regenerating or developing the transgenic plant from the plant cell.

According to another broad aspect of the present invention, methods are provided for planting a transgenic plant(s) of the present invention at a normal or high density in field. According to some embodiments, the yield of a crop plant per acre (or per land area) may be increased by planting a transgenic plant(s) of the present invention at a higher density in the field. As described herein, transgenic plants of the present invention expressing a florigenic FT protein during vegetative stage(s) of development may exhibit increased pods per node (particularly on the main stem), but may also have an altered plant architecture with reduced branching and fewer nodes per branch. Thus, it is proposed that transgenic plants of the present invention may be planted at a higher density to increase yield per acre in the field. For row crops, higher density may be achieved by planting a greater number of seeds/plants per row length and/or by decreasing the spacing between rows. According to some embodiments, a transgenic crop plant of the present invention may be planted at a density in the field (plants per land/field area) that is at least 5%, 10%, 15%, 20%, 25%, 50%, 75%, 100%, 125%, 150%, 175%, 200%, 225%, or 250% higher than a normal planting density for that crop plant according to standard agronomic practices.

For soybean, the typical planting density is in a range from about 100,000 to 150,000 seeds per acre, and the typical row spacing is in a range from about 26 to about 40 inches, such as 30 inch or 36 inch row spacing. Within a given row, about 6-8 soybean seeds may typically be planted per foot. In contrast, high density planting for soybean may include a range of approximately 150,000 to 250,000 seeds per acre, and the row spacing may be within a range from about 10 inches or less to about 25 inches, such as 10 inch, 15 inch or 20 inch row spacing. For high density planting, approximately 9-12 soybean seeds per foot may be planted within each row, perhaps in combination with narrower row spacing. However, high crop density may be achieved by narrow row spacing without an increase in planting density within each row.

For cotton, the typical planting density is in a range from about 28,000 to 45,000 seeds per acre, and the typical row spacing is in a range from about 38 to about 40 inches, such as 38 inch or 40 inch row spacing. Within a given row, about 2-3 cotton seeds may typically be planted per foot. In contrast, high density planting for soybean may include a range of approximately 48,000 to 60,000 seeds per acre, and the row spacing may be within a range from about 30 inches or less to about 36 inches. For high density planting, approximately 3-5 cotton seeds per foot may be planted within each row, perhaps in combination with narrower row spacing. However, high crop density for cotton may be achieved by narrow row spacing without an increase in planting density within each row.

For canola, the typical planting density is in a range from about 360,000 to 550,000 seeds per acre, and the typical row spacing between openers is in a range from about 6 inches to about 16 inches. Within a given row, about 8-12 canola seeds may typically be planted per foot. In contrast, high density planting for soybean may include a range of approximately 450,000 to 680,000 seeds per acre, and the row spacing may be within a range from about 5 inches or less to about 10 inches. For high density planting, approximately 10-16 canola seeds per foot may be planted within each row, perhaps in combination with the narrower row spacing. However, high crop density for canola may be achieved by narrow row spacing without an increase in planting density within each row.

EXAMPLES

Example 1. Soybean Short Day Induction Treatment and Identification of Flowering Locus T (FT) Genes by Transcriptional Profiling Methods for the photoperiodic light treatment (i.e., short day induction of flowering in plants) are described in U.S. Pat. No. 8,935,880 and U.S. Patent Application Publication No. 2014/0259905, which are incorporated herein by reference in their entirety. As described further therein, the early short day induction treatment produced soybean plants having altered reproductive traits including an increased number of pods/seeds per plant. Transcriptional profiling experiments were performed using gene expression microarrays to determine if particular transcripts were up-regulated in these light-induced plants to identify genes that may be responsible for mediating the short day induction phenotypes. In these experiments, an analysis of transcripts was conducted on soybean leaf and floral apex tissues collected after 1, 3 and 5 days from plants that received a short day inductive light treatment (Short day) in comparison to tissues from plants that did not receive the inductive treatment (Long day).

As shown in FIG. 2, an increased accumulation of transcripts was observed for a particular Flowering Locus T gene, Gm.FT2a (SEQ ID NO: 1), in leaf tissue harvested at 3 and 5 days after the early short day induction (eSDI) treatment in comparison to samples taken from either (i) floral apex tissues of the same short day induction plants, or (ii) leaf tissues and floral apex tissues of soybean plants that instead received the long day treatment. These data support the conclusion that Gm.FT2a expression is induced in leaf tissue of plants experiencing the eSDI treatment, which was not seen in plants grown under long day conditions. Gm.FT2a expression was also not observed in the floral apex of eSDI treated plants, which is consistent with the model of FT protein expression being induced in peripheral leafy tissues in response to inductive photoperiod conditions and then migrating to its site of action in the meristems to induce flowering. However, additional experiments using a more sensitive RNA sequencing analysis of transcripts did show some Gm.FT2a induction in the shoot apex and axillary buds in response to the eSDI treatment (data not shown).

Example 2. Characterization of the pAt.Erecta Promoter Expression Patterns in Soybean Achieving desirable traits or phenotypes by transgenic approaches may require control of the temporal and spatial patterns of ectopic FT gene expression. Soy physiological experiments identifying Gm.FT2a expression in vegetative tissues following the short day induction treatment (see FIG. 2) indicated that achieving yield positive traits may rely on earlier FT expression during the vegetative stage. On the other hand, even though FT transcripts are not detected in the vegetative apex, FT protein has been shown to move long distance from the leaves to the apical tissue where it triggers a vegetative to reproductive transition. See, e.g., Lifschitz, E. et al., (2006), supra; and Corbeiser, L. et al., "FT Protein Movement Contributes to Long-Distance Signaling in Floral Induction of *Arabidopsis*", *Science* 316: 1030-1033 (2007). Thus, in light of our own observations, we proposed using a vegetative stage promoter that is active in the meristem to control ectopic FT expression in a plant. By expressing the morphogenetic FT signal directly in the meristem at the desired developmental stage, multiple endogenous pathways and regulatory feedbacks (e.g., control of FT transduction in the leaf and long distance translocation of the FT signal) may be bypassed or avoided. Previous experiments with the short day induction treatment (described above in Example 1) revealed up-regulation of the Gm.Erecta gene in the meristems of soybean plants. The pErecta promoter (SEQ ID NO: 21) from *Arabidopsis* had been shown to have weak expression in the meristem(s) of plants during vegetative stages of development. Accordingly, the pAt.Erecta promoter was selected for initial FT expression experiments.

Figure 4A:
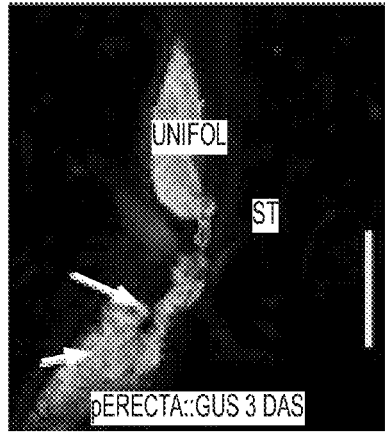
Figure 4B:
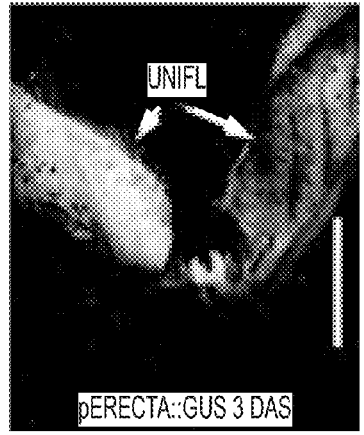
Figure 4C:
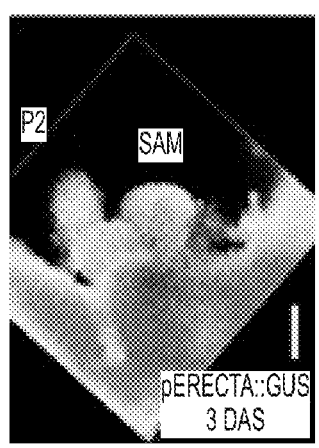
Figure 4D:
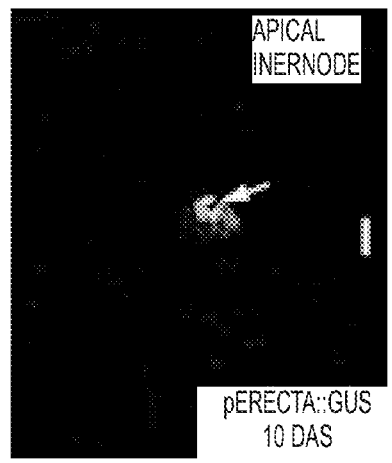
Figure 4E:
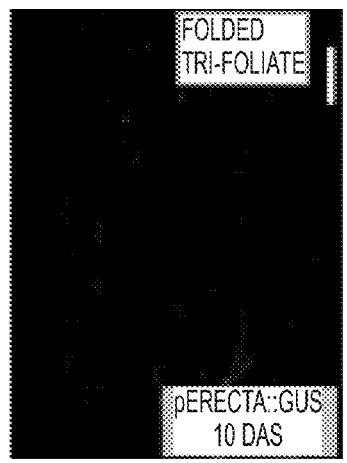
Figure 4F:
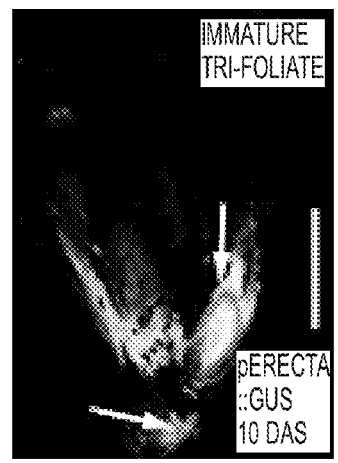
Figure 4G:
Figure 4H:
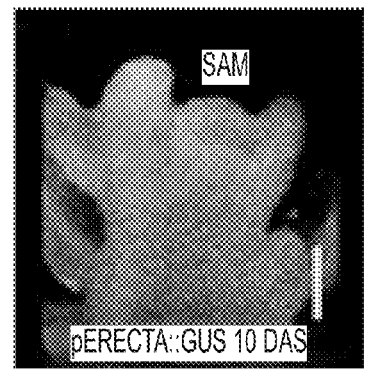
Figure 4I:
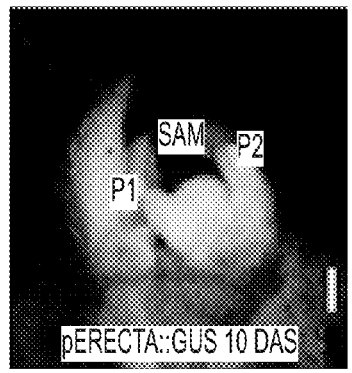

Additional experiments were performed to further characterize the expression patterns of pAt.Erecta fused to a GUS reporter gene in vegetative and floral meristematic tissues. Analysis of GUS expression patterns during the development of soy seedlings indicated that the pAt.Erecta promoter exhibits a temporal and spatial pattern of expression, preferably in the meristematic tissues during the vegetative stage of development. FIGS. 3A to 3O and 4A to 4O and FIGS. 5A to 5F and 6A to 6F include two sets of images to show the pattern of GUS staining. FIGS. 3A to 3O and 5A to 5F provide black and white images of the stained tissues, and FIGS. 4A to 4O and 6A to 6F provide black and white images corresponding to FIGS. 3A to 3O and 5A to 5F, respectively, but color filtered to show the pattern and intensity of blue GUS staining. Thus, the GUS staining pattern of expression can be viewed with these black and white images by comparing the corresponding images of FIGS. 3A to 3O and 4A to 4O or FIGS. 5A to 5F and 6A to 6F. As shown in FIGS. 3A to 3O and 4A to 4O, GUS staining was detected in the soy immature uni-foliate blade and petiole (FIGS. 4A and 4B) at three days after sowing/germination. pAt.Erecta:GUS expression was also broadly detected in the trifoliate primordia, shoot apical meristem (SAM) and axillary meristem sites at this early vegetative stage (FIG. 4C). GUS activity was not detected in the fully expanded uni-foliate and trifoliate leaves at ten days after germination or planting (FIGS. 4D and 4E). However, GUS activity was detected at the proximal part of the immature, unexpanded, but fully developed trifoliate blade, and at the adaxial side of the petiole (FIG. 4F). Detailed observation of the developing apical tissue showed that broad expression was retained in the developing immature leaf primordia, axillary meristems and shoot apical meristems (FIGS. 4G-I).

Figure 4J:
Figure 4K:
Figure 4L:
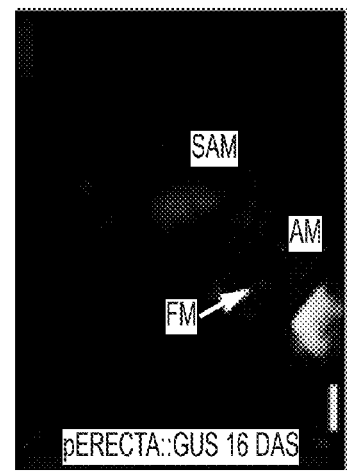
Figure 4M:
Figure 4N:
Figure 4O:
Figure 6A:
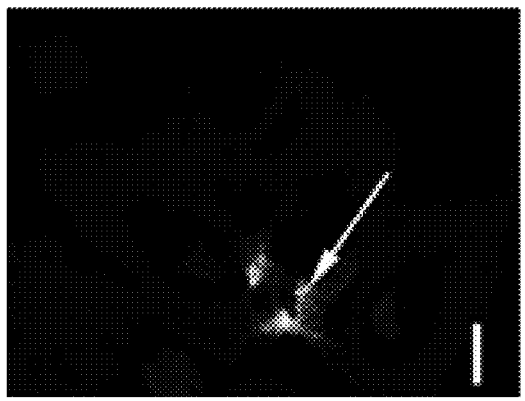
Figure 6B:
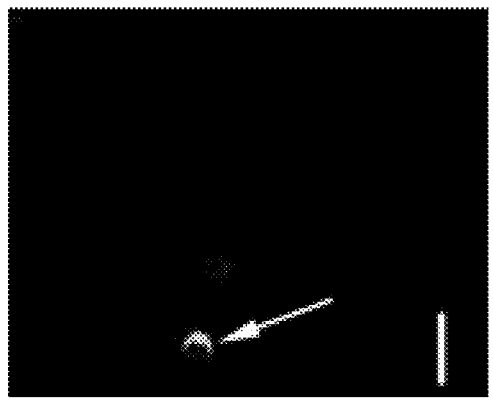
Figure 6C:
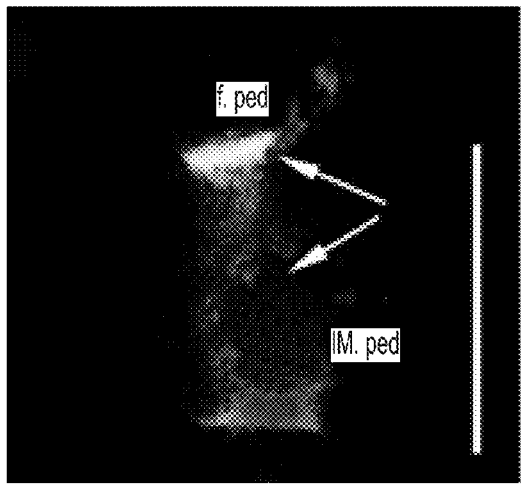
Figure 6D:
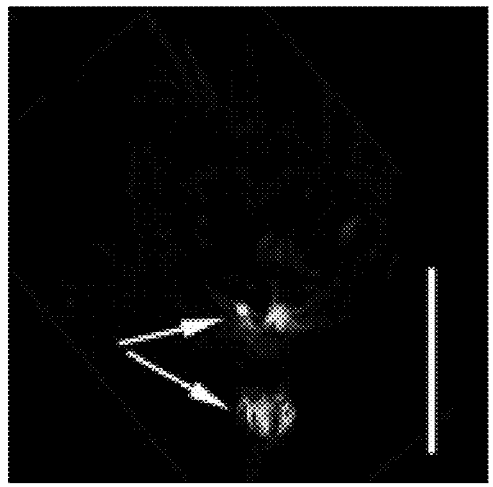
Figure 6E:
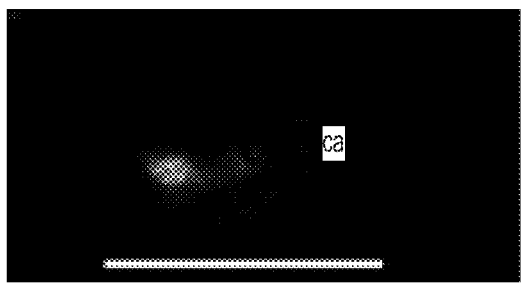
Figure 6F:
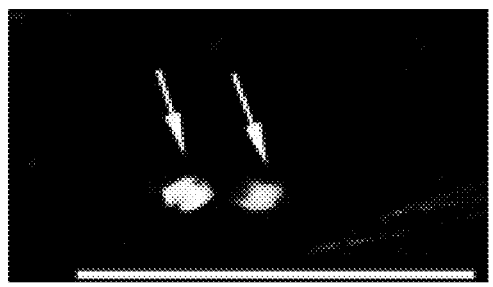

At the early reproductive stage, pAt.Erecta promoter activity was not detected in the mature blade and was reduced in the developing leaf primordia. The GUS signal was not detected in the indeterminate vegetative apex at the shoot apical meristem (SAM) or in the axillary meristem (AM) once these tissues started to form inflorescences (FIGS. 4J-4L). In all later stages, any additional meristematic activity could not be detected in the apex or in the axillaries or flower primordia. However, GUS expression continued in the adaxial side of the petiole and proximal part of the immature leaf blade (FIGS. 4M and 4N), but not in the fully expanded leaf blade (FIG. 4O). GUS expression patterns with the pAt.Erecta promoter were also analyzed at the later R1 stages of development (35-40 days after germination). Similar to earlier stages of development, no expression was detected in the mature leaves or stems. However, strong promoter activity was detected in the inflorescence stems (FIGS. 5A and 6A; see arrow) and floral pedicels (FIGS. 5B and 6B; see arrow). In both tissues, expression was detected in vasculature and parenchyma cells (FIGS. 5C and 6C). At this stage, expression was also detected in the stamen filaments (FIGS. 5D and 6D; see arrows) and in the un-pollinated ovules (FIGS. 5E, 5F, 6E and 6F; see arrows in 6F).

Previously, the pAt.Erecta promoter was characterized in *Arabidopsis*. Interestingly, pAt.Erecta expression patterns in *Arabidopsis* were comparable to the patterns observed in soy during the vegetative stage, but not during late reproductive stages. In contrast, the pAt.Erecta expression pattern in soybean is diminished in early reproductive tissues but remerges in some later reproductive organs and tissues, including the inflorescence stems and floral pedicels. See, e.g., Chen, M-K et al., *FEBS Letters* 588: 3912-17 (2014); Yokoyama, R et al.; Shpak, E D et al., *Science* 309: 290-293 (2005); and Yokoyama, R et al., *Plant J* 15(3): 301-310 (1998), the entire contents and disclosures of which are incorporated herein by reference. Thus, the pAt.Erecta promoter provides a novel expression pattern in soybean.

Example 3. Expression of Flowering Locus T Gene, Gm.FT2a, Under Control of a pAt.Erecta Promoter Alters Flowering Time and Pods Per Node in Soybean Transgenic soybean plants were produced by transforming soybean explants with a recombinant DNA molecule (i.e., a T-DNA transformation vector) comprising the pAt.Erecta promoter operably linked to the Gm.FT2a gene via *Agrobacterium*-mediated transformation to generate four pErecta::Gm.FT2a events that were carried forward for further testing. The effect of FT2a overexpression was immediately seen in $R_0$ plants, which had very early flowering and termination with reduced seed yield (e.g., only about 8 seeds/plant). These transgenic Gm.FT2a plants also had a short plant height and very few, if any, branches. Segregating R1 plants and their progeny were subsequently grown in the greenhouse under long day conditions for initial study and characterization. By growing these plants under long day conditions, the severe dwarf phenotypes observed with Gm.FT2a transgenic $R_0$ plants were improved. In these experiments, both homozygous and hemizygous plants grown in the greenhouse under 16-hour long day conditions (i.e., 16/8 hours of day/night photoperiods) flowered much earlier than wild type null segregants. Gm.FT2a transgenic plants flowered at about 19-22 days after planting or seeding). (see, e.g., FIGS. 9A to 9C). Under these growth conditions, transgenic soybean plants expressing Gm.FT2a further had an increased number of pods per node on the main stem in comparison to wild type controls (see, e.g., FIGS. 10 and 11, discussed further below).

Figure 7:
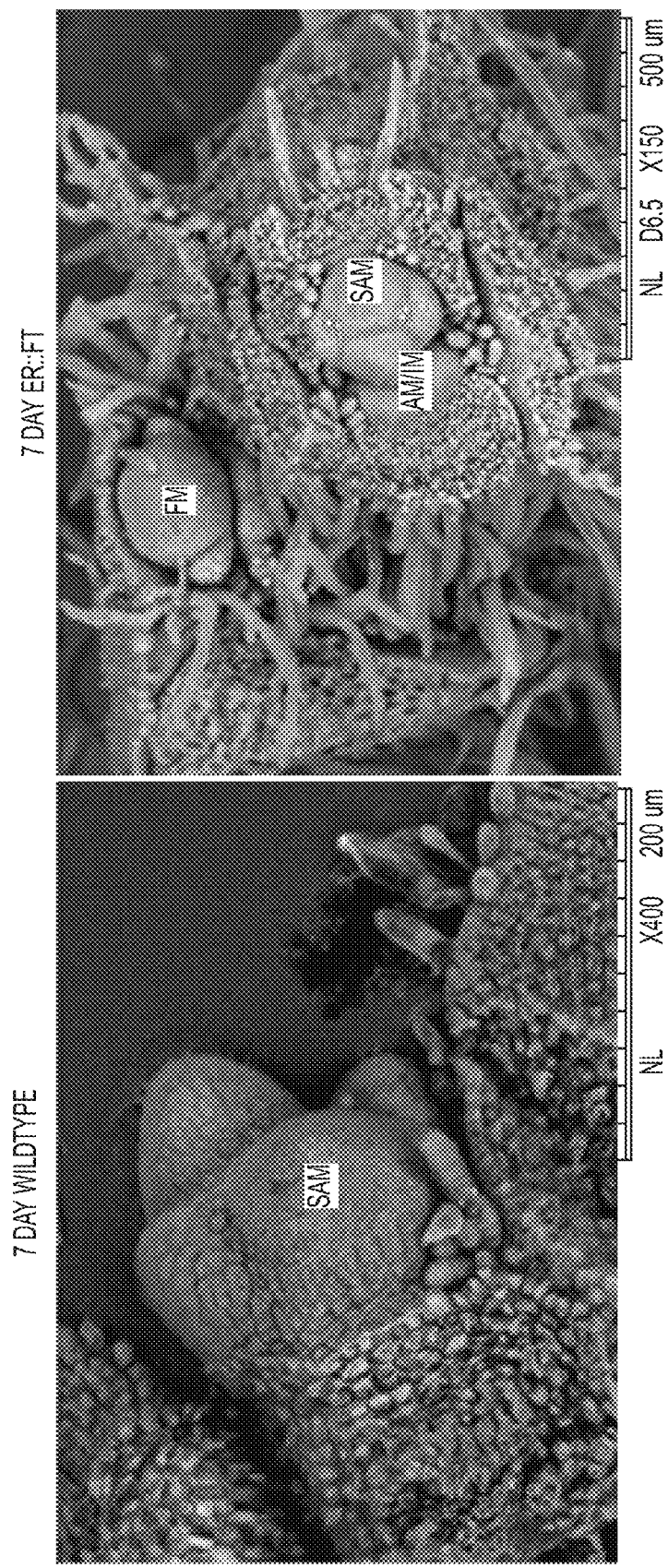
FIG. 7 shows section imaging of the shoot apical meristem (SAM) from wild type versus GmFT2a-expressing transgenic plants at 7 days after planting using scanning electron microscopy (eSEM) analysis.
Figure 8:
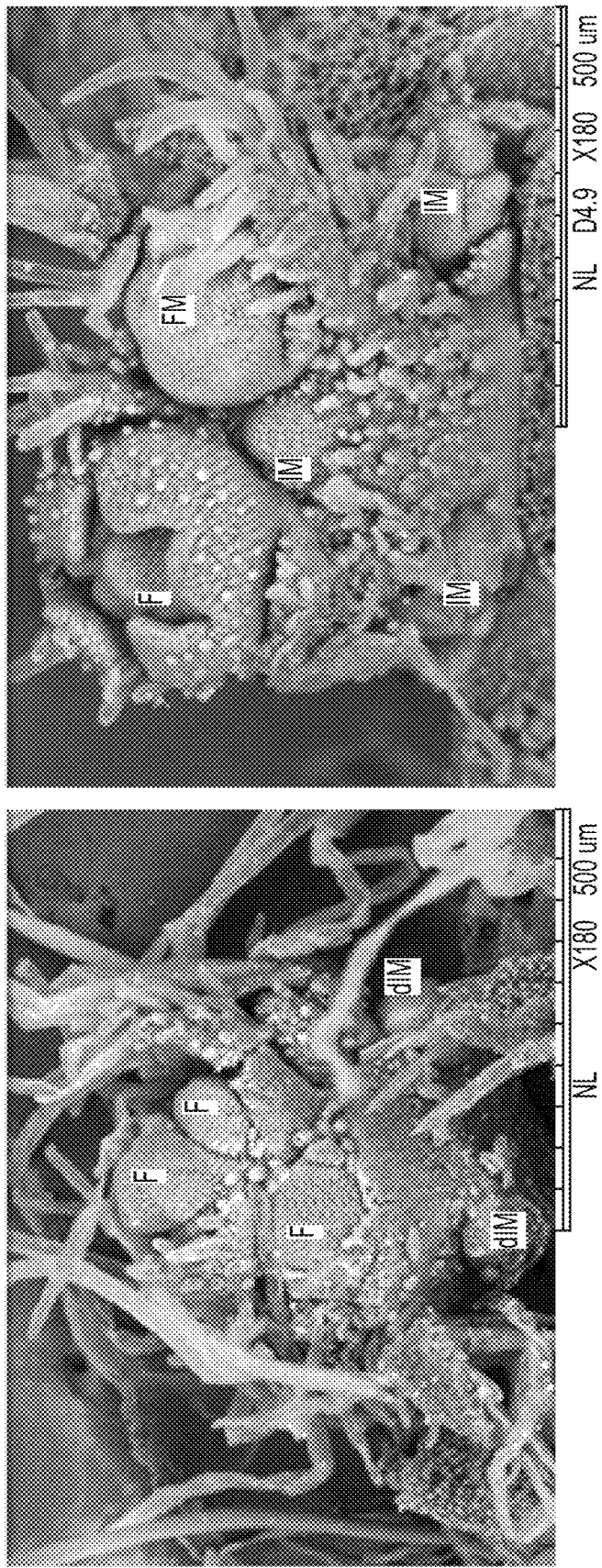
FIG. 8 shows scanning electron microscopy (eSEM) micrographs of an axillary inflorescence primordia from a wild type plant (collected at 27 days after planting), in comparison to an axillary inflorescence primordia from a transgenic event expressing Gm.FT2a (collected at 9 days after planting).
Figure 9C:
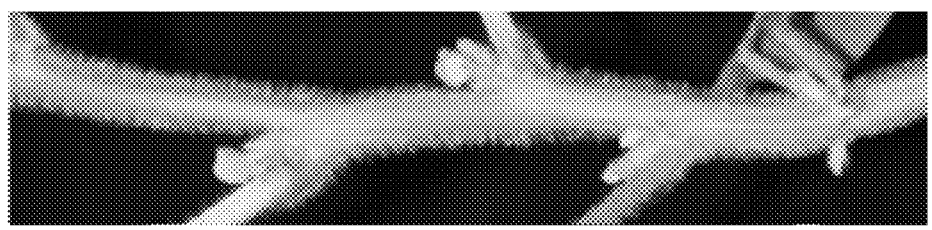
FIGS. 9A to 9C show the effects of Gm.FT2a expression driven by the At.Erecta promoter in soybean.
Figure 9B:
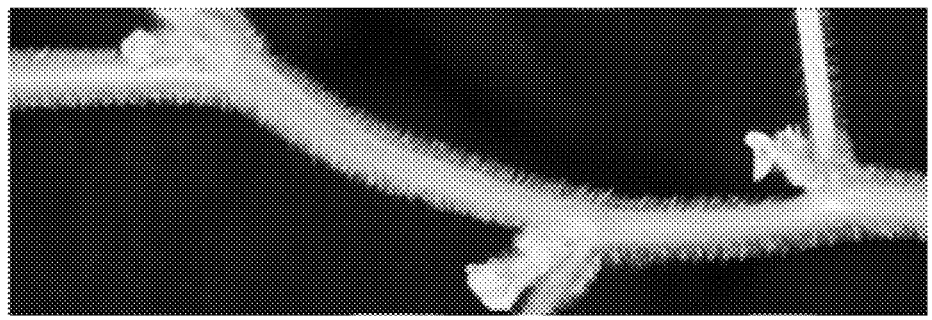
Figure 9A:
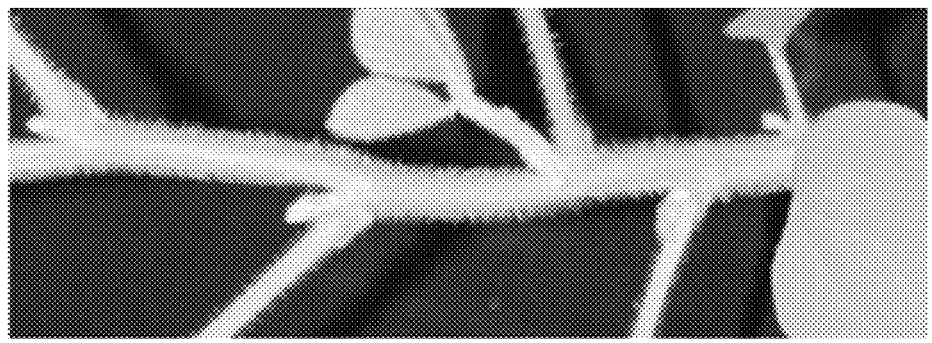

Plants containing one of the pEr::Gm.FT2a transgenic events (Event 1) grown in controlled environment conditions were further analyzed via scanning electron microscopy analysis (eSEM). Analysis of the shoot apical meristem (SAM) of these transgenic plants (collected at 7 days after planting) revealed an early transition of the SAM into an inflorescence meristem (IM) and floral meristem (FM) (FIG. 7). In contrast, the SAMs of wild type soybean plants were not differentiated into IM at this growth stage. Similarly, imaging of the axillary meristem of the FT2a transformants (collected at 9 days after planting) indicated the development of dormant inflorescence meristems (dIMs) (or lateral primordial racemes) into IM and FM (FIG. 8), leading to more earlier-developing floral branches (racemes) per node in these transgenic plants. Additional phenotypic characterization revealed early flowering at the V1 stage in Gm.FT2a expressing soybean plants, which was well before the floral transition occurred in null segregating plants (FIGS. 9A to 9C). These data in combination with the pAt.Erecta:GUS expression pattern described above indicate that early flowering, and more particularly the formation of inflorescence and floral meristems, were induced by ectopic expression of Gm.FT2a during the vegetative stage in leaf primordia and the shoot apical and axillary meristems of seedlings. The formation of a higher number of inflorescence and floral meristems is believed to further cause earlier release and elongation of the secondary and tertiary racemes, leading to a greater number of productive flowers and pods being formed per node.

Figure 10:
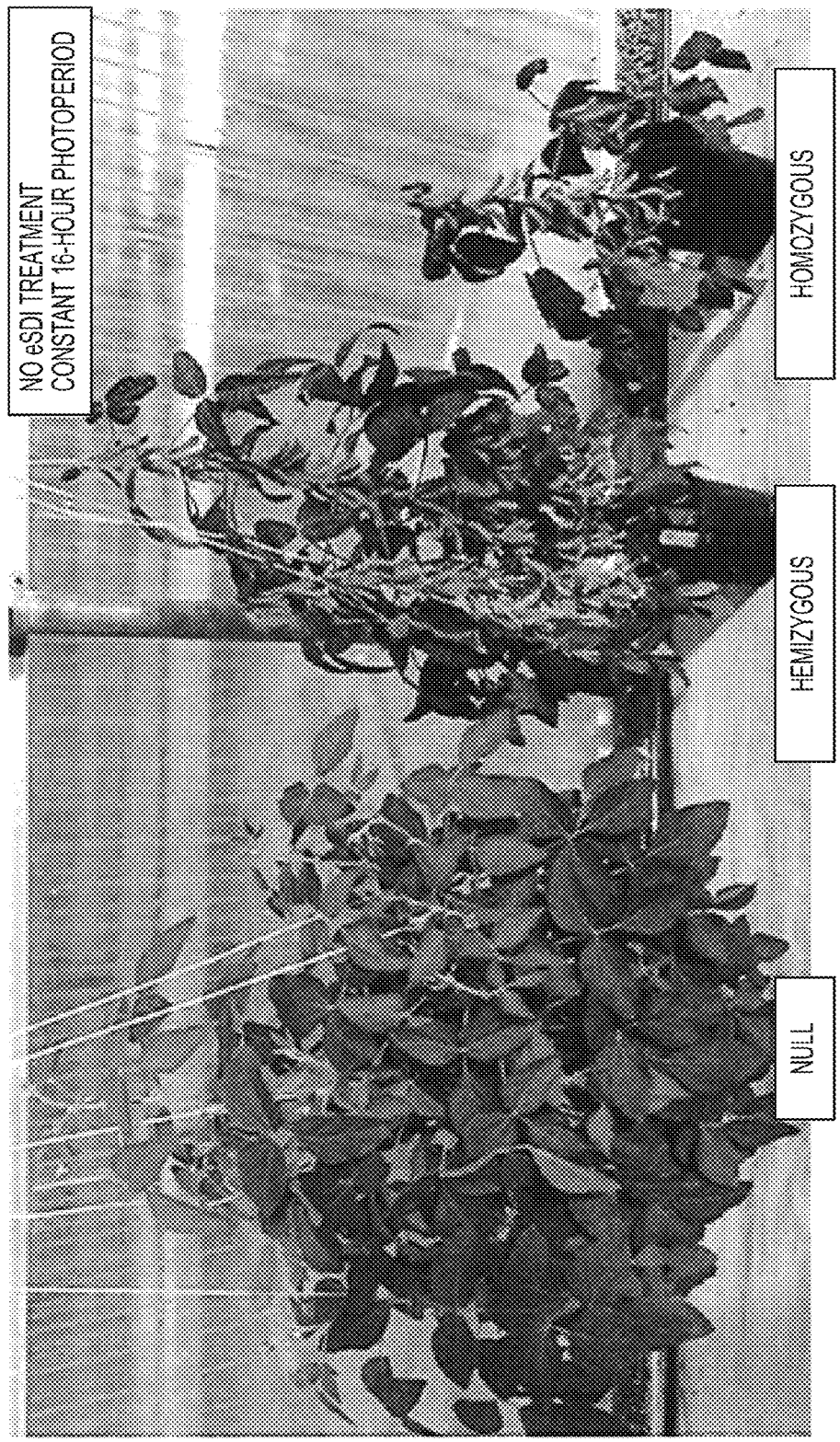
FIG. 10 shows a whole plant image of a wild type null segregant next to plants hemizygous and homozygous for the Gm.FT2a transgene as indicated.

Not only did Gm.FT2a transgenic soybean plants experience earlier flowering and produce more pods per node on the main stem (relative to segregating null plants), the effects of ectopic Gm.FT2a expression in transgenic plants were also found to be dosage dependent. Although both homozygous and hemizygous plants had a reduced height and less branching, plants homozygous for the Gm.FT2a transgene were more severely affected than hemizygous plants, presumably because homozygous plants contain two copies of the transgene (i.e., a higher dosage), as opposed to only one copy (i.e., a lower dosage) in hemizygous plants. Under long day growth conditions, homozygous plants terminated earlier and had a shorter overall height with fewer nodes and branches on the main stem in comparison to plants hemizygous for the transgene (FIG. 10). Unlike homozygous plants, which exhibited a number of sub-optimal dwarf phenotypes including very few (if any) branches on the main stem, hemizygous plants had an intermediate phenotype in terms of their vegetative growth, plant height, and the number of nodes present on the main stem relative to wild type and homozygous plants. Under 16-hour long day conditions, hemizygous plants had a more normal plant height with some degree of branching and a more extended duration of flowering, relative to homozygous plants (FIG. 10). Hemizygous plants also flowered for 40-64 days after initiation of R1, whereas homozygous plants flowered for only 16-24 days due to their earlier termination.

Additional experiments were conducted with plants transformed with the Gm.FT2a construct (3 events) in long day (16 hour) controlled environment conditions to further characterize the dosage response between hemizygous and homozygous plants. Differences in the number of nodes and pods on the main stem and branches, as well as the average number of pods per node and the average height per plant are shown in Table 1 for three homozygous events (Homo-Event 2, Homo-Event 3, Homo-Event 4) and three hemizygous events (Hemi-Event 2, Hemi-Event 3, Hemi-Event 4). These events are distinguished from Event 1 above.

on the main stem was also found to be different between FT2a transgenic and wild type null plants. Both homozygous and hemizygous plants grown under long day conditions were found to have more pods on at least the lower nodes of the main stem and more pods per node on average, in comparison to wild type null plants (data not shown). Plants hemizygous for the Gm.FT2a transgene contained the highest number of pods per node over the length of the main stem. However, these effects were dependent on the particular growing conditions including day length, etc. In general, experiments performed with soybean under longer day conditions tended to produce greater differences between transgenic and null plants.

The dosage-dependent effects of transgenic Gm.FT2a expression were also observed in field trial experiments. In a 2014 field trial, soybean plants hemizygous for two Gm.FT2a events (Events 1 and 2 above) showed an average of about 2.68 pods per node on the main stem, and plants homozygous for these events had about 1.40 pods per node on average, whereas null segregating plants had about 1.63 pods per node. In a 2013 field trial, however, plants hemizygous for transgenic Gm.FT2a (Event 2) were found to have an average number of about 3.21 pods per node, as compared to an average of about 3.05 pods per node in

TABLE 1

Event level data for homozygous and hemizygous Gm.FT2a transgenic plants.

| Zygosity-Event # | Avg. # MS nodes per plant | Avg. # BR nodes per plant | Avg. # MS pods per plant | Avg. # BR pods per plant | Avg. Pods per Node | Avg. Height (in) per plant |
|---|---|---|---|---|---|---|
| Homo-Event 2 | 11.8 | 6.9 | 46 | 9 | 2.9 | 17.5 |
| Homo-Event 3 | 12.3 | 6.5 | 66.4 | 9 | 4 | 21 |
| Homo-Event 4 | 12.5 | 6.8 | 49.6 | 9.1 | 3 | 19.5 |
| Hemi-Event 2 | 25.3 | 12.4 | 183.5 | 47.3 | 6.1 | 37.5 |
| Hemi-Event 3 | 23.9 | 13.2 | 200.3 | 28.8 | 6.1 | 40 |
| Hemi-Event 4 | 25.4 | 15.3 | 186.8 | 58 | 6 | 41.5 |

As shown in Table 1, hemizygous plants consistently had a higher number of nodes on the main stem (MS) and branches (BR) and a greater plant height than homozygous plants. Thus, hemizygous plants were generally less affected than homozygous plants and more like wild type plants. Hemizygous plants also had an increased number of pods per node and a higher number of pods on the main stem and branches, relative to homozygous plants. Therefore, hemizygous plants generally had a closer-to-normal plant architecture with a greater number of pods per node (and per plant), presumably due to their lower Gm.FT2a transgene dosage. The relative dosage level of Gm.FT2a based on transgene zygosity was further confirmed by additional experiments showing that Gm.FT2a transcript levels were higher in tissues from homozygous plants, than in tissues from hemizygous plants (data not shown).

The early induction of flowering in these Gm.FT2a transgenic plants was associated with more pods (and seeds) per node on the main stem in both hemizygous and homozygous plants. Homozygous and hemizygous plants containing the Gm.FT2a transgene each had an increased number of pods/seeds per node on the main stem of the plant in comparison to wild type segregants (FIG. 11). The distribution of pods homozygous plants and about 2.19 pods per node in null segregating plants. In another 2013 micro plot experiment conducted at a different field location, plants hemizygous for the Gm.FT2a transgene (Event 1) were found to have about 2.17 pods per node on average, as compared to an average of about 2.05 pods per node in plants homozygous for the Gm.FT2a transgene (Event 2) and about 1.30 pods per node in null segregating plants. Thus, the number of pods per node on plants containing the Gm.FT2a transgene may depend on a variety of factors including dosage of the FT transgene, environmental and field conditions, and perhaps differences in agronomic practices. However, much like transgenic Gm.FT2a plants grown in the greenhouse, homozygous and hemizygous Gm.FT2a transgenic plants grown under field conditions often had fewer nodes on the main stem, shorter overall plant height, and/or reduced branching in transgenic plants. Indeed, wild type plants typically had more branching and a greater number of total nodes per plant than hemizygous and homozygous Gm.FT2a plants.

Additional physiological data was collected from homozygous Gm.FT2a transgenic plants and wild type (WT) control plants grown in the greenhouse under 14-hour long day conditions (see Table 2). These data provide an average of measurements taken from six Gm.FT2a transgenic plants for each event, or from eight wild type plants. The following matrices were collected for phenotypic characterization of these plants: Days to flowering at R1 (DOFR1); Days to R7 (DOR7); reproductive duration in days from R1 to R7 (PDR1R7); number of branches per plant (BRPP); total fertile nodes on branches (FNBR); total fertile nodes per plant (FNLP); total fertile nodes on main stem (FNST); number of nodes on branches (NDBR); number of nodes on main stem (NDMS); number of nodes/plant (NDPL); percent fertile nodes on branches (PFNB); percent total fertile nodes (PFNN); percent fertile nodes on main stem (PFNS); number of pods per plant (PDPP); number of pods on main stem (PODMS); number of pods on branches (PODBR); number of pods/node; seeds per plant at R8 (SDPPR8); and weight of 1000 seeds (SW1000). Each of these measurements was taken at harvest unless another time point is specified.

TABLE 2

Construct level phenotypic data for transgenic homozygous Gm.FT2a and WT plants.

|  | WT | pErecta::Gm.FT2a |
|---|---|---|
| DOFR1 | 33.5 | 21.3 |
| DOR7 | 106.9 | 92.9 |
| PDR1R7 | 76.5 | 71.6 |
| BRPP | 20.1 | 1 |
| FNBR | 190.6 | 2 |
| FNLP | 214.6 | 15 |
| FNST | 24.0 | 14.3 |
| NDBR | 211.4 | 3 |
| NDMS | 33.4 | 15.3 |
| NDPL | 244.9 | 16.3 |
| PDPP | 575.8 | 61.2 |
| PFNB | 90.4 | 75 |
| PFNN | 87.8 | 92.0 |
| PFNS | 71.4 | 92.9 |
| PODBR | 487.3 | 3 |
| PODMS | 88.4 | 60.2 |
| Pods/Node | 2.4 | 3.8 |
| SDPPR8 | 1319.6 | 122.1 |
| SW1000 (grams) | 146 | 122.5 |

Consistent with the observations noted above, homozygous Gm.FT2a transgenic plants experienced earlier floral induction than WT plants (DOFR1 about 21 days after planting, instead of about 33-34 days in wild type plants). These measurements further showed that the number of branches (and other measurements related to branching, such as the number of nodes or pods on branches) was greatly reduced. Due to the transgenic plants having a shorter stature with very little branching, the total numbers of nodes or pods per plant were also greatly reduced. However, the number of pods per node on the main stem was increased in transgenic plants (e.g., about 3.8 average pods/node) relative to wild type null plants (e.g., about 2.4 pods/node).

Without being bound by any theory, the larger number of pods per node observed with transgenic soybean plants expressing FT2a in the meristem during vegetative stages of development may be caused at least in part by synchronization of early flowering with early secondary and/or tertiary raceme release and/or better resource utilization to produce more pod-producing flowers per node. Early FT expression in the meristem (see, e.g., FIGS. 3 and 4) may cause early release of the dormant inflorescence meristems to produce a greater number of racemes per node of the plant, such that a greater number of racemes produce mature flowers and fully developed pods at each node. However, subsequent FT expression in reproductive tissues (see, e.g., FIGS. 5 and 6) may terminate floral development of later developing flowers at each node leading to more efficient resource allocation to the earlier developing racemes, flowers and pods. In wild-type soybean plants, a much lower percentage of secondary and tertiary racemes produce flowers and fully developed pods relative to primary racemes, and later developing flowers of the primary raceme typically do not produce mature flowers and/or full-sized pods prior to abscission. Thus, it is theorized that more pods per node may be generated in plants expressing FT proteins in the vegetative meristem by synchronizing early flower development with early release of the lateral racemes at one or more node(s) of the plant. With at least the pAt.Erecta promoter driving FT expression, later developing flowers (that may not otherwise produce fully developed or full-sized pods) may also become terminated by later reproductive-stage expression of FT to direct resources to the earlier developing flowers.

Example 4. Expression of Flowering Locus T Gene, Gm.FT2a, Under Control of Alternative Vegetative Stage Promoters in Soybean Based on the phenotypes observed in the preceding Example 3, two promoters were also proposed to drive Gm.FT2a transgene expression that were considered vegetative-stage, leaf-preferred promoters: pAt.BLS (SEQ ID NO: 36) and pAt.ALMT6 (SEQ ID NO: 37). As used herein, a "leaf-preferred" promoter refers to a promoter that preferentially initiates transcription of its associated gene in leaf tissues relative to other plant tissues. Since FT is believed to function as a mobile florigen, early FT expression during vegetative stages in peripheral tissues, such as in the leaf with a leaf-preferred or leaf-specific promoter, may lead to phenotypes similar to the meristem-preferred pAt.Erecta:Gm.FT2a expression. It was further theorized that FT expression with a vegetative leaf promoter might also attenuate the floral induction signal, and thus mitigate the early termination phenotypes observed with homozygous FT expression in the meristem, and increase plant height and branching.

In these experiments, transformation vectors for pAt.ALMT6::Gm.FT2a and pAt.BLS::Gm.FT2a were constructed and used to transform a soybean line by *Agrobacterium*-mediated transformation. Expression with the pAt.BLS promoter has been shown to start in leaf primordia number 5 (p5) and is expressed in the source leaf veins only until transition to flowering, and the pAt.ALMT6 promoter is also a vegetative leaf promoter with expression at later developmental stages relative to pAt.BLS. See, e.g., Efroni et al., "A Protracted and Dynamic Maturation Schedule Underlies *Arabidopsis* Leaf Development," The Plant Cell 20(9): 2293-2306 (2008); and Shani et al., "Stage-Specific Regulation of *Solanum lycopersicum* Leaf Maturation by Class 1 KNOTTED1-LIKE HOMEOBOX Proteins," The Plant Cell 21(10): 3078-3092 (2009). Transgenic soybean plants were produced for each of these vector constructs and characterized for phenotypes in growth chambers under 14-hour photoperiod conditions in comparison to wild type plants. For each of the pAt.BLS construct, six transgenic events were tested (5 plants per event), and for the pAt.ALMT6 promoter, seven transgenic events were tested (5 plants per event). For each of these constructs, control data was collected from five wild type plants.

The following matrices were collected for phenotypic characterization of these transgenic plants (Tables 3 and 4). The individual measurements are as defined above, and phenotypic characterization was conducted on plants homozygous for the transgene.

TABLE 3

Construct level phenotypic data for pALMT6::Gm.FT2a and WT plants.

|  | WT | pALMT6::FT2a |
|---|---|---|
| DOFR1 | 35.2 | 38.8 |
| DOR7 | 84.7 | 88.8 |
| PDR1R7 | 49.5 | 50.0 |
| BRPP | 7.7 | 8.9 |
| FNBR | 57.8 | 73.3 |
| FNLP | 69.7 | 85.0 |
| FNST | 12.0 | 11.7 |
| NDBR | 78.9 | 96.0 |
| NDMS | 21.3 | 22.5 |
| NDPL | 100.2 | 118.5 |
| PDPP | 120.2 | 141.1 |
| PFNB | 73.2 | 76.8 |
| PFNN | 71.7 | 72.1 |
| PFNS | 57.9 | 51.7 |
| PODBR | 91.8 | 118.1 |
| PODMS | 28.3 | 22.9 |
| Pods/Node | 1.4 | 1.2 |

TABLE 4

Construct level phenotypic data for pBTS::Gm.FT2a and WT plants.

|  | WT | pBLS::FT2a |
|---|---|---|
| DOFR1 | 31.3 | 35.2 |
| DOR7 | 78.1 | 82.6 |
| PDR1R7 | 46.9 | 47.5 |
| BRPP | 7.5 | 8.8 |
| FNBR | 65.7 | 81.2 |
| FNLP | 80.5 | 94.0 |
| FNST | 14.9 | 12.7 |
| NDBR | 72.2 | 95.6 |
| NDMS | 21.9 | 22.3 |
| NDPL | 94.0 | 117.9 |
| PDPP | 137.0 | 148.1 |
| PFNB | 92.3 | 85.3 |
| PFNN | 87.4 | 80.1 |
| PFNS | 68.1 | 57.3 |
| PODBR | 100.9 | 123.4 |
| PODMS | 36.1 | 24.8 |
| Pods/Node | 1.7 | 1.3 |

Transgenic plants expressing Gm.FT2a under the control of the alternative pAt.ALMT6 and pAt.BLS promoters were phenotypically more similar to wild type (WT) plants than pAT.Erecta::Gm.FT2a transgenic plants. Plants transformed with the pAt.ALMT6::Gm.FT2a and pAt.BLS::Gm.FT2a constructs had flowering times and vegetative growth traits similar to wild type control plants, perhaps with a slightly increased number of nodes on branches as compared to wild type plants (Tables 3 and 4). These data may be interpreted to indicate that both the timing and location of transgenic FT expression are important for producing reproductive and yield-related traits or phenotypes that differ from wild-type plants. Merely expressing a FT transgene during earlier vegetative stages of development (e.g., in leaf tissues) may not be sufficient to alter the reproductive or yield-related phenotypes of a plant (e.g., pods per node). Thus, according to embodiments of the present invention, a promoter operably linked to a florigenic FT transgene may preferably be a meristem-specific or meristem-preferred promoter in addition to driving expression during the vegetative stages of plant development. However, when the expression profiles for the above two leaf-preferred promoters were tested in soybean plants, no GUS staining was observed in the developing leaf with the pAt.BLS promoter, and the pAt.ALMT6 promoter did not produce detectable GUS expression in the leaf until late vegetative stages with much higher expression during early reproductive stages. Thus, it remains possible that expression of FT transgenes in peripheral (leaf) tissues during early vegetative stages using different tissue-specific promoters may be sufficient in some cases to induce early flowering and/or cause other reproductive or yield-related traits or phenotypes, which may also depend on the particular plant species tested.

Example 5. Identification of Protein Domains of FT Homologs by Pfam Analysis

Gm.FT2a orthologs were identified by sequence analysis and literature review, and a few examples of these FT homologs are listed in Table 5 along with Gm.FT2a. These included other soybean FT genes as well as a few FT genes from other plant species. The amino acid sequences of these FT proteins were analyzed to identify any Pfam protein domains using the HMMER software and Pfam databases (version 27.0). These FT protein sequences (SEQ ID NOs: 2, 4, 6, 8, 10 and 12) were found to have the same Pfam domain identified as a phosphatidyl ethanolamine binding domain protein (PEBP) having a Pfam domain name of "PBP_N", and a Pfam accession number of PF01161. The location of the PBP_N domains in each of these FT protein sequences are also listed in Table 5. The location of the PBP_N domain in other FT proteins can be determined by sequence alignment. It is thus contemplated that any DNA sequence encoding at least an FT protein comprising the PBP_N domain may be used in a recombinant DNA molecule of the present invention, as long as the corresponding FT protein has florigenic activity when ectopically expressed in the meristem of a plant.

TABLE 5

Location of PBP_N (Pfam) domain in FT protein sequences.

| PROTEIN SEQ ID NO. | Gene Name | Domain location |
|---|---|---|
| 2 | Gm.FT2a | 28-162 |
| 4 | Gm.FT5a | 26-157 |
| 6 | Gm.FT2b | 28-162 |
| 8 | Zm.ZCN8 | 26-154 |
| 10 | Nt.FT-like | 25-159 |
| 12 | Le.SFT | 29-161 |

Example 6. Expression of FT Homologs Under Control of pAt.Erecta Promoter in Soybean Additional transformation vectors containing other FT homologs (Table 6) under control of the pAt.Erecta promoter were constructed and used to transform soybeans via *Agrobacterium*-mediated transformation. Transgenic plants generated from these events were characterized for their phenotypes in the greenhouse with a 14 to 14.5 hour natural daylight photoperiod. For each construct, six events were tested (6 plants per event). Six plants were also tested and averaged for wild type (WT) control plants. Different groups of experiments (A-E) were conducted as shown in Table 6 with separate wild type controls.

TABLE 6

List of constructs for some Gm.FT2a and its homologs with their protein sequences.

| Construct Description | Gene Name | PROTEIN SEQ ID NO. | Testing Group |
|---|---|---|---|
| pErecta: Gm.FT2a | Gm.FT2a | 2 | A |
| pErecta: Gm.FT2b | Gm.FT2b | 6 | C |
| pErecta: Gm.FT5a | Gm.FT5a | 4 | E |
| pErecta: Zm.ZCN8 | Zm.ZCN8 | 8 | B |
| pErecta: Nt.FT-like | Nt.FT-like | 10 | B |
| pErecta: Le.SFT | Le.SFT | 12 | D |

The following matrices were collected for phenotypic characterization of plants transformed with each of the constructs listed in Table 6 for expressing other FT homologs with the pAt.Erecta promoter, in addition to data collected for the Gm.FT2a construct as described above. The individual measurements are as defined above, and phenotypic characterization of transformants was conducted on plants homozygous for the transgene.

Phenotypic data was collected for plants expressing the Zm.ZCN8 and Nt.FT-like transgenes under the control of the pAt.Erecta promoter (see Tables 7 and 8). Trait values for each Event in Tables 7 and 8 are an average of all plants tested containing the Event. A column is also provided with an average of the Event values for each trait.

TABLE 7

Construct and event level phenotypic data for Zm.ZCN8 and WT plants.

|  | WT | Average | Event 1 | Event 2 | Event 3 | Event 4 | Event 5 | Event 6 |
|---|---|---|---|---|---|---|---|---|
| DOFR1 | 33.5 | 28.6 | 29 | 29.2 | 27.5 | 27 | 30.7 | 28 |
| DOR7 | 106.9 | 93.5 | 97.3 | 89.2 | 88.2 | 93.5 | 100.3 | 92.8 |
| PDR1R7 | 76.5 | 64.1 | 69.8 | 60 | 59 | 59.5 | 71.7 | 64.8 |
| BRPP | 20.1 | 3.2 | 2.8 | 1.3 | 1.5 | 1.3 | 9.5 | 3 |
| FNBR | 190.6 | 26.9 | 32 | 8 | 7 | 2.3 | 95.3 | 17 |
| FNLP | 214.6 | 54.9 | 67.5 | 28 | 40.5 | 20.3 | 132.5 | 40.5 |
| FNST | 24.0 | 28.3 | 35.5 | 22 | 33.5 | 18 | 37.3 | 23.5 |
| NDBR | 211.4 | 30.2 | 32.5 | 9 | 7.5 | 3.5 | 110.8 | 17.8 |
| NDMS | 33.4 | 30.5 | 36.3 | 24 | 34.3 | 20 | 44.8 | 24 |
| NDPL | 244.9 | 60.3 | 68.8 | 30.8 | 41.8 | 23.5 | 155.5 | 41.8 |
| PDPP | 575.8 | 317.5 | 498.3 | 144.8 | 319 | 76.3 | 658 | 208.8 |
| PFNB | 90.4 | 87.2 | 98.6 | 90.3 | 85.4 | 64.6 | 91.1 | 93.2 |
| PFNN | 87.8 | 93.1 | 98.1 | 92.3 | 97.0 | 86.5 | 88.5 | 96.4 |
| PFNS | 71.4 | 93.2 | 97.9 | 92.5 | 97.9 | 90.6 | 82.1 | 98.1 |
| PODBR | 487.3 | 105.4 | 162 | 19 | 18.5 | 3.3 | 384.5 | 45.3 |
| PODMS | 88.4 | 212.9 | 336.3 | 130.5 | 300.5 | 73 | 273.5 | 163.5 |
| Pods/Node | 2.4 | 5.5 | 7.2 | 4.6 | 7.7 | 3.2 | 4.9 | 5.2 |
| SDPP8 | 1319.6 | 564.7 | 961 | 200.5 | 562 | 136.8 | 1166.3 | 361.5 |
| SW1000 (grams) | 146 | 108.9 | 102.9 | 127.4 | 105.3 | 82.9 | 116.6 | 117.9 |

TABLE 8

Construct and event level phenotypic data for Nt.FT-like and WT plants.

|  | WT | Average | Event 1 | Event 2 | Event 3 | Event 4 | Event 5 | Event 6 |
|---|---|---|---|---|---|---|---|---|
| DOFR1 | 33.5 | 31.5 | 39.3 | 27.7 | 25.3 | 29 | 37.2 | 30.7 |
| DOR7 | 106.9 | 93.9 | 115.8 | 90.7 | 80.7 | 83.7 | 102.2 | 90.2 |
| PDR1R7 | 76.5 | 62.3 | 76.4 | 63 | 55.3 | 54.7 | 65 | 59.5 |
| BRPP | 20.1 | 9.8 | 20 | 8.3 | 2.3 | 5.3 | 17 | 6 |
| FNBR | 190.6 | 108.7 | 190.5 | 95.3 | 11 | 54.3 | 223 | 78.3 |
| FNLP | 214.6 | 131.4 | 212.3 | 118 | 29.5 | 77.8 | 248 | 103 |
| FNST | 24.0 | 23.2 | 21.8 | 22.8 | 21.3 | 23.5 | 25 | 24.8 |
| NDBR | 211.4 | 128.7 | 281.8 | 97 | 11 | 54.5 | 247.7 | 80.5 |
| NDMS | 33.4 | 28.9 | 33.8 | 27 | 23.3 | 24.8 | 35.7 | 28.8 |
| NDPL | 244.9 | 157.1 | 315.5 | 124 | 31.5 | 79.3 | 283.3 | 109.3 |
| PDPP | 575.8 | 462.1 | 638 | 511.3 | 150.8 | 296 | 745 | 431.5 |
| PFNB | 90.4 | 92.5 | 68.0 | 98.6 | 100 | 99.7 | 91.3 | 97.2 |
| PFNN | 87.8 | 89.6 | 67.6 | 95.4 | 93.3 | 98.3 | 88.4 | 94.2 |
| PFNS | 71.4 | 81.9 | 64.7 | 83.3 | 91.3 | 95.2 | 70.6 | 86.2 |
| PODBR | 487.3 | 326.3 | 529 | 342.3 | 22.7 | 147 | 633.3 | 283.5 |
| PODMS | 88.4 | 136.7 | 109 | 169 | 133.8 | 149 | 111.7 | 148 |
| Pods/Node | 2.4 | 3.6 | 2.0 | 4.3 | 4.9 | 3.8 | 2.7 | 4.0 |
| SDPPR8 | 1319.6 | 928.7 | 1359.8 | 965.5 | 382.7 | 591.5 | 1714.3 | 558.7 |
| SW1000 (grams) | 146 | 149.0 | 143.7 | 121.2 | 133.8 | 179.3 | 142.2 | 174.0 |

Transgenic soybean plants expressing the Zm.ZCN8 and Nt.FT-like proteins flowered earlier than wild type control plants and had an increased number of pods per node (similar to plants expressing the Gm.FT2a transgene). Indeed, soybean plants expressing the Zm.ZCN8 and Nt.FT-like transgenes had several phenotypes similar to the Gm.FT2a transgenic plants, including reduced number of days to flowering (DOFR1), reduced number of branches (BRPP), fewer nodes per plant (NDPL), fewer nodes on branches (NDBR), reduced number of pods per plant (PDPP), and fewer pods on branches (PODBR), along with an increase in the number of pods per node and a decrease in the number of seeds per plant (Tables 7 and 8), relative to wild type controls. However, several of the negative phenotypes observed in homozygous Gm.FT2a plants were less pronounced in the Zm.ZCN8 and Nt.FT-like expressing transgenic plants. Overall, plants expressing the Zm.ZCN8 transgene had shorter plant height and less branching but more pods per node on the main stem (FIGS. 12A and 12B). Similarly, plants expressing the Nt.FT-like transgene had shorter plant height, reduced branching and increased pods per node on the main stem (FIGS. 13A and 13B), relative to wild type control plants.

Two transgenic Zm.ZCN8 events and four Nt.FT-like events from above were also tested in 2015 field trials at two different locations. Phenotypic data was collected for plants expressing Zm.ZCN8 and Nt.FT-like transgenes under the control of the pAt.Erecta promoter (Tables 9 and 10). Events 1 and 2 in Table 9 correspond to Events 2 and 3 in Table 7, and Events 1-4 in Table 10 correspond to Events 1-4 in Table 8, respectively. Except for days to flowering at R1 (DOFR1) and reproductive duration in days from R1 to R8 (PDR1R8), all phenotypic measurements were derived based on data collected from two locations. Similar to the observations in the greenhouse, transgenic soybean plants expressing Zm.ZCN8 and Nt.FT-like proteins also flowered earlier than wild-type control plants in the field. The Zm.ZCN8 transgenic plants had an increased number of pods per node, while the Nt.FT-like plants did not clearly show increased pods per node in the field trial.

TABLE 9

Phenotypic data from 2015 field trial for Zm.ZCN8 and WT plants.

|  | WT | Average | Event 1 | Event 2 |
|---|---|---|---|---|
| DOFR1* | 42.4 | 27.9 | 28.0 | 27.7 |
| DOR8 | 110.7 | 95.0 | 92.0 | 98.0 |
| PDR1R8* | 65.7 | 67.1 | 63.5 | 70.7 |
| BRPP | 2.6 | 0.1 | 0.2 | 0.0 |
| NDBR | 9.7 | 0.3 | 0.5 | 0.1 |
| NDMS | 18.3 | 13.6 | 12.5 | 14.7 |
| NDPL | 28.0 | 13.9 | 13.0 | 14.8 |
| PDPP | 44.2 | 35.1 | 30.1 | 40.0 |
| TPBR | 9.5 | 0.3 | 0.5 | 0.1 |
| PODMS | 34.7 | 34.7 | 29.5 | 39.9 |
| Pods/Node | 1.6 | 2.5 | 2.3 | 2.6 |
| SDPPR8 | 99.9 | 67.6 | 54.7 | 80.5 |
| SW1000 (ounces) | 5.1 | 4.1 | 3.8 | 4.3 |

(*—single location data)

TABLE 10

Phenotypic data from 2015 field trial for Nt.FT-like and WT plants.

|  | WT | Average | Event 1 | Event 2 | Event 3 | Event 4 |
|---|---|---|---|---|---|---|
| DOFR1* | 42.4 | 38.0 | 42.5 | 26.8 | 26.8 | 25.8 |
| DOR8 | 110.7 | 93.3 | 111.3 | 88.2 | 86.6 | 87.1 |
| PDR1R8* | 65.7 | 63.1 | 66.8 | 62.2 | 60.3 | 63.0 |
| BRPP | 2.6 | 0.7 | 2.4 | 0.1 | 0.2 | 0.1 |
| NDBR | 9.7 | 2.7 | 9.2 | 0.5 | 0.8 | 0.3 |
| NDMS | 18.3 | 11.5 | 18.3 | 9.9 | 7.6 | 10.1 |
| NDPL | 28.0 | 14.2 | 27.5 | 10.4 | 8.5 | 10.4 |
| PDPP | 44.2 | 23.5 | 43.0 | 18.9 | 11.6 | 20.3 |
| TPBR | 9.5 | 2.6 | 8.4 | 0.5 | 0.8 | 0.5 |
| PODMS | 34.7 | 20.9 | 34.6 | 18.5 | 10.8 | 19.8 |
| Pods/Node | 1.6 | 1.6 | 1.6 | 1.8 | 1.4 | 1.7 |
| SDPPR8 | 99.9 | 49.9 | 98.6 | 36.3 | 25.0 | 39.7 |
| SW1000 (ounces) | 5.1 | 4.5 | 5.1 | 4.4 | 4.6 | 4.0 |

(*single location data)

Additional phenotypic data was collected for plants expressing the Gm.FT2b transgene under the control of the pAt.Erecta promoter (Table 11).

TABLE 11

Construct and event level phenotypic data for Gm.FT2b and WT plants.

|  | WT | Average | Event 1 | Event 2 | Event 3 | Event 4 | Event 5 | Event 6 |
|---|---|---|---|---|---|---|---|---|
| DOFR1 | 43.7 | 34.6 | 41.2 | 34.3 | 22.7 | 33.2 | 37.2 | 39.3 |
| DOR7 | 105.9 | 100.4 | 100.5 | 100.3 | 99.8 | 100.3 | 98.7 | 102.8 |
| PDR1R7 | 62.2 | 65.8 | 59.3 | 66 | 77.2 | 67.2 | 61.5 | 63.5 |
| BRPP | 13.4 | 4.7 | 7 | 5 | 1.7 | 3.3 | 3.7 | 7.7 |
| FNBR | 103.8 | 32.4 | 52 | 29.7 | 12 | 30.7 | 21.7 | 48.7 |
| FNLP | 125.0 | 46.6 | 68.7 | 41.3 | 24.3 | 45 | 37.3 | 63 |
| FNST | 21.2 | 14.2 | 16.7 | 11.7 | 12.3 | 14.3 | 15.7 | 14.3 |
| NDBR | 108.4 | 34.2 | 54 | 30.3 | 12.7 | 33.7 | 24.7 | 50 |
| NDMS | 30.2 | 18.0 | 18.3 | 15.3 | 15 | 19 | 19.3 | 21 |
| NDPL | 138.7 | 52.2 | 72.3 | 45.7 | 27.7 | 52.7 | 44 | 71 |
| PDPP | 387.4 | 143.0 | 167 | 140 | 96 | 145.7 | 108.7 | 200.7 |
| PFNB | 95.5 | 94.6 | 96.4 | 97.7 | 96.8 | 91.0 | 87.7 | 97.7 |
| PFNN | 90.1 | 89.1 | 94.9 | 90.3 | 88.0 | 86.0 | 86.1 | 89.4 |
| PFNS | 69.7 | 79.2 | 91.5 | 74.5 | 82.5 | 77.0 | 81.1 | 68.7 |
| PODBR | 284.9 | 90.2 | 109.3 | 96 | 43 | 94.7 | 55.3 | 143 |
| PODMS | 102.5 | 52.7 | 57.7 | 44 | 53 | 51 | 53.3 | 57.7 |
| Pods/Node | 2.8 | 2.7 | 2.3 | 3.1 | 3.5 | 2.8 | 2.5 | 2.8 |
| SDPPR8 | 1159.3 | 322.3 | 411.3 | 292.3 | 195.3 | 346.7 | 245 | 443.3 |
| SW1000 (grams) | 174.0 | 154.0 | 170.4 | 156.7 | 154.1 | 155 | 130.2 | 157.8 |

Figure 14:
FIG. 14 shows whole plant images of a wild type null segregant and a plant homozygous for the pEr:Gm.FT2b transgene as indicated.

Transgenic soybean plants expressing the Gm.FT2b transgene flowered earlier and had less branching than wild type control plants. Gm.FT2b expressing soybean plants had a reduced number of days to flowering (DOFR1), reduced number of branches (BRPP), fewer nodes per plant (NDPL), fewer nodes on branches (NDBR), reduced number of pods per plant (PDPP), and fewer pods on branches (PODBR) (Table 9). However, transgenic Gm.FT2b plants did not show an increase in the number of pods per node. Overall, plants expressing the Gm.FT2b transgene had shorter plant height and less branching relative to wild type control plants (FIG. 14). Transgenic soybean plants expressing four different events of the Gm.FT2b transgene were also tested in 2015 field trials. Phenotypic data was collected for plants expressing the Gm.FT2b transgene under the control of the pAt.Erecta promoter (Table 12). Events 1-4 in Table 11 correspond to Events 3, 2, 1, and 4 in Table 12, respectively. Similar to the observations in the greenhouse, Gm.FT2b expressing soybean plants showed a reduced number of days to flowering (DOFR1) in the field. The other phenotypic measurements also exhibited similar traits as observed in the greenhouse relative to wild-type control plants.

TABLE 12

Phenotypic data from 2015 field trial for Gm.FT2b and WT plants.

|  | WT | Average | Event 1 | Event 2 | Event 3 | Event 4 |
|---|---|---|---|---|---|---|
| DOFR1 | 41.9 | 37.3 | 38.3 | 38.3 | 36.3 | 36.2 |
| DOR8 | 115.4 | 109.2 | 111.1 | 110.6 | 110.6 | 104.6 |
| PDR1R8 | 73.5 | 71.8 | 75.0 | 72.1 | 74.1 | 66.1 |
| SDPPR8 | 188.5 | 95.5 | 99.4 | 81.1 | 117.7 | 83.6 |
| SW1000 (grams) | 153.4 | 137.3 | 144.0 | 129.6 | 134.4 | 141.5 |

Additional phenotypic data was collected from plants expressing the Le.SFT transgene under the control of the pAt.Erecta promoter (Table 13).

TABLE 13

Construct and event level phenotypic data for Le.SFT and WT plants.

|  | WT | Average | Event 1 | Event 2 | Event 3 | Event 4 | Event 5 | Event 6 |
|---|---|---|---|---|---|---|---|---|
| DOFR1 | 42.9 | 41.4 | 30 | 44.4 | 30.7 | 28 | 60.2 | 55 |
| DOR7 | 108.6 | 103.8 | 90.7 | 106.2 | 99 | 91.5 | 116.5 | 119 |
| PDR1R7 | 65.5 | 64.0 | 60.2 | 71 | 67 | 65 | 56.4 | 64.2 |
| BRPP | n/a | n/a | n/a | n/a | n/a | n/a | n/a | n/a |
| FNBR | 131.5 | 37.1 | 2.7 | 125.2 | 4.7 | 1 | 47.7 | 41.3 |
| FNLP | 156.8 | 50.7 | 15.7 | 142.6 | 18.1 | 18.3 | 56.7 | 52.7 |
| FNST | 25.3 | 13.7 | 13 | 17.7 | 13.7 | 17.3 | 9 | 11.3 |
| NDBR | 140.2 | 38.9 | 3 | 129.4 | 5.4 | 1 | 51 | 43.7 |
| NDMS | 32.4 | 17.9 | 16 | 25.8 | 16.3 | 21 | 12.3 | 16.3 |
| NDPL | 172.4 | 56.7 | 19 | 154.7 | 21.2 | 22 | 63.3 | 60 |
| PDPP | 473.3 | 201.3 | 53.7 | 432.3 | 69.8 | 85.7 | 279.3 | 287 |
| PFNB | 94.1 | 94.0 | 100 | 96.9 | 83.3 | 100 | 92.9 | 90.7 |
| PFNN | 90.4 | 86.4 | 82.5 | 92.3 | 83.7 | 83.5 | 88.8 | 87.6 |
| PFNS | 77.1 | 76.5 | 81.2 | 69.5 | 84.0 | 82.8 | 72.7 | 68.6 |
| PODBR | 366.2 | 141.8 | 3.7 | 361.5 | 15.5 | 1.3 | 238.7 | 230.7 |
| PODMS | 114 | 60.3 | 50 | 73.6 | 57.1 | 84.3 | 40.7 | 56.3 |
| Pods/Node | 2.7 | 3.6 | 2.8 | 2.8 | 3.3 | 3.9 | 4.4 | 4.8 |
| SDPPR8 | 1247.4 | 476.0 | 136.7 | 1036 | 148.5 | 183 | 655 | 697 |
| SW1000 (grams) | 167.7 | 153.2 | 170.0 | 182.8 | 157.5 | 148.5 | 131.5 | 128.8 |

Overall, soybean plants expressing the Le.SFT transgene had shorter plant height with less branching (FIG. 15) and an increased number of pods per node on average relative to wild type plants (Table 13). However, these effects were variable and event-specific. For example, Events 1, 3 and 4 displayed early flowering (DOFR1), while other events were neutral or actually had delayed flowering. In addition, some of the Le.SFT transgenic events showed increased pods per node on average to varying extents, while a couple of the events were neutral in terms of the average number of pods per node. Interestingly, two of the events (Events 5 and 6) had the greatest number of pods per node on average despite having a delay in flowering.

Additional phenotypic data was collected from plants expressing the Gm.FT5a transgene under the control of the pAt.Erecta promoter (Table 14).

TABLE 14

Construct and event level phenotypic data for Gm.FT5a and WT plants.

|  | WT | Average | Event 1 | Event 2 | Event 3 | Event 4 | Event 5 |
|---|---|---|---|---|---|---|---|
| DOFR1 | 48.2 | 29.9 | 32.2 | 29 | 28.6 | 29.2 | 30.5 |
| DOR7 | 110 | 92.5 | 96.6 | 90.4 | 91 | 92.8 | 91.8 |
| PDR1R7 | 61.8 | 62.7 | 64.4 | 61.4 | 62.4 | 63.6 | 61.3 |
| BRPP | 12.4 | 2.5 | 7 | 1.7 | 1 | 1.3 | 1.7 |
| FNBR | 105.6 | 7.3 | 20.3 | 4.7 | 3 | 4 | 4.3 |
| FNLP | 126.5 | 24.5 | 41.7 | 20 | 18.7 | 19.3 | 22.7 |
| FNST | 20.9 | 17.2 | 21.3 | 15.3 | 15.7 | 15.3 | 18.3 |
| NDBR | 108.6 | 7.5 | 21 | 5 | 3 | 4 | 4.3 |
| NDMS | 29 | 17.7 | 22 | 15.7 | 16.3 | 16 | 18.7 |
| NDPL | 137.6 | 25.2 | 43 | 20.7 | 19.3 | 20 | 23 |
| PDPP | 304.3 | 131.9 | 214.7 | 111 | 100.3 | 104.3 | 129.3 |
| PFNB | 97.2 | 98.0 | 97.3 | 93.3 | 100 | 100 | 100 |
| PFNN | 98.1 | 97.0 | 95.9 | 90 | 99.1 | 100 | 100 |
| PFNS | 72.1 | 97.0 | 97.1 | 98.1 | 96.1 | 95.8 | 97.9 |
| PODBR | 233.4 | 16.5 | 60.5 | 8 | 4 | 6 | 4 |
| PODMS | 75.1 | 108.6 | 159 | 98.5 | 95 | 92.5 | 98 |
| Pods/Node | 2.2 | 5.2 | 5.0 | 5.4 | 5.2 | 5.2 | 5.6 |
| SDPPR8 | 778.8 | 271.7 | 516 | 232.7 | 175.3 | 182.3 | 252 |
| SW1000 (grams) | 151.6 | 126.0 | 143.7 | 122.4 | 122.2 | 121.8 | 116.8 |

Transgenic soybean plants expressing the Gm.FT5a transgene flowered significantly earlier than wild type control plants and had an increased number of pods per node (similar to plants expressing the Gm.FT2a transgene). Indeed, soybean plants expressing the Gm.FT5a transgene had several phenotypes (similar to the Gm.FT2a transgenic plants), including reduced number of days to flowering (DOFR1), reduced number of branches (BRPP), fewer nodes per plant (NDPL), fewer nodes on branches (NDBR), reduced number of pods per plant (PDPP), and fewer pods on branches (PODBR), along with an increase in the number of pods per node and a decrease in the number of seeds per plant (Table 14). Overall, plants expressing the Gm.FT2a transgene had shorter plant height and less branching, but more pods per node (particularly on the main stem) relative to wild type control plants (FIG. 16).

Without being bound by any theory, these data support a model of FT overexpression acting in a dosage-dependent manner with the degree or extent of associated phenotypes (e.g., early flowering, increase in pods per node, and altered plant architecture) depending on (i) the level and timing of FT expression, (ii) tissue specificity of FT expression, and (iii) the relative activity and target specificity of the particular FT protein being expressed. For example, expression of the FT protein orthologs from other plant species in soybean may produce a more attenuated effect relative to overexpression of an endogenous FT protein (Gm.FT2a) in soybean, which may result from the non-native FT protein homologs having a lower activity in soybean. However, expression of some native FT proteins may not produce significant phenotypic effects if they have a different or specialized role in their native state or context. Different FT proteins may also act on different tissue targets and receptors and thus have differential effects on the various plant architecture and flowering traits and phenotypes.

Regardless of the activity level of the particular FT homolog, altered reproductive and plant architecture phenotypes appear to correlate with the timing and location of FT expression. Vegetative-stage expression of FT transgenes may be necessary to induce early flowering and/or cause increased numbers of floral meristems, flowers, pods, etc., per node of the plant. Indeed, FT expression in meristematic tissues during vegetative stages of development is shown with proper dosing of the FT transgene to cause reproductive changes in plants leading to increased numbers of flowers, pods, and/or seeds per node. In contrast, expression of a Gm.FT2a transgene under the control of leaf-preferred promoters produced very little, if any, phenotypic changes, relative to wild type plants. These data indicate that both the timing, and tissue specificity (or tissue preference), of FT expression are important factors that affect reproductive and/or yield-related phenotypic changes in transgenic plants.

The present data suggest that different FT proteins may have different activity levels and/or target specificities despite being expressed using the same pErecta promoter. While several constructs expressing Gm.FT2a, Zm.ZCN8, Nt.FT-like, and Gm.FT5a each caused early flowering and termination in addition to an increased number of pods per node, other constructs expressing Gm.FT2b and Le.SFT had different correlative effects on flowering. Expression of Gm.FT2b did cause early flowering and termination of plants but without a significant increase in the number of pods per node. On the other hand, Le. SFT expression showed increased pods per node and early termination despite a delay in flowering. Interestingly, increased numbers of pods per node in transgenic FT plants did not correlate with an extended reproductive duration (PDR1R7) and was not always aligned with early flowering (DOFR1) as noted above. These data suggest that reproductive changes in response to vegetative-stage expression of FT proteins in the meristem may operate through one or more independent mechanisms or pathways. Increased numbers of pods per node in transgenic FT plants may depend on the number of inflorescent and floral meristems induced from vegetative meristems at each node, which may occur independently of flowering time and/or reproductive duration. As noted above, however, reproductive duration may not necessarily correlate with the duration of flowering.

Example 7. Identification of Additional Vegetative-Stage Meristem Promoters

Having observed phenotypic effects with expression of Gm.FT2a under the control of a vegetative-stage, meristem-preferred promoter, pAt.Erecta, it is contemplated that other vegetative-stage, meristem-preferred (or meristem-specific) promoters may be used to drive expression of FT proteins to cause reproductive or yield-related traits or phenotypes in plants, such as increased number of pods per node (and/or per plant or main stem). Using the characterized expression pattern of the pAt.Erecta promoter (see Example 2), other vegetative-stage, meristem-preferred (or meristem-specific) promoters were identified from soybean, potato and *Arabidopsis*. Two bioinformatic approaches were utilized to identify candidate genes from other dicotyledonous species including, for example, *Arabidopsis*, soybean, *Medicago*, potato and tomato, having similar expression profiles to pAt.Erecta: BAR Espressolog and Expression Angler. See, e.g., BAR expressolog identification: expression profile similarity ranking of homologous genes in plant species," *Plant J* 71(6): 1038-50 (2012); and Toufighi, K et al., "The Botany Array Resource: e-Northerns, Expression Angling, and promoter analyses," *Plant J* 43(1): 153-163 (2005). The promoter sequences from these genes are thus proposed for use in expressing FT transgenes according to embodiments of the present invention.

Examples of gene promoters identified by this analysis include the following: four receptor like kinase (RLK) genes from soybean, including Glyma10g38730 (SEQ ID NO: 23), Glyma09g27950 (SEQ ID NO: 24), Glyma06g05900 (SEQ ID NO: 25), and Glyma17g34380 (SEQ ID NO: 26). Additional examples include receptor like kinase (RLK) gene promoters from potato, PGSC0003DMP400032802 (SEQ ID NO: 27) and PGSC0003DMP400054040 (SEQ ID NO: 28). It is possible that these RLK genes may be related structurally and/or functionally to Erecta and Erecta-like genes from *Arabidopsis* and other species since they are also RLK genes. Other vegetative stage, meristem-preferred promoters from *Arabidopsis* genes include the following: At.MYB17 (At.LMI2; At3g61250) (SEQ ID NO: 31), Kinesin-like gene (At5g55520) (SEQ ID NO: 32), AP2/B3-like genes including ALREM17 (SEQ ID NO: 33) or ALREM19, and Erecta-like 1 and 2 genes, At.Erl1 (SEQ ID NO: 34) and At.Erl2 (SEQ ID NO: 35). Each of these promoters and similar functional sequences may be operatively linked to a FT gene to cause ectopic expression of FT genes in one or more meristem(s) of plants at least during vegetative stage(s) of development.

With regard to the At.MYB17 (At.LMI2) gene, see Pastore, J L et al., "LATE MERISTEM IDENTITY 2 acts together with LEAFY to activate APETALA1," *Development* 138: 3189-3198 (2011), the entire contents and disclosure of which are incorporated herein by reference. With regard to the Kinesin-like gene, see Fleury, D et al., "The *Arabidopsis thaliana* Homolog of Yeast BRE1 Has a Function in Cell Cycle Regulation during Early Leaf and Root Growth," *Plant Cell,* 19(2): 417-432 (2007), the entire contents and disclosure of which are incorporated herein by reference. With regard to the REM17 and REM19 *Arabidopsis* genes, see Mantegazza, O et al., "Analysis of the *Arabidopsis* REM gene family predicts functions during flower development," *Ann Bot* 114(7): 1507-1515 (2014), the entire contents and disclosure of which are incorporated herein by reference. Further, with regard to the At.Erl2 gene, see "Special Issue: Receptor-like Kinases," *JIPB* 55(12): 1181-1286 (2013), and particularly Shpak, E., "Diverse Roles of ERECTA Family Genes in Plant Development," *JIPB* 55(12): 1251-1263 (2013), the entire contents and disclosures of which are incorporated herein by reference.

Example 8. Expression of Flowering Locus T Gene, Gm.FT2a, Under Control of a pAt.Erl1 Promoter Alters Flowering Time and Pods Per Node in Soybean A transformation vector containing Gm.FT2a under control of the vegetative stage, meristem-preferred pAt.Erl1 promoter (SEQ ID NO: 34) was constructed and used to transform soybeans via *Agrobacterium*-mediated transformation. Transgenic plants generated from these events were characterized for their phenotypes in the greenhouse with a 14 to 14.5 hour natural daylight photoperiod. For each pAt.Erl1:Gm.FT2a construct, six events were tested (6 plants per event). Six plants were also tested and averaged for wild type (WT) control plants. The following matrices were collected for phenotypic characterization of these plants and expressed as an average for each Event as well as the wild type plants (see Table 15). A column providing an average for all the Events per trait is further provided.

Transgenic soybean plants expressing a pAt.Erl1::Gm.FT2a construct flowered earlier than wild type control plants and had an increased number of pods per node (similar to plants expressing the Gm.FT2a transgene under control of the pAt.Erecta promoter). Indeed, soybean plants expressing pAt.Erl1:Gm.FT2a had several phenotypes similar to the pAt.Erecta:Gm.FT2a transgenic plants, including reduced number of days to flowering (DOFR1), reduced number of days to R7 (DOR7), reduced number of branches (BRPP), fewer nodes per plant (NDPL), a reduced number of pods per plant (PDPP), along with an increase in the number of pods per node (Table 15), relative to wild type control plants. However, several phenotypes observed in pAt.Erecta::Gm.FT2a plants, such as number of pods on main stem (PODMS), number of pods on branches (PODBR), and weight of 1000 seeds (SW1000), were less pronounced in the pALErl1:Gm.FT2a expressing transgenic plants.

The expression pattern for the *Arabidopsis* Erecta-like 1 promoter (pAt.Erl1) in soybean as measured by GUS staining is more restricted than the expression pattern of pAt.Erecta in soybean as described above. pAt.Erl1 drives GUS expression in vegetative axillary meristems and in early floral meristems derived from axillary tissue. However, GUS staining is not observed in the shoot apical meristem at any stage where it can be distinguished from other meristematic tissues of the developing plant. Expression of the GUS reporter under the control of the pAt.Erl1 promoter is not observed in leaf tissue, stem or root at any stage (data not shown). Given that FT expression under the control of either the pAt.Erecta or pAt.Erl1 promoter induced early flowering and increased pods per node, vegetative expression of an FT transgene at or near the meristem(s) of a plant may generally be sufficient to induce these reproductive and yield-related phenotypes or traits.

Having described the present disclosure in detail, it will be apparent that modifications, variations, and equivalent embodiments are possible without departing from the spirit and scope of the present disclosure as described herein and in the appended claims. Furthermore, it should be appreciated that all examples in the present disclosure are provided as non-limiting examples.

TABLE 15

Phenotypic data for pAt.Erl1:Gm.FT2a and WT plants.

|  | WT | Average | Event 1 | Event 2 | Event 3 | Event 4 | Event 5 | Event 6 |
| --- | --- | --- | --- | --- | --- | --- | --- | --- |
| DOFR1 | 46.1 | 32.6 | 40.0 | 32.3 | 34.0 | 29.3 | 28.2 | 31.8 |
| DOR7 | 115.1 | 99.0 | 109.7 | 99.0 | 99.0 | 93.0 | 91.7 | 101.7 |
| PDR1R7 | 69.0 | 66.4 | 69.7 | 66.7 | 65.0 | 63.7 | 63.5 | 69.8 |
| BRPP | 23.5 | 7.4 | 16.0 | 6.0 | 9.7 | 1.3 | 4.3 | 7.3 |
| NDBR | 277.6 | 80.8 | 215.7 | 51.7 | 139.3 | 3.3 | 18.0 | 56.7 |
| NDMS | 29.8 | 32.3 | 30.7 | 33.7 | 32.7 | 30.7 | 32.7 | 33.3 |
| NDPL | 307.4 | 113.0 | 246.3 | 85.3 | 172.0 | 34.0 | 50.7 | 90.0 |
| PDPP | 605.8 | 346.4 | 447.3 | 349.7 | 493.7 | 240.7 | 194.7 | 352.3 |
| PODBR | 503.1 | 173.7 | 332.3 | 164.7 | 323.3 | 8.3 | 42.7 | 171.0 |
| PODMS | 103.0 | 172.7 | 115.0 | 185.0 | 170.3 | 232.3 | 152.0 | 181.3 |
| Pods/Node | 1.9 | 4.0 | 2.1 | 4.1 | 2.9 | 7.1 | 3.8 | 4.0 |
| SDPPR8 | 1290.0 | 747.5 | 1129.0 | 603.5 | 881.0 | 577.0 | 432.3 | 862.3 |
| SW1000 (grams) | 157.6 | 157.3 | 187.7 | 142.6 | 173.8 | 144.3 | 144.9 | 150.3 |

What is claimed is:

1. A recombinant DNA construct comprising a polynucleotide sequence encoding a florigenic FT protein comprising an amino acid sequence having at least 80% identity to SEQ ID NO: 2 and operably linked to a promoter comprising a polynucleotide sequence having at least 90% identity to SEQ ID NO: 21, SEQ ID NO: 22 or SEQ ID NO: 38.

2. The recombinant DNA construct of claim 1, wherein said florigenic FT protein comprises an amino acid sequence having at least 90% identity to SEQ ID NO: 2.

3. The recombinant DNA construct of claim 1, wherein said florigenic FT protein comprises an amino acid sequence having at least 95% identity to SEQ ID NO: 2.

4. The recombinant DNA construct of claim 1, wherein said florigenic FT protein comprises the amino acid sequence SEQ ID NO: 2.

5. The recombinant DNA construct of claim 1, wherein said promoter comprises a polynucleotide sequence having at least 90% identity to SEQ ID NO: 21.

6. The recombinant DNA construct of claim 1, wherein said promoter comprises SEQ ID NO: 21.

7. The recombinant DNA construct of claim 1, wherein said promoter comprises a polynucleotide sequence having at least 90% identity to SEQ ID NO: 22 or SEQ ID NO: 38.

8. The recombinant DNA construct of claim 1, wherein said promoter comprises SEQ ID NO: 22 or SEQ ID NO: 38.

9. The recombinant DNA construct of claim 1, wherein said florigenic FT protein is encoded by a polynucleotide comprising at least 90% identity to SEQ ID NO:1.

10. The recombinant DNA construct of claim 1, wherein said recombinant DNA construct comprises SEQ ID NO:1.

11. A DNA molecule or vector comprising the recombinant DNA construct of claim 1.

12. A transgenic plant, or part thereof, wherein the plant or plant part thereof comprises the recombinant DNA construct of claim 1.

13. The transgenic plant, or part thereof, of claim 12, wherein the transgenic plant or part thereof is homozygous for the insertion of the recombinant DNA construct.

14. The transgenic plant, or part thereof, of claim 12, wherein the transgenic plant or part thereof is hemizygous for the insertion of the recombinant DNA construct.

15. The transgenic plant, or part thereof, of claim 12, wherein the transgenic plant or a plant grown from the part thereof is a short day plant.

16. The transgenic plant, or part thereof, of claim 12, wherein the transgenic plant or a plant grown from the part thereof is a dicotyledonous plant.

17. The transgenic plant, or part thereof, of claim 16, wherein the transgenic plant or a plant grown from the part thereof is a leguminous plant.

18. The transgenic plant, or part thereof, of claim 17, wherein the transgenic plant or a plant grown from the part thereof is soybean.

19. The transgenic plant, or part thereof, of claim 18, wherein the transgenic soybean plant or transgenic soybean plant grown from the part thereof produces more pods per node than a control plant not having the recombinant DNA construct.

20. The transgenic plant, or part thereof, of claim 12, wherein the transgenic plant or a plant grown from the part thereof produces more flowers per node than a control plant not having the recombinant DNA construct.

21. The transgenic plant, or part thereof, of claim 12, wherein the transgenic plant or a plant grown from the part thereof produces more bolls, siliques, fruits, nuts or pods per node of the transgenic plant than a control plant not having the recombinant DNA construct.

22. The transgenic plant, or part thereof, of claim 12, wherein the transgenic plant or a plant grown from the part thereof flowers earlier than a control plant not having the recombinant DNA construct.

23. The transgenic plant or part thereof of claim 12, wherein the transgenic plant or a plant grown from the part thereof has more floral racemes per node than a control plant not having the recombinant DNA construct.

24. The transgenic plant part of claim 12, wherein the transgenic plant part comprises the recombinant DNA construct and is one of the following: a seed, fruit, leaf, cotyledon, hypocotyl, meristem, embryo, endosperm, root, shoot, stem, pod, flower, inflorescence, stalk, pedicel, style, stigma, receptacle, petal, sepal, pollen, anther, filament, ovary, ovule, pericarp, phloem, or vascular tissue.

* * * * *